US005789172A

United States Patent [19]
Still et al.

[11] Patent Number: 5,789,172
[45] Date of Patent: *Aug. 4, 1998

[54] METHODS OF DETERMINING THE STRUCTURE OF A COMPOUND ENCODED BY IDENTIFIERS HAVING TAGS

[75] Inventors: W. Clark Still, Clinton; Michael H. Wigler, Lloyd Harbor, both of N.Y.; Michael H. J. Ohlmeyer, Plainsboro, N.J.; Lawrence W. Dillard, Plainsboro, N.J.; John C. Reader, Princeton, N.J.

[73] Assignees: Trustees of the Columbia University in the City of New York, New York City; Cold Spring Harbor Laboratory, Cold Spring Harbor, both of N.Y.

[*] Notice: The term of this patent shall not extend beyond the expiration date of Pat. No. 5,565,324.

[21] Appl. No.: 680,716

[22] Filed: Jul. 11, 1996

Related U.S. Application Data

[63] Continuation of Ser. No. 227,007, filed as PCT/US93/09345, filed Oct. 1, 193, published as WO94/08051 on Apr. 14, 1994, Pat. No. 5,565,324, which is a continuation-in-part of Ser. No. 159,861, Nov. 30, 1993, abandoned, which is a continuation-in-part of Ser. No. 130,271, Oct. 1, 1993, abandoned, which is a continuation-in-part of Ser. No. 13,948, Feb. 4, 1993, abandoned, which is a continuation-in-part of Ser. No. 955,371, Oct. 1, 1992, abandoned.

[51] Int. Cl.⁶ .......................... C12Q 1/68; G01N 33/53; G01N 33/543
[52] U.S. Cl. ..................... 435/6; 435/7.1; 436/501; 436/518; 436/528; 436/529; 436/531; 436/534
[58] Field of Search .................. 435/6, 7.1; 436/501, 436/518, 528, 529, 531, 534

[56] References Cited

U.S. PATENT DOCUMENTS

| | | | |
|---|---|---|---|
| 4,631,211 | 12/1986 | Houghten | 428/35.1 |
| 4,650,750 | 3/1987 | Giese | 435/7.72 |
| 4,709,016 | 11/1987 | Giese | 530/391.5 |
| 4,755,558 | 7/1988 | Kalbag | 525/54.1 |
| 4,833,092 | 5/1989 | Geysen | 436/501 |
| 4,937,188 | 6/1990 | Giese | 435/91 |
| 5,010,175 | 4/1991 | Rutter, et al. | 530/334 |
| 5,182,366 | 1/1993 | Huebner et al. | 530/334 |
| 5,194,392 | 3/1993 | Geysen | 436/518 |
| 5,225,533 | 7/1993 | Rutter, et al. | 530/334 |
| 5,252,296 | 10/1993 | Zuckerman, et al. | 422/116 |
| 5,266,684 | 11/1993 | Rutter, et al. | 530/334 |
| 5,270,170 | 12/1993 | Schatz, et al. | 435/7.37 |
| 5,288,514 | 2/1994 | Ellman | 435/4 |
| 5,360,819 | 11/1994 | Giese | 514/538 |
| 5,516,931 | 5/1996 | Giese | 560/59 |
| 5,565,324 | 10/1996 | Still et al. | 435/6 |
| 5,573,905 | 11/1996 | Lerner, et al. | 935/6 |

FOREIGN PATENT DOCUMENTS

| | | |
|---|---|---|
| WO 91 17823 | 11/1991 | WIPO |
| WO 92 00091 | 1/1992 | WIPO |
| WO 92 09300 | 6/1992 | WIPO |
| WO 92 10588 | 6/1992 | WIPO |
| WO 93 06121 | 4/1993 | WIPO |
| WO 93 12527 | 6/1993 | WIPO |
| WO 93 19205 | 9/1993 | WIPO |
| WO 93 20242 | 10/1993 | WIPO |
| WO 94 02515 | 2/1994 | WIPO |
| WO 94 04558 | 3/1994 | WIPO |
| WO 94 06017 | 3/1994 | WIPO |
| WO 94 06291 | 3/1994 | WIPO |

OTHER PUBLICATIONS

Alper, J., 1993. "Oligonucleotides Surge into Clinical Trials," Bio/Technology 11:1225 (Exhibit 22).

Amato, I., 1992, "Speeding Up a Chemical Game of Chance," Science 257:330–331 (Exhibit 23).

Baum, R., 1993. "Solid–phase Synthesis of Benzodiazepines," C&E News 71:33–34 (Exhibit 24).

Baum, R., 1994. "Combinatorial Approaches Provide Fresh Leads for Medincinal Chemistry," C & E News 72:20–26 (Exhibit 25).

Blake et al., 1992, "Evaluation of Peptide Libraries: An Iterative Strategy to analyze the Reactivity of Peptide Mixtures with Antibodies," Bioconjugate Chem. 3:510–513 (Exhibit 26).

Bock et al., 1992, "Selection of Single–stranded DNA Molecules That Bind and Inhibit Human Thrombin," Nature 335:564–566 (Exhibit 27).

Borchardt et al., 1994, "Synthetic Receptor Binding Elucidated with an Encoded Combinatorial Library," J. Am. Chem. Soc. 116:371–372 (Exhibit 28).

Borman, S., 1992, "DNA Oligomers Inhibit Enzyme Activity," C& E News 70:5 (Exhibit 29).

(List continued on next page.)

*Primary Examiner*—Lora M. Green
*Attorney, Agent, or Firm*—Pennie & Edmonds LLP

[57] ABSTRACT

Encoded combinatorial chemistry is provided, where sequential synthetic schemes are recorded using organic molecules, which define choice of reactant, and stage, as the same or different bit of information. Various products can be produced in the multi-stage synthesis, such as oligomers and synthetic non-repetitive organic molecules. Conveniently, nested families of compounds can be employed as identifiers, where number and/or position of a substituent define the choice. Alternatively, detectable functionalities may be employed, such as radioisotopes, fluorescers, halogens, and the like, where presence and ratios of two different groups can be used to define stage or choice. Particularly, pluralities of identifiers may be used to provide a binary or higher code, so as to define a plurality of choices with only a few detachable tags. The particles may be screened for a characteristic of interest, particularly binding affinity, where the products may be detached from the particle or retained on the particle. The reaction history of the particles which are positive for the characteristic can be determined by the release of the tags and analysis to define the reaction history of the particle.

24 Claims, 4 Drawing Sheets

OTHER PUBLICATIONS

Bray et al., 1990, "The Simultaneous Multiple Production of Solution Phase Peptides; Assessment of the Geysen Method of Simultaneous Peptide Synthesis," Tetrahedron Letters 31:5811–5814 (Exhibit 30).

Brenner et al., 1992, "Encoded Combinatorial Chemistry," Proc. Natl. Acad. Sci. USA 89:5381–5383 (Exhibit 31).

Brummel et al., 1994, "A Mass Spectrometric Solution to the Address Problem of Combinatorial Libraries," Science 264:399–402 (Exhibit 32).

Bunin et al., 1992, "A General and Expedient Method for the Solid–Phase Synthesis of 1,4–Benzodiazepine Derivatives," J. Am. Chem. Soc. 114:10997–10998 (Exhibit 33).

Cho et al., 1993, "An Unnatural Biopolymer," Science 261:1303–1305 (Exhibit 34).

Danheiser, S.L., 1994, "Current Trends in Synthetic Peptide and Chemical Diversity Library Design," GEN 14:10 & 31 (Exhibit 35).

Dimond, P.F., 1984, "Pharmacopeia Inc.'s Novel Molecular Tagging System Finds Molecular," GEN 14:32 & 38 (Exhibit 36).

Fisher, L.M., 1992, "New Drugs by Process of Elimination," New York Times 142:D1 & D13 (Exhibit 37).

Fodor et al., 1991, "Light–Directed, Spatially Addressable Parallel Chemical Synthesis," Science 251:767–773 (Exhibit 38).

Furka et al., 1988, "More Peptides by Less Labour," Abstract 10th Intl. Symp. Med. Chem., Budapest, Hungary p. 288 (Exhibit 39).

Furka et al., 1991, "General Method for Rapid Synthesis of Multicomponent Peptide Mixtures," Int. J. Peptide Protein Res. 37:487–493 (Exhibit 40).

Furka et al., 1988, "Cornucopia of Peptide by Synthesis," Abstract 14th Int. Congr. Biochem., Prague, Czechslovakia 5:46 (Exhibit 41).

Geysen et al., 1984, "Use of Peptide Synthesis to Probe Viral Antigens for Eptiopes to ao Resolution of a Single Amino Acid," Proc. Natl. Acad. Sci. USA 81:3998–4002 (Exhibit 42).

Geysen et al., 1993: "Screening Chemically Synthesized Peptide Libraries for Biologically–Relevant Molecules," Bioorganic & Medicinal Chemistry Letters 3:397–404 (Exhibit 43).

Grimsrud, E.P., 1992, "The Electron Capture Detector," Detectors for Capillary Chromatography, Hill, H.H and McMinn, D.G. eds., John Wiley and Sons, Inc. pp. 83–107 (Exhibit 44).

Harlow et al., 1988, "Antibody Capture Assays–Detecting and Quantitating Antigens Using Antibody Excess Assays," Antibodies: A Laboratory Manual, Cold Spring Harbor Laboratory pp. 570–573 (Exhibit 45).

Houghten, R.A., 1985, "General Method for Rapid Solid–Phase Synthesis of Large Numbers of Peptides: Specificity of Antigen–Antibody Interaction at the level of Individual Amino Acids," Proc. Natl. Acad. Sci. USA 82:5131–5135 (Exhibit 46).

Houghten et al., 1991, "Generation and Use of Synthetic Peptide Combinatorial Libraries for Basic Research and Drug Discovery," Nature 354:84–86 (Exhibit 48).

Jung et al., "Multiple Peptide Synthesis Methods and Their Applications," Angew. Chem. Int. Ed. Engl. 31:367–383 (Exhibit 49).

Kerr et al., 1993, "Encoded Combinatorial Peptide Libraries Containing Non–Natural Amino Acids," J. Am. Chem. Soc. 115:2529–2531 (Exhibit 50).

Lam et al., 1991, "A New Type of Synthetic Peptide Library for Identifying Ligand–Binding Activity," Nature 354:82–84 (Exhibit 51).

Lam et al., 1993, The Chemical Synthesis of Large Random Peptide Libraries and Their Use for the Discovery of Ligands for Macromolecular Acceptors, Bioorganic & Medicinal Chemistry Letters 3:419–424 (Exhibit 52).

Merrifield, B., 1986, "Solid Phase Synthesis," Science 232:341–347 (Exhibit 53).

Needels et al., 1993, "Generation and Screening of an Oligonucleotide–Encoded Synthetic Peptide Library," Proc. Natl. Acad. Sci. USA 90:10700–10704 (Exhibit 54).

Nelson, B. 1994, "Bar Code System Helps Scientists Identify New Compounds for Drugs," Columbia University Record 19:3 (Exhibit 55).

Nielsen et al., 1993, "Synthetic Methods for the Implementation of Encoded Combinatorial Chemistry," J. Am. Chem. Soc. 115:9812–9813 (Exhibit 56).

Ohlmeyer et al., 1993, "Complex Synthetic Chemical Libraries Indexed with Molecular Tags," Proc. Acad. Sci. USA 90:1464–1468 (Exhibit 57).

Pavia et al., 1993, "The Generation of Molecular Diversity," Bioorganic & Medicinal Chemistry Letters 3:387–396 (Exhibit 58).

Stone, D., 1993, "The Hot New Field of Molecular Diversity," Bio/Technology 11:1508–1509 (Exhibit 59).

Giese, R.W., 1983, "Electrophoric release tags; utrasensitive molecular labels providing multiplicity," Trends in Analytical Chemistry 2:166–168 (Exhibit J).

Tan et al., 1980, "Design and Synthesis of Multidetachable Resin Supports for Solid–Phase Peptide synthesis," J. Am. Chem. Soc. 102:6117–6127 (Exhibit K).

Meriwether, A., 1982, "Advanced Concepts At Oak Ridge Conference," Clin. Chem. News publ. by Am. Assoc. Clin. Chem. 8:6.

Scan 131(3.513min) Of Data: PHAR088E.D

Scan 131(3.513min) Of Data: PHAR088E.D
Pharmacopeia GC/CIMS CH4/NH3(g) 90/350 A/D=1

| m/z | abund. | m/z | abund. | m/z | abund. | m/z | abund. |
|---|---|---|---|---|---|---|---|
| 203.30 | 2 | 237.05 | 17 | 255.20 | 12 | 272.05 | 11 |
| 216.20 | 4 | 239.05 | 411 | 255.45 | 12 | 274.05 | 1000 |
| 218.05 | 70 | 240.05 | 48 | 256.20 | 23 | 275.05 | 111 |
| 219.20 | 25 | 241.20 | 4 | 257.05 | 15 | 276.20 | 11 |
| 221.20 | 5 | 247.30 | 5 | 259.05 | 6 | 277.20 | 3 |
| 233.95 | 2 | 254.20 | 84 | 265.05 | 8 | 297.15 | 4 |
| 236.20 | 52 | | | | | | |

Scan 124 (3.434 min) Of Data: PHAR071.D
Pharmacopeia GC/CIMS CH4/NH3(g) 90/350 A/D=1

| m/z | abund. | m/z | abund. | m/z | abund. | m/z | abund. |
|---|---|---|---|---|---|---|---|
| 203.05 | 1 | 238.05 | 1 | 260.20 | 11 | 279.05 | 113 |
| 210.20 | 1 | 239.20 | 2 | 261.05 | 13 | 280.05 | 10 |
| 213.20 | 1 | 240.20 | 8 | 262.20 | 2 | 281.05 | 1 |
| 220.20 | 1 | 241.20 | 7 | 263.20 | 1 | 289.20 | 1 |
| 222.05 | 8 | 243.05 | 429 | 269.05 | 1 | 290.05 | 2 |
| 223.05 | 3 | 244.05 | 47 | 274.05 | 2 | 291.05 | 1 |
| 224.20 | 1 | 245.05 | 3 | 275.30 | 4 | 292.05 | 1 |
| 224.55 | 1 | 251.20 | 1 | 276.20 | 13 | 295.15 | 3 |
| 225.30 | 1 | 258.20 | 9 | 278.05 | 1000 | | |

Scan 143 (3.648 min) Of Data: PHAR072.D
Pharmacopeia GC/CIMS CH4/NH3(g) 90/350 A/D=1

| m/z    | abund. | m/z    | abund. | m/z    | abund. | m/z    | abund. |
|--------|--------|--------|--------|--------|--------|--------|--------|
| 208.20 | 7      | 244.05 | 66     | 262.20 | 124    | 278.20 | 39     |
| 223.20 | 7      | 245.20 | 35     | 263.05 | 18     | 279.20 | 13     |
| 226.20 | 102    | 247.20 | 493    | 264.05 | 25     | 280.20 | 11     |
| 227.30 | 42     | 248.20 | 49     | 265.20 | 21     | 282.20 | 1000   |
| 241.20 | 9      | 257.95 | 12     | 267.20 | 7      | 283.20 | 115    |
| 242.95 | 34     | 260.55 | 13     | 273.20 | 12     | 284.20 | 9      |

Scan 124 (3.434 min) Of Data: PHARIMIX.D
Pharmacopeia GC/CIMS CH4/NH3(g) 90/350 A/D=1

| m/z | abund. | m/z | abund. | m/z | abund. | m/z | abund. |
|---|---|---|---|---|---|---|---|
| 203.05 | 1 | 237.20 | 2 | 261.05 | 13 | 283.20 | 112 |
| 206.95 | 1 | 239.05 | 178 | 262.05 | 9 | 284.05 | 11 |
| 210.30 | 1 | 240.05 | 27 | 263.20 | 3 | 285.05 | 1 |
| 213.05 | 1 | 241.05 | 8 | 264.20 | 12 | 285.95 | 1 |
| 213.95 | 1 | 243.05 | 409 | 265.20 | 13 | 288.30 | 1 |
| 218.05 | 4 | 244.05 | 49 | 266.05 | 2 | 290.05 | 1 |
| 219.20 | 2 | 245.05 | 7 | 267.20 | 1 | 291.20 | 2 |
| 220.05 | 1 | 247.05 | 402 | 268.30 | 1 | 292.05 | 2 |
| 222.05 | 9 | 248.05 | 44 | 269.05 | 1 | 293.40 | 1 |
| 223.05 | 3 | 249.20 | 4 | 274.05 | 432 | 293.75 | 1 |
| 224.20 | 2 | 251.20 | 1 | 275.05 | 51 | 294.40 | 2 |
| 225.20 | 2 | 254.05 | 5 | 276.05 | 18 | 295.25 | 3 |
| 226.20 | 9 | 256.20 | 6 | 278.05 | 996 | 296.25 | 2 |
| 227.05 | 3 | 257.05 | 7 | 279.05 | 112 | 297.25 | 2 |
| 228.20 | 1 | 258.20 | 12 | 280.20 | 18 | 298.15 | 1 |
| 229.20 | 1 | 259.20 | 3 | 282.20 | 1000 | 299.25 | 4 |
| 236.05 | 2 | 260.20 | 10 | | | | |

METHODS OF DETERMINING THE STRUCTURE OF A COMPOUND ENCODED BY IDENTIFIERS HAVING TAGS

This application is a continuation of Ser. No. 08/227,007, filed Apr. 13, 1994, now U.S. Pat. No. 5,565,324, which is a continuation-in-part of U.S. Ser. No. 08/159,861, filed Nov. 30, 1993, now abandoned, which is a continuation-in-part of U.S. Ser. No. 08/130,271, filed Oct. 1, 1993, now abandoned, which is a continuation-in-part of U.S. Ser. No. 08/013,948, filed Feb. 4, 1993, now abandoned which is a continuation-in-part of U.S. Ser. No. 07/955,371, filed Oct. 1, 1992, now abandoned, also filed as PCT/US93/09345, filed Oct. 1, 1993, published as WO94/08051 on Apr. 14, 1994, the contents of all of which are hereby incorporated by reference into the subject application.

TECHNICAL FIELD

The field of this invention concerns combinatorial chemistry which involves syntheses having a plurality of stages, with each stage involving a plurality of choices, where large numbers of products having varying compositions are obtained.

BACKGROUND OF THE INVENTION

There is substantial interest in devising facile methods for the synthesis of large numbers of diverse compounds which can then be screened for various possible physiological or other activities. Typically such a synthesis involves successive stages, each of which involves a chemical modification of the then existing molecule. For example, the chemical modification may involve the addition of a unit, e.g. a monomer or synthon, to a growing sequence or modification of a functional group. By employing syntheses where the chemical modification involves the addition of units, such as amino acids, nucleotides, sugars, lipids, or heterocyclic compounds where the units may be naturally-occurring, synthetic, or combinations thereof. One may create a large number of compounds. Thus, even if one restricted the synthesis to naturally-occurring units or building blocks, the number of choices would be very large, 4 in the case of nucleotides, 20 in the case of the common amino acids, and essentially an unlimited number in the case of sugars.

One disadvantage heretofore inherent in the production of large number of diverse compounds, where at each stage of the synthesis there are a significant number of choices, is the fact that each individual compound will be present in a minute amount. While a characteristic of a particular compound, e.g. a physiological activity, may be determinable, it is usually impossible to identify the chemical structure of this particular compound present.

Moreover, physiologically-active compounds have historically been discovered by assaying crude broths using Edisonian or stochastic techniques, where only a relatively few compounds are assayed at a time, or where a limited number of structural similar homologs of naturally-occurring physiologically-active compounds are assayed. Two of the major problems has been associated with the use of such crude broths, namely, the necessity to purify the reaction mixture into individual component compounds and the time-consuming effort required to establish the structure of the compound once purified.

To address these disadvantages and problems, techniques have been developed in which one adds individual units as part of a chemical synthesis sequentially, either in a controlled or a random manner, to produce all or a substantial proportion of the possible compounds which can result from the different choices possible at each sequential stage in the synthesis. However, for these techniques to be successful it is necessary for the compounds made by them to be amenable to methods which will allow one to determine the composition of a particular compound so made which shows a characteristic of interest.

One such approach involves using a chip which allows for separate analysis at physically separate sites on the surface of the chip (Fodor et al., *Science* 251: 767 [1991]). By knowing what reactant is added sequentially at each such site, one can record the sequence of events and thus the series of reactions. If one then subjects the chip to a screening method for a particular desired characteristic and detects the characteristic one can really determine the compound synthesized at the site which demonstrates that characteristic.

Another such technique involves the theoretical synthesis of oligonucleotides in parallel with the synthesis of oligopeptides as the compounds of interest (Brenner and Lerner, *PNAS USA* [1992] 81: 5381–5383).

Further techniques are also disclosed in the following publications: Amoto, *Science* (1992) 257, 330–331 discusses the use of cosynthesized DNA labels to identify polypeptides. Lam, et al., *Nature* (1991) 354, 82–84 describe a method for making large peptide libraries. Houghton, et al., *Nature* (1991) 354, 84–86 and Jung and Beck-Sickinger, *Angew. Chem. Int. Ed. Engl.* (1992) 91, 367–383 describe methodology for making large peptide libraries. Kerr et al., *J. Amer. Chem. Soc.*, (1993) 115, 2529–31 teach a method of synthesizing oligomer libraries encoded by peptide chains.

However, since methods such as the preceding typically require the additum of like moieties, there is substantial interest in discovering methods for producing compounds which are not limited to sequential addition of like moieties. Such methods would find application, for example, in the modification of steroids, antibiotics, sugars, coenzymes, enzyme inhibitors, ligands and the like, which frequently involve a multi-stage synthesis in which one would wish to vary the reagents and/or conditions to provide a variety of compounds. In such methods the reagents may be organic or inorganic reagents, where functionalities may be introduced or modified, side groups attached or removed, rings opened or closed, stereochemistry changed, and the like. (See, for example, Bunin and Ellman, *JACS* 114, 10997 [1992].) For such a method to be viable, however, there needs to be a convenient way to identify the structures of the large number of compounds which result from a wide variety of different modifications. Thus, there is a need to find a way whereby the reaction history may be recorded, and desirably, the structures of the results compound identified.

Finally as the size of a library compounds so synthesized increases, known techniques of structure elucidation and product segregation introduce substantial inefficiencies and uncertainties which hinder the accurate determination of the structure of any compound identified as being of interest. Thus, there is a substantial need for new methods which will permit the synthesis of complex combinatorial chemical libraries which readily permit accurate structural determination of individual compounds within the library which are identified as being of interest.

Finally, international applications WO91/17823 and WO92/09300 concern combinatorial libraries.

Many of the disadvantages of the previously-described methods as well as many of the needs not met by them are addressed by the present invention which, as described more fully hereinafter, provides marlad advantages over these previously-described methods.

SUMMARY OF THE INVENTION

Methods and compositions are provided for encoded combinatorial chemistry, whereby at each stage of the synthesis, a support such as a particle upon which a compound is being synthesized is uniquely tagged to define a particular event, usually chemical, associated with the synthesis of the compound on the support. The tagging is accomplished using identifier molecules which record the sequential events to which the supporting particle is exposed during synthesis, thus providing a reaction history for the compound produced on the support.

Each identifier molecule is characterized by being stable under the synthetic conditions employed, by remaining associated with the supports during the stage of the synthesis, by uniquely defining a particular event during the synthesis which reflects a particular reaction choice at a given stage of the synthesis, by being distinguishable from other components that may be present during assaying, and by allowing for detachment of a tag component which is discernible by a convenient, analytical technique.

The identifiers of this invention are used in combination with one another to form a binary or higher order encoding system permitting a relatively small number of identifiers to be used to encode a relatively large number of reaction products. For example, when used in a binary code N identifiers can uniquely encode up to $2^N$ different compounds.

Moreover, the identifiers of this invention need not be bound serially through a previous identifier but rather are individually bound to the substrate, either directly or through the product being synthesized. The identifiers are not sequencable. Furthermore, the identifiers contain a cleavable member or moiety which permits detachment of a tag component which can be readily analyzed.

Conveniently, the combinatorial synthesis employs definable solid supports upon which reactions are performed and to which the identifiers are bound. The individual solid supports or substrates carrying the final product compounds may be screened for a characteristic of interest and the reaction history determined by analyzing the associated identifier tags.

DETAILED DESCRIPTION OF THE INVENTION

Figure 1:
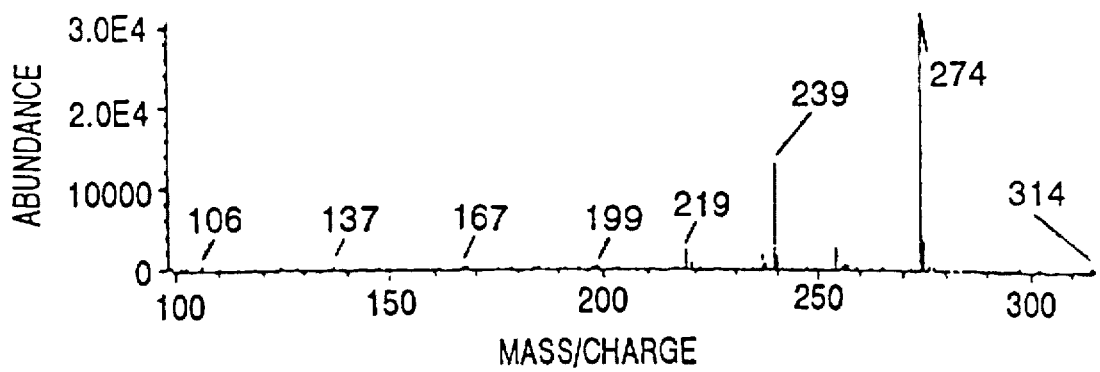
FIG. 1 illustrates the analysis of tag 4 by mass spectroscopy. Two signals corresponding to tag 4 were observed.
Figure 1:
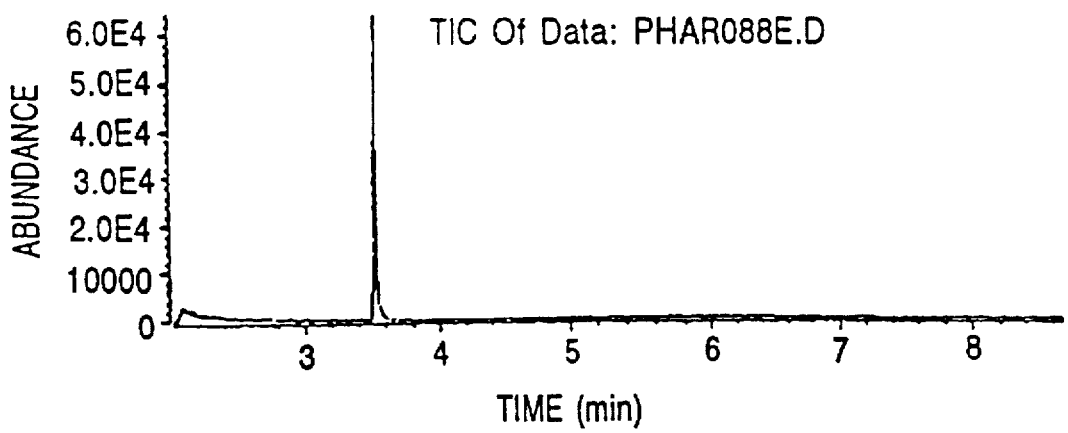

As used in this application the term "tag" or "T" means a chemical moiety which possesses two properties. First, it is capable of being distinguished from all other chemical moieties. Second, it is capable of being detected when present at $10^{-18}$ to $10^{-9}$ mole. These two properties may be embodied in a single chemical structure. Alternatively, these properties may be embodied in separate chemical structures which are linked together. In this latter case, one of the chemical structures, which may be designated $\underline{C}$ (or in the case of more than one such structure $\underline{C}$, $\underline{C}'$, etc.) provides the property of rendering the tag distinguishable from other tags while the other chemical structure, E, provides the property of rendering the tag detectable and optionally may provide the property of rendering the tag separable from other tags.

As used in this application, the term "linker" or "L" means a chemical moiety which possesses three properties. First, it is attachable to a solid support. Second, it is attachable to a tag. Third, when it is attached to both a solid support and a tag, it is cleavable such that the tag may be released from the solid support. These three properties may be embodied in a single chemical structure. Alternatively, these properties are embodied in three chemical structures which are linked together. In this latter case one of the chemical structures, which may be designated $F^1$, provides the property of rendering the linker attachable to the solid support; the second chemical structure, which may be designated V, provides the property of rendering the linker cleavable; and the third chemical structure which may be designed A', provides the property of rendering the linker attachable to the tag. Desirably, the chemical structures V and A' are one and the same, in which case V—A' may be designated $F^2$.

As used in this application, the term "identifier" means a chemical entity which includes both a tag and a linker. Thus, in the broadest sense an identifier may be represented by the formula L—T while specific embodiments of the identifier may be represented by the formulae F'—V—A'—T; $F^1$—V—A'—C—E (or $F^1$—V—A'—E—$\underline{C}$); L—$\underline{C}$—E (or L—E—$\underline{C}$); and L—$\underline{C}$—E—$\underline{C}'$.

As used in this application, the term "bound identifier" means an identifier attached to a solid support.

As used herein, the term "choice" means the alternative variables for a given stage in a combinatorial synthesis, such as reactant, reagent, reaction conditions, and combinations thereof. The term "stage" corresponds to a step in the sequential synthesis of a compound or ligand; the compound or ligand being the final product of a combinatorial synthesis.

The term "alkyl" includes linear, branched, and cyclic structures and combinations thereof. Thus, the term includes methyl, ethyl, propyl, isopropyl, butyl, sec- and tert-butyl, cyclopropyl, cyclobutyl, cyclopentyl, 2-methylcyclopropyl, and the like. Lower alkyl is $C_1$-$C_6$ alkyl. Lower alkenyl is $C_2$-$C_6$ alkenyl of a linear, branched, or cyclic configuration and combinations thereof.

Unless otherwise indicated, it is intended that the definitions of any substituent (e.g., $R^1$ $R^2$, Z, etc.) in a particular molecule be independent of its definitions elsewhere in the molecule. Thus, $NR^4R^4$ represents NHH, NHCH$_3$, NHCH$_2$CH$_3$, N(CH$_3$)$_2$, etc.

Some of the compounds described herein contain one or more centers of asymmetry and may thus give rise to enantiomers, diastereoisomers, and other steroisomeric forms. The present invention is meant to include all such possible stereoisomers as well as their racemic and optically pure forms optically active (R) and (S) isomers may be prepared using chiral synthons, chiral reagents, or resolved using conventional techniques. When the compounds described herein contain olefinic double bonds, it is intended to include both E and Z geometric isomers.

The materials upon which the combinatorial syntheses of this invention are performed are referred to herein interchangeably as beads, solid surfaces, (solid) substrates, particles, supports, etc. These terms are intended to include:

a) solid supports such as beads, pellets, disks, capillaries, hollow fibers, needles, solid fibers, cellulose beads, pore-glass beads, silica gels, polystyrene beads optionally cross-linked with divinylbenzene, grafted co-poly beads, poly-acrylamide beads, latex beads, dimethylacrylamide beads optionally cross-linked with N,N'-bis-acryloyl ethylene diamine, glass particles coated with a hydrophobic polymer, etc., i.e., a material having a rigid or semi-rigid surface; and b) soluble supports such as low molecular weight non-cross-linked polystyrene.

These materials must contain functionalities or must be able to be functionalized such that identifiers or product intermediates may be attached to them.

In addition, the following abbreviations have the indicated meanings:

AcOH=acetic acid
BSA=bis(trimethylsilyl)acetamide
CAN=cerium (iv) ammonium nitrate
DEAD=diethylazodicarboxylate
DCM=dichloromethane
DIC=diisopropylcarbodiimide
DMF=N,N-dimethylformamide
Fmoc=9-fluorenylmethoxycarbonyl
HOBt=1-hydroxybenzotriazole
PhMe=toluene
r.t.=room temperature
TFA=trifluoroacetic acid
THF=tetrahydrofuran The subject invention concerns the production of libraries of products, i.e. compounds, where the individual products or compounds present in the libraries may be physically separated from one another and may be screened for a characteristic of interest either bound to, or detached from, a solid support. By having serial syntheses, where at each stage of a synthesis each of the individual intermediates is treated in a variety of ways, a very large number of products is produced, each of which is present in a small amount, frequently less than 100 pmol, more frequently less than 10 nmol. Because of the small quantity of final product or compound so produced, identifying these products by isolating and structurally elucidating the products would generally not be feasible. Moreover, in sequential synthesis involving other than the addition of similar units, the analysis would be arduous if not impossible using the amount of product typically available. However, by associating each choice or combination of choices (e.g., "add reagent A" or "add reagent A, then reagent B, and heat to 100° C. for 2 hrs.") of the serial synthesis with a combination of identifiers which define the choice of variables such as reactant, reagent, reaction conditions, or a combination of these, one can use the identifiers to define the reaction history of each definable and separable substrate. The analysis of tags detached from the identifiers allows for ready identification of the reaction history, at picomolar or lower concentrations, e.g. femtomolar or less. One can determine a characteristic of a product of a synthesis, usually a chemical or biological characteristic by various screening techniques, and then identify the reaction history and thereby the structure of that product, which has the desired characteristic, by virtue of the tags associated with the product.

The use of the instant multiple tag system avoids the necessity of carrying out a complicated cosynthesis which reduces yields and requires multiple protecting groups, and avoids the necessity of using sequencable tags which are necessarily chemically labile. Both the necessity of multiple protecting groups and the intrinsic instability of all known sequencable tagging molecules (i.e., nucleic acid or peptide oligomers) severely limit the chemistry which may be used in the synthesis of the library element or ligand.

Moreover, the use of a binary, or higher order, multiple tag system reduces enormously the number of tags necessary to encode the reagent/reactant choice in any stage in a synthesis. For example, if a particular synthetic stage could be carried with 125 different choices for reagent, the binary system would require only 7 tags. This can make the difference between a practical encoding system and an impractical one, because it may not be feasible to obtain and use the large number of distinguishable tags required by other systems. With the binary system of the invention, 30 distinguishable tags are available and are sufficient to encode $>10^9$ different syntheses.

Importantly, the present method employs tags which are detachable from a ligand or compound synthesized also for the purpose of decoding. Such detachability also allows the tags to be distinguished on more than one basis; in particular, they can be separated (e.g., on the basis of chromatographic retention time) and then analyzed (e.g., a second basis is a spectral property such as mass spectroscopy m/e, or electrophoricity). Having multiple bases for distinction allows the encoding of large amounts of information with a small number of tags.

Detachment further allows tags to be detected at very low levels, because they can be removed from the support matrix on which the synthesis is effected and from the ligand synthesized, the presence of either of which could provide spurious background signals, e.g. by quenching fluorescence or the like.

Detachable tags are also amenable to rapid analysis by automated sampling systems, and allow for selective derivatization for detection via functional groups, eliminating any incompatibility between the detection moiety and the reaction conditions used in the synthesis.

Inherent in any tagging scheme is the requirement that the chemical characteristics of the tags and the chemical stages for their incorporation be compatible with the characteristics of the ligand and the stages in their synthesis, and vice versa. The advantage of tags that are generally unreactive, as exemplified hereinafter by the substituted-aryloxypolymethylene moieties, is a greater range of chemical transformations and chemical functionality that can be employed in synthesis of the ligands.

A further advantage of the chemically stable tags of this invention is their compatibility with a greater variety of rapid, convenient methods of separation and analysis, such as gas chromatography and mass spectrometry. Moreover, the organic tags of this inventions generally do not specifically interact with biological receptors. Thus, these tags will generally not give spurious results in biological assays and will generally not be modified by enzymes or other biological molecules.

Finally, the chemical stability of the present tags allows them to be detached by a wide variety of methods which improves sensitivity in their analysis as described above.

Thus, this invention provides methods and compositions for encoded combinatorial synthesis whereby at each stage of the synthesis one or more identifiers are provided which encode an event associated with a particle stage in the synthesis of a compound on a support or particle. This event comprises the choice of reactant and/or reaction conditions at that stage of the reactions where each such stage may involve one or more reactants which are the same or different under the same or different conditions, e.g. partial reactions, multiple additions, rate of addition, differing combinations of reagents, etc. In addition, groups of particles may be sequestered from other groups of particles and subjected to a different series of events at any time during the course of the sequential synthesis.

By providing N identifiers, each having M distinguishable states, $M^N$ different syntheses can be uniquely defined. In the case of M=2 where the two states could be the presence or absence of identifier, the synthesis would thus be defined by a base 2 or binary code. In the case of M=3 where the three states could be the presence of an identifier at two distinguishable concentrations or its absence, the synthesis would be defined by a base 3 code. Herein, such base M codes where M>2 are termed higher order codes. The advantage of higher order codes over a binary code is that fewer identifiers are required to encode the same quantity of information about the synthesis. The products which are produced will be defined as resulting from a serial synthesis. At each stage in the synthesis, there is available a plurality of reactants and/or reagents and/or conditions, which result in a feature of the product in relation to an identifiable and usually separable entity, e.g. tag. In referring to reactants and reagents, it is intended that the reactant, for the most part, becomes incorporated into the product, e.g. an amino acid, nucleotide, nucleophile, electrophile, diene, alkylating or acylating agent, diamine, or any other synthon, etc. while a reagent may or may not become incorporated into the product, e.g. base, acid, heat, oxidizing or reducing agent, while both will be included under the term "agent". The synthesis may involve individual reactants which become incorporated into the product. Alternatively, a stage may involve one or more reactions which result in a modification of a reaction intermediate. In many cases, combinations of these possibilities will be involved.

Using a base 2 or binary code (M=2) and three identifiers (N=3), as many as 8 ($2^3$) agents for a given stage in a synthesis may be encoded. If the three identifiers are represented as T1, T2, and T3 and the presence or absence of each identifier is represented as a '0' or '1' respectively, then eight different agents could be represented in a binary code as follows:

|         | Agent 1 | Agent 2 | Agent 3 | Agent 4 |
|---------|---------|---------|---------|---------|
| T1,T2,T3 | 0,0,0   | 1,0,0   | 0,1,0   | 1,1,0   |
|         | Agent 5 | Agent 6 | Agent 7 | Agent 8 |
| T1,T2,T3 | 0,0,1   | 1,0,1   | 0,1,1   | 1,1,1   |

Similarly, even more information about the synthesis may be encoded by more identifiers. For example, 9 identifiers (N=3) and a base 2 code (M=2) would allow up to $2^9$ or 512 different agent choices to be encoded. Using a base 3 code (M=3) and three identifiers (N=3) would allow as many as 27 ($3^3$) agent choices to be encoded. If the three identifiers are represented as T1, T2 and T3, and the absence of an identifier is represented as a '0', its presence at a quantity of ~0.5 pmol/bead as a '1', and its presence at a quantity of ~1.0 pmol/bead as a '2', then the 27 different agents could be represented by three identifiers in base 3 code as:

|         | Agent 1 | Agent 2 | Agent 3 | Agent 4 |
|---------|---------|---------|---------|---------|
| T1,T2,T3 | 0,0,0   | 1,0,0   | 2,0,0   | 0,1,0   |
|         | Agent 5 | Agent 6 | . . .   | Agent 27 |
| T1,T2,T3 | 1,1,0   | 2,1,0   | . . .   | 2,2,2   |

To make such higher order encoding schemes practical, one additional identifier at a given quantity (e.g., ~1.0 pmol/bead) would be added to all members of the library to provide a standard against which the quantities of all identifiers would be measured. The quantities of the identifiers could be measured by gas chromatography or HPLC with a variety of detection methods. In the case of HPLC, quantities could be conveniently measured by scintillation counting if the identifiers were radioactively labeled by different quantities of a radionuclide such as tritium ($^3H$). It would be particularly convenient to carry out the quantitation by measuring the $^3H$-to-$^{14}C$ ratio, thus using $^{14}C$ as a standard. In this way, as many as ten quantities of $^3H$ could be distinguished to create a base 10 or decimal code (M=10) which could encode enormous amounts of information with very few identifiers.

Products and Synthetic Strategies

For the most part, the products of the method of this invention will be organic compounds where the serial synthesis will involve the addition or removal of chemical units, reactions involving the modification or introduction of one or more functionalities, ring openings, ring closings, etc. Chemical units can take many forms, both naturally-occurring and synthetic, such as nucleophiles, electrophiles, dienes, alkylating or acylating agents, diamines, nucleotides, amino acids, sugars, lipids, or derivatives thereof, organic monomers, synthons, and combinations thereof. Alternatively, reactions may be involved which result in alkylation, acylation, nitration, halogenation, oxidation, reduction, hydrolysis, substitution, elimination, addition, and the like. This process can produce non-oligomers, oligomers, or combinations thereof in extremely small amounts, where the reaction history, and composition in appropriate cases, can be defined by the present tags. Non-oligomers include a wide variety of organic molecules, e.g. heterocyclics, aromatics, alicyclics, aliphatics and combinations thereof, comprising steroids, antibiotics, enzyme inhibitors, ligands, hormones, drugs, alkaloids, opioids, terpenes, porphyrins, toxins, catalysts, as well as combinations thereof. Oligomers include oligopeptides, oligonucleotides, oligosaccharides, polylipids, polyesters, polyamides, polyurethanes, polyureas, polyethers, poly (phosphorus derivatives) e.g. phosphates, phosphonates, phosphoramides, phosphonamides, phosphites, phosphinamides, etc., poly (sulfur derivatives) e.g. sulfones, sulfonates, sulfites, sulfonamides, sulfenamides, etc., where for the phosphorous and sulfur derivatives the indicated heteroatom for the most part will be bonded to C, H, N, O or S, and combinations thereof.

Reactions may involve modifications at a variety of random sites of a central core molecular structure or modifications at a specific site. For example, one may brominate a polycyclic compound, where bromination may occur at a plurality of sites or use a brominating agent which will be specific for a particular site, e.g., N-bromosuccinide. For the most part, reactions will involve single sites or equivalent sites, for example, one of two hydroxyl groups of a glycol.

For the most part, the subject synthesis will have at least two stages where other than bifunctional compounds are attached using the same linking functionality, e.g. amino acids and amide bonds, nucleotides and phosphate ester bonds, or mimetic compounds thereof, e.g., aminoisocyanates and urea bonds.

The methods of the invention permit variation in reaction at each stage, depending on the choice of agents and conditions involved. Thus, for amino acids, one may have up to 20 amino acids involved using the common naturally-encoded amino acids and a much wider choice, if one wishes to use other amino acids, such as D-amino acids, amino acids having the amino group at other than the α-position, amino acids having different substituents on the side chain or substituents on the amino group, and the like. For the different nucleic acids, there will usually be up to 4 natural nucleic acids used for either DNA or RNA and a much larger number is available if one does not choose to use those particular nucleic acids. For the sugars and lipids, there are a very large number of different compounds, which compounds may be further increased by various substitutions, where all of these compounds may be used in the synthesis. For individual organic compounds the choice may be astronomically large. In addition, one may have mimetic analogs, where ureas, urethanes, carbonylmethylene groups, and the like may substitute for the peptide linkage; various organic and inorganic groups may substitute for the phosphate linkage; and nitrogen or sulfur may substitute for oxygen in an ether linkage or vice versa.

The synthetic strategies will vary with the nature of the group of products one wishes to produce. Thus, the strategy must take into consideration the ability to stage-wise change the nature of the product, while allowing for retention of the results of the previous stages and anticipating needs for the future stages. Where the various units are of the same family, such as nucleotides, amino acids and sugars, the synthetic strategies are relatively well-established and frequently conventional chemistry will be available. Thus, for nucleotides, phosphoramidite or phosphite chemistries may be employed; for oligopeptides, Fmoc or Boc chemistries may be employed where conventional protective groups are used; for sugars, the strategies may be less conventional, but a large number of protective groups, reactive functionalities, and conditions have been established for the synthesis of polysaccharides. For other types of chemistries, one will look to the nature of the individual unit and either synthetic opportunities will be known or will be devised, as appropriate.

In some instances, one may wish to have the same or different blocks introduced at the same or different stages. For example, one may wish to have a common peptide functional unit, e.g. the fibronectin binding unit (RGDS), a polysaccharide, e.g. Le$^x$, an organic group, e.g. a lactam, lactone, benzene ring, olefin, glycol, thioether, etc. introduced during the synthesis. In this manner one may achieve a molecular context into which the variation is introduced. These situations may involve only a few stages having the plurality of choices, where a large number of products are produced in relation to a particular functional entity. This could have particular application where one is interested in a large number of derivatives related to a core molecule or unit known to have a characteristic of interest.

In developing synthetic strategies, one can provide for batch synthesis of a few compounds which would be prepared during the course of the combinatorial synthesis. By taking extreme examples, for example, syntheses which might involve steric hindrance, charge and/or dipole interactions, alternative reaction pathways, or the like, one can optimize conditions to provide for enhanced yields of compounds which might not otherwise be formed or be formed only in low yield. In this manner, one may allow for a variety of reaction conditions during the combinatorial synthesis, involving differences in solvent, temperatures, times, concentrations, and the like. Furthermore, one may use the batch syntheses, which will provide much higher concentrations of particular products than the combinatorial synthesis, to develop assays to characterize the activity of the compounds.

Supports: Attachment and Detachment

The synthetic protocol requires that one provide for a plurality of different reactions involving different reactants resulting in a plurality of different intermediates at each stage of the synthesis. While other techniques are available, this can be achieved most conveniently by employing small definable solid substrates, commercially available as beads, which can be readily mixed, separated, and serve as a solid substrate for the sequential synthesis. The solid substrates may be solid, porous, deformable or hard, and have any convenient structure and shape. In some instances, magnetic or fluorescent beads may be useful. The beads will generally be at least 10–2000 μm, usually at least 20–500 μm, more usually at least 50–250 μm in diameter.

Any convenient composition can be used for the particles or beads, which bead composition will maintain its mechanical integrity during the various process stages, can be functionalized, has functional groups or allows for reaction with an active species, allows for the serial synthesis as well as attachment of the identifiers, can be readily mixed and separated, and will allow for convenient detachment of the tags and products. Beads which may be employed include cellulose beads, pore-glass beads, silica gel, polystyrene beads, particularly polystyrene beads cross-linked with divinylbenzene, grafted co-polymer beads such as polyethyleneglycol/polystyrene, polyacrylamide beads, latex beads, dimethylacrylamide beads, particularly cross-linked with N,N'-bis-acryloyl ethylene diamine and comprising N-t-butoxycarbonyl-β-alanyl-N'-acryloyl hexamethylene diamine, composites, such as glass particles coated with a hydrophobic polymer such as cross-linked polystyrene or a fluorinated ethylene polymer to which is grafted linear polystyrene; and the like. General reviews of useful solid supports (particles) that include a covalently-linked reactive functionality may be found in Atherton, et al., *Prospectives in Peptide Chemistry*, Karger, 101–117 (1981); Amamath, et al., Chem. Rev. 77: 183–217 (1977); and Fridkin, *The Peptides*, Vol. 2, Chapter 3, Academic Press, Inc., (1979), pp. 333–363.

Depending upon the nature of the synthetic procedure or the assay of the final product, one or another bead may be more or less desirable. While beads are especially convenient, other solid supports may also find use, such as capillaries, hollow fibers, needles, solid fibers, etc., where the size of the solid support allows for the desired variation in reaction histories.

Depending upon the nature of the synthesis, the beads may be functionalized in a variety of ways to allow for attachment of the initial reactant. These may be linked through a non-labile linkage such as an ester bond, amide bond, amine bond, ether bond, or through a sulfur, silicon, or carbon atom, depending upon whether one wishes to be able to remove the product from the bead. Conveniently, the bond to the bead may be permanent, but a linker between the bead and the product may be provided which is cleavable such as exemplified in Table 1. Two or more different linkages may be employed to allow for differential release of tags and/or products.

Depending upon the nature of the linking group bound to the particle, reactive functionalities on the bead may not be necessary where the manner of linking allows for insertion into single or double bonds, such as is available with carbenes and nitrenes or other highly-reactive species. In this case, the cleavable linkage will be provided in the linking group which joins the product or the tag to the bead.

Desirably, when the product is permanently attached, the link to the bead will be extended, so that the bead will not sterically interfere with the binding of the product during screening. Various links may be employed, particular hydrophilic links, such as polyethyleneoxy, saccharide, polyol, esters, amides, combinations thereof, and the like.

Functionalities present on the bead may include hydroxy, carboxy, iminohalide, amino, thio, active halogen (Cl or Br) or pseudohalogen (e.g., —$CF_3$, —CN, etc.), carbonyl, silyl, tosyl, mesylates, brosylates, triflates or the like. In selecting the functionality, some consideration should be given to the fact that the identifiers will usually also become bound to the bead. Consideration will include whether the same or a different functionality should be associated with the product and the identifier, as well as whether the two functionalities will be compatible with the product or identifier attachment and tag detachment stages, as appropriate. Different linking groups may be employed for the product, so that a specific quantity of the product may be selectively released. In some instances the particle may have protected functionalities which may be partially or wholly deprotected prior to each stage, and in the latter case, reprotected. For example, amino may be protected with a carbobenzoxy group as in polypeptide synthesis, hydroxy with a benzyl ether, etc.

Where detachment of the product is desired, there are numerous functionalities and reactants which may be used. Conveniently, ethers may be used, where substituted benzyl ether or derivatives thereof, e.g. benzhydryl ether, indanyl ether, etc. may be cleaved by acidic or mild reductive conditions. Alternatively, one may employ β-elimination, where a mild base may serve to release the product. Acetals, including the thio analogs thereof, may be employed, where mild acid, particularly in the presence of a capturing carbonyl compound, may serve. By combining formaldehyde, HCl and an alcohol moiety, an α-chloroether is formed. This may then be coupled with an hydroxy functionality on the bead to form the acetal. Various photolabile linkages may be employed, such as o-nitrobenzyl, 7-nitroindanyl, 2-nitrobenzhydryl ethers or esters, etc. Esters and amides may serve as linkers, where half-acid esters or amides are formed, particularly with cyclic anhydrides, followed by reaction with hydroxyl or amino functionalities on the bead, using a coupling agent such as a carbodiimide. Peptides may be used as linkers, where the sequence is subject to enzymatic hydrolysis, particularly where the enzyme recognizes a specific sequence. Carbonates and carbamates may be prepared using carbonic acid derivatives, e.g. phosgene, carbonyl diimidazole, etc. and a mild base. The link may be cleaved using acid, base or a strong reductant, e.g., $LiAlH_4$, particularly for the carbonate esters. For a list of cleavable linkages, see, for example, Greene and Wuts, *Protective Groups in Organic Synthesis*, 2nd ed. Wiley, 1991. The versatility of the various systems that have been developed allows for broad variation in the conditions for attachment of products and identifiers and differential detachment of products and tags, as desired.

The following table indicates various illustrative linking units (i.e., $F^2$ in Formula I) and the manner in which they may be cleaved:

TABLE 1

Various illustrative linking units and the manner in which they may be cleaved.

| Linking Group | Cleavage Reagent |
|---|---|
| silyl | fluoride or acid |
| A | hν |
| B | $Ce(NH_4)_2(NO_3)_6$ |
| —$NCO_2(L)$* | $OH^-$, $H^+$, or $LiAlH_4$ |
| C | $O_3$, $OsO_4/IO_4^-$, or $KMnO_4$ |
| D | 1) $O_2$ or $Br_2$, MeOH |
|  | 2) $H_3O^+$ |
| —Si-(L) | oxidation, $H^+$, $Br_2$, $Cl_2$, etc. |
| E | $H_3O^+$ |
| F | $H_3O^+$ |
| G | $F^-$ or $H^+$ |
| H | base, $OH^-$ |
| x = keto, ester, amide, $NO_2$, sulfide, sulfoxide, sulfone, and related electron withdrawing groups | |
| I | $H_3O^+$ or reduction (e.g. $Li/NH_3$) |
| J | $(\phi_3P)_3RhCl(H)$ |
| K | Li, Mg, or BuLi |
| M | $Hg^{+2}$ |
| N | Zn or Mg |
| x = halogen or pseudohalogen | |
| O | oxidation (e.g. $Pb(OAc)_4$ or $H_5IO_6$) |
| P | base |
| x = electron withdrawing group | |

*(L) shows the point of attachment of the tag or product.

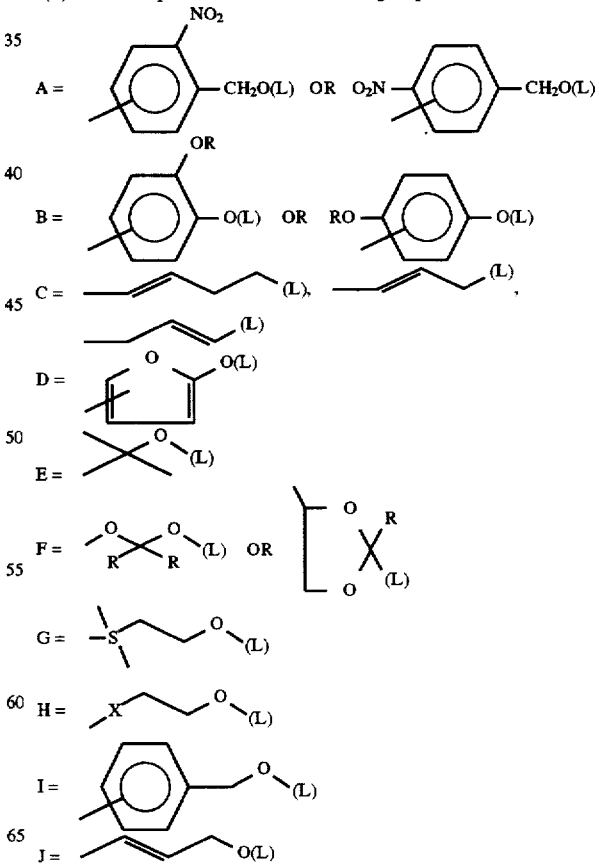

TABLE 1-continued

Various illustrative linking units and the
manner in which they may be cleaved.

| Linking Group | Cleavage Reagent |
|---|---|

K = [structure: bromobenzene with methyl and O—(L)]

M = [structure: S—O(L) with X]

N = [structure with O(L)]

O = [structure with OH and O(L)]

P = [structure with OH and X(L)]; [structure with OH and (L), X OR]

[structure: (L), OH, X]

L is the tag or product either directly bonded to the indicated atom or indirectly bonded through a linking group such as C(O)O, which linking group may provide a convenient functionality.

R is H or lower alkyl.

Linker

The choice of linker for the ligand will be part of the synthetic strategy, since the linking group may result in a residual functionality on the product. It will usually be difficult, but feasible, to further modify the product after detachment from the bead. In designing the synthetic strategy, one can use a functionality to be retained in the product as the point of attachment for the linking group. Alternatively, when permitted by the nature of the product, one could use a cleavage or detachment method which removes the linking functionality, e.g., an arylthioether or silyl with a metal hydride or acid. Since in many cases the synthetic strategy will be able to include a functionalized site for linking, the functionality can be taken advantage of in choosing the linking group. In some instances it may be desirable to have different functionalities at the site of linking the product to the support, which may necessitate using different modes of linking, which modes must accommodate either the same detachment method or different detachment methods which may be carried out concurrently or consecutively, e.g., irradiation with light and acid hydrolysis.

Of particular interest for binding the identifiers to the particle are carbenes and nitrenes which can insert between a carbon and hydrogen atom to form a covalent bond, or into an olefinic bond to form a cyclopropane (in the case of carbene) or an aziridine (in the case of nitrene).

With carbene or nitrene linking groups various substituted benzenes may be used, where the benzene is substituted with a group capable of providing a carbene: $CHN_2$, $COCHN_2$, $SO_2CHN_2$; or nitrene: $N_3$, $NO_2$, NO, $SO_2N_3$. The carbenes may be generated from diazoalkane derivatives by photolysis, thermolysis, or by treatment with low valent transition metal species, e.g., $Rh(OAc)_2$. The nitrene may be generated by photolysis or thermolysis from azides; and from nitro, nitroso and azides by using tervalent phosphorus compounds or low valent transition metals.

A group of linker moieties ($F^1$—$F^2$—) of particular interest include 2-nitro-4-carboxybenzyloxy, 2-nitro-4-diazoacetylbenzyloxy, 4 or 5 azidomethylcarbonyl-2-methoxyphenoxy, and 2-methoxy-4-, or 5-carboxyphenoxy moieties.

Illustrative compounds where T represents the tag, Z represents a carbene or nitrene precursor or a carboxy group, and R is H or lower alkyl are as follows. For photochemical tag detachment (e.g., with ultraviolet light at about 350 nm): T 3-Z-2-nitrobenzyl ether, T 4-Z-2-nitrobenzyl ether, T 5-Z-2-nitrobenzyl ether, T 6-Z-2-nitrobenzyl ether, T 2-Z-4-nitrobenzyl ether, T 3-Z-4-nitrobenzyl ether, T 3-Z-2-nitrobenzyl carbonate, T 4-Z-2-nitrobenzyl carbonate, T 5-Z-2-nitrobenzyl carbonate, T 6-Z-2-nitrobenzyl carbonate, T 2-Z-4-nitrobenzyl carbonate, and T 3-Z-4-nitrobenzyl carbonate. For oxidative detachment (e.g., using ceric ammonium nitrate): 1-OT-2-OR-3-Z-benzene, 1-OT-2-OR-4-Z-benzene, 1-OT-2-OR-5-Z-benzene, 1-OT-2-OR-6-Z-benzene, 1-OT-4-OR-2-Z-benzene, and 1-OT-4-OR-3-Z-benzene. For reductive or alkylative detachment (e.g. with lithium/ammonia or methyl iodide): T (2-Z-phenyl) thioether, T (3-Z-phenyl)thioether, and T (4-Z-phenyl) thioether. For desilylative detachment (e.g., using tetrabutyl ammonium fluoride or acid): T dialkyl-(2-Z-phenyl)silyl ether, T dialkyl-(3-Z-phenyl)silyl ether, T dialkyl-(4-Z-phenyl)silyl ether, T-dialkyl-(2-Z-phenyl)silane, T-dialkyl-(3-Z-phenyl)silane, and T-dialkyl-(4-Z-phenyl)silane.

Combinatorial synthesis

The synthesis will usually involve stages involving at least 2 choices, frequently at least 4 choices, and may involve 10 choices or more. Generally, the number of choices per stage will not exceed about 100, more usually not exceed about 50. The number of stages will usually be at least about 3, more usually at least about 4, frequently at least 5, and not more than about 30, more usually not more than about 25, preferably not more than about 20, more preferably not more than about 10, frequently not more than about 8.

The number of choices and stages will usually result in at least a number of compounds which allows for a sufficient variety to provide a reasonable likelihood that at least one compound will have the characteristic of interest. The subject methodology allows for producing greater than 25,000 compounds, usually greater than 50,000 compounds, preferably greater than 200,000 compounds, and a million or more may be produced. This will usually mean at least 20 compounds but may be $10^6$ or more.

In some syntheses, a stage may only involve one or two choices, but this situation will usually be limited in relation to the number of compounds one wishes to produce and the particular synthetic strategy. In many of the strategies, the restricted number of choices, i.e., fewer than 5 choices, more usually 2 or fewer choices, will be limited to the greater of 40% of the total number of stages or about 2 stages in the sequential synthesis, more usually limited to 20% of the total number of stages.

Reaction Procedure

In carrying out the synthesis, one may initially begin with a number of beads, usually at least $10^3$, more usually at least $10^4$, and desirably at least $10^5$, while generally not exceeding at least $10^{15}$, more usually not exceeding at least $10^{10}$. Depending upon the number of choices in the first stage, one will divide up the particles accordingly into as many containers. One can use microtiter well plates, individual containers, columns, gels, Terasaki plates, flasks, Merrifield synthesis vessels, etc. The particles will usually be divided up into groups of at least one particle each, usually a plurality of particles, generally 1000 or more, and may be $10^5$ or more depending on the total number of particles and choices involved in the stage.

One would then add the appropriate agents to each of the individual containers to process them in stages and add the identifiers which encode the reagent and stage. Each stage would provide the desired reaction. Once the reaction(s) is complete, one may wish to wash the beads free of any reagent, followed by combining all of the beads into a single mixture and then separating the beads according to the number of choices for the next stage. This procedure of dividing beads, followed by the tagging and synthesis stages (or vice versa), and then recombining beads is iterated until the combinatorial synthesis is completed.

In some instances, the same reaction may be carried out in 2 or more containers to enhance the proportion of product having a particular reaction at a particular stage as compared to the other choices. In other instances, one or more of the stages may involve a portion of the beads being set aside and undergoing no reaction, so as to enhance the variability associated with the final product. In other situations, batches may be taken along different synthetic pathways.

In order to record or encode the synthesis history on the beads, in one embodiment $\underline{C}$ or $\underline{C'}$ or both may be present and subsequent attachment of $\underline{C}$ excludes the presence of $\underline{C'}$ at each stage one would tag the beads associated with each choice and stage with their own unique combination of identifiers. Alternately one may use a single tag to record or encode this synthesis history. Depending on the chemistries involved, this tagging may be done prior to, after, or concomitantly with the reactions which comprise each choice. Further, as a control, sample beads may be picked at any stage and a portion of their tags cleaved off and decoded to verify that the correct tags are bound to the sample beads.

As indicated previously, in some instances, portions of the particles will be segregated into subsets, where each of the subsets would then undergo a different reaction series. At any time, the portions may be recombined into a single mixture for subsequent reaction. For example, if at one stage one introduces unsaturation, one could provide two subsets, where in one subset the unsaturation is reduced, while in the other subset the unsaturation is epoxidized. These two subsets could then be subjected to different reaction series.

After synthesis of the products is complete, they are screened for a desired property either after detachment of the ligand from the bead or while still attached. In the latter case, beads, for example, may be incubated in aqueous buffer with mouse monoclonal antibody Y. After incubation and washing, the beads are incubated with alkaline phosphatase-conjugated rabbit (or goat) polyclonal antibody directed against mouse antibodies. Using a fluorescent precipitation developing reagent, fluorescent beads with attached monoclonal antibody are identified and manually separated from the majority of clear, unstained beads. Alternatively, the fluorescent beads can be separated using a fluorescence-activated cell sorter, so long as the tags are retained on the bead under the conditions of sorting. Each selected fluorescent bead is subjected to a means for releasing at least some of the tags from the bead.

In instances where the synthesis does not involve the stagewise addition of like units, or where reaction byproducts are formed, there may be instances where there will be a plurality of compounds on a single bead or the structure of the active compound cannot be known from its reaction history. In accordance with the subject invention, by knowing the reaction history, one may repeat the synthesis on a larger scale so as to obtain a sufficient amount of the product(s) to isolate the product(s) and structurally identify the active compound.

The subject methodology may be illustrated using various reaction sequences. For example, barbiturates may be prepared by combining an aldehyde or ketone with an acetate ester to prepare a crotonate under Claisen conditions to provide an unsubstituted to tetrasubstituted crotonate. The crotonate may then be combined with a second acetate under Michael conditions, whereby a glutarate may be obtained having up to 6 substituents. The glutarate may then be combined with ammonia or monosubstituted amine to provide the barbiturate. By varying the aldehydes and ketones, the acetates and the amines, a great variety of barbiturates may be obtained. Where functionalities are present on one or more of the substituents, such as amino, carboxy, hydroxy, thiol, and the like, these groups may be protected or modified as desired.

In another example described by Bunin and Ellman, *J. Am. Chem. Soc.*, 114, 10997 (1992), benzodiazepines are produced. One begins the synthesis with different amino protected substituted 2-aminobenzophenones bound to individual particles through, for example a 4'-oxy group. To each different group of particles in different vessels, after deprotection, are added a different Fmoc-protected α-amino acid, either naturally occurring or synthetic, under conditions where a peptide bond is formed. After deprotection, internal cyclization is caused, followed by alkylation on nitrogen with an alkylating agent. In only three stages, a very large number of benzodiazepines may be prepared and the libraries screened for tranquilizing or other activity.

A wide variety of drug analogs may be produced, such as analogs of antihypertensive agents, e.g. enalapril; β-blockers, e.g. propanolol; antiulcer drugs ($H_2$-receptor antagonists) e.g. cimetidine and ranitidine; antifungal agents (cholesterol-demethylase inhibitors) e.g. isoconazole; anxiolytics, e.g. diazepam; analgesics, e.g. aspirin, phenacetamide, and fentanyl; antibiotics, e.g. vancomycin, penicillin and cephalosporin; antiinflammatories, e.g. cortisone; contraceptives, e.g. progestins; abortifacients, e.g. RU-456; antihistamines, e.g. chlorphenamine; antitussives, e.g. codeine; sedatives, e.g. barbitol; etc.

An illustrative synthesis of cimetidine analogs could involve hydroxymethylsubstituted histidines, and related heterocycles, where the remaining carbon atoms or nitrogen atoms could be further substituted or unsubstituted, α,ω-aminoalkylthiols, and substituted thioamidine esters, where the groups on nitrogen could be varied, such as nitro, cyano, hydroxy, alkyl, combinations thereof, and the like.

Identifier

The identifiers of this invention may be represented by the Formula I:

   I where $F^1$—$F^{2'}$ is a linker which allows for attachment to a support and detachment of the tag from a support; and $\underline{C}$—E—$\underline{C'}$ is the tag which is capable of detection and distinguishability;

E is a tag component which (a) allows for detection, such as an electrophoric group which can be analyzed by gas chromatography or mass spectroscopy or (b) allows for detection and for separation;

$\underline{C}$ and $\underline{C'}$ are tag components which allow for individually distinguishing one tag from all other tags, usually allowing for separation as a result of variable length or substitution, for example, varying the chromatographic retention time or the mass spectroscopy ratio m/e;

$F^2$ is a linking component capable of being selectively cleaved to release the tag component; and $F^1$ is a functional group which provided for attachment to the support; or $F^2$ is a bend when $F^1$ is a cleavable group such as OH or carboxy.

Although the identifiers of Formula I are typically added at each appropriate stage and choice during the combinatorial synthesis, the portion E can be added at the end of the syntheses either before or after cleavage (preferably photochemically or oxidatively) from the substrate. Specifically, where $\underline{C}$ contains OH, NHR$^4$, or SH, E can be attached to $\underline{C}$ prior to cleavage. Alternatively, if E is attached after cleavage, the point of attachment at $\underline{C}$ may be where F$^2$ was attached. This is exemplified in the scheme on the following page:

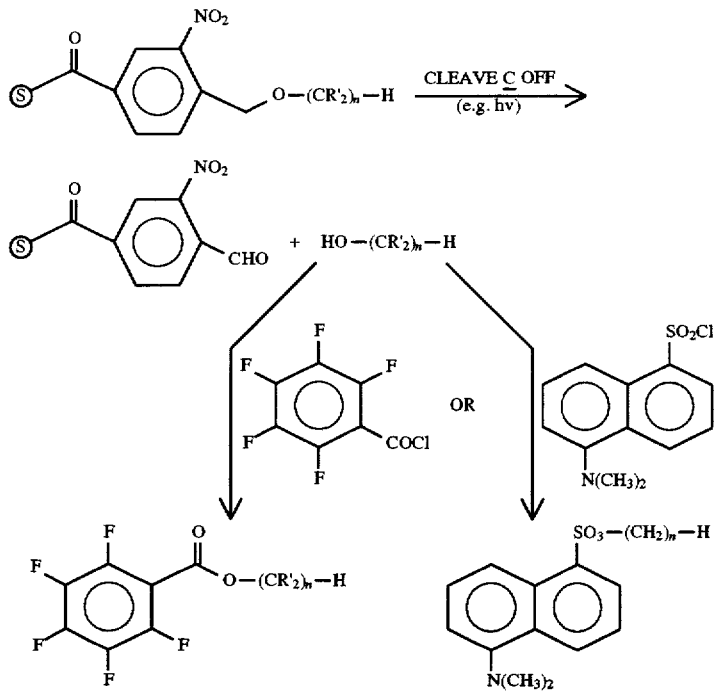

where

S=substrate and n=1–40

Attachment of the identifier to the substrate can be represented as follows:

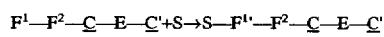

where F$^{1'}$—F$^2$—$\underline{C}$—E—$\underline{C}'$ represents the identifier residue attached to the substrate. For example, when the bead is functionalized with an aminomethyl group and F$^1$ is CO$_2$H, then F$^{1'}$ is —C(O)—; when the bead contains an unsaturated bond and F$^1$ is N$_2$CH—C(O)—, then F$^{1'}$ is =CH—C(O)— or —CH$_2$—C(O)—.

Of particular interest for use as identifiers are compounds of Formula I of the Formula Ia:

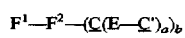

wherein:

F$^1$ is CO$_2$H, CH$_2$X, NR$^1$R$^1$, C(O)R$^1$, OH, CHN$_2$, SH, C(O)CHN$_2$, S(O$_2$)Cl, S(O$_2$)CHN$_2$, N$_3$, NO$_2$, NO, S(O$_2$)N$_3$, OC(O)X, C(O)X, NCO, or NCS;

F$^2$ is

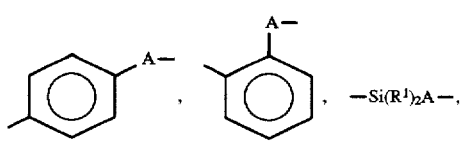

-continued

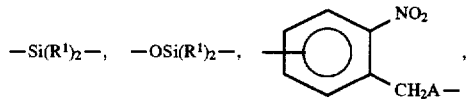

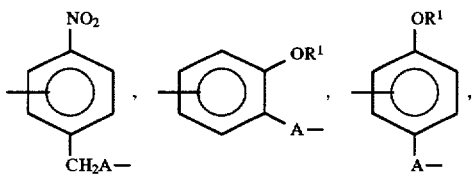

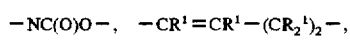

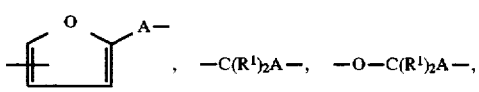

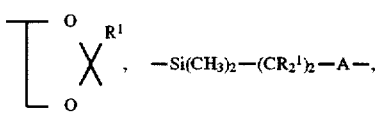

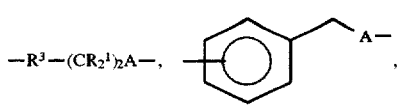

-continued

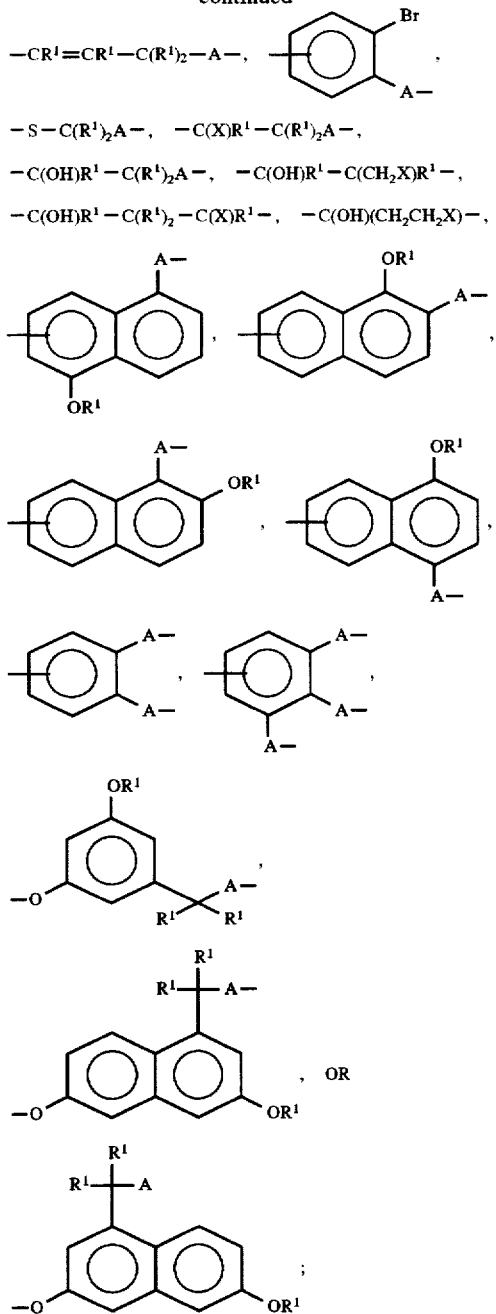

A is —O, —OC(O)O—, —OC(O)—, or —NHC(O)—;

$\underline{C}$ is a bond, $C_1$–$C_{20}$ alkylene optionally substituted by 1–40 F, Cl, Br, $C_1$–$C_6$ alkoxy, $NR^4R^4$, $OR^4$, or $NR^4$, or —[$(C(R^4)_2)_m$—Y—Z—Y—$(C(R^4)_2)_n$Y—Z—Y]$_p$—; with the proviso that the maximum number of carbon atoms in $\underline{C}$+$\underline{C}'$ is preferably 20;

$\underline{C}'$ is H; F; Cl; $C_1$–$C_{20}$ alkylene optionally substituted by 1–40 F, Cl, Br, $C_1$–$C_6$ alkoxy, $NR^4R^4$, $OR^4$, or $NR^4$, or —[$(C(R^4)_2)_m$—Y—Z—Y—$(C(R^4)_2)_n$Y—Z—Y]$_p$—;

E is $C_1$–$C_{10}$ alkyl substituted by 1–20 F, Cl or Br; or Q-aryl wherein the aryl is substituted by 1–7 F, Cl, $NO_2$, $SO_2R^5$, or substituted phenyl wherein the substituent is 1–5 F, Cl, $NO_2$, or $SO_2R^5$;

E—$\underline{C}'$ may be —H, —OH, or amino;

$R^1$ is H or $C_1$–$C_6$ alkyl;

$R^3$ is C=O, C(O)O, C(O)$NR^1$, S, SO, or $SO_2$;

$R^4$ is H or $C_1$–$C_6$ alkyl;

$R^5$ is $C_1$–$C_6$ alkyl;

a is 1–5;

b is 1–3;

m and n is each 0–20;

p is 1–7;

Q is a bond, O, S, $NR^4$, C=O, —C(O)$NR^5$, —$NR^5$C(O)—, —C(O)O—, or —OC(O)—;

X is a leaving group such as Br, Cl, triflate, mesylate, tosylate, or OC(O)$OR^5$;

Y is a bond, O, S, or $NR^4$;

Z is a bond; phenylene optionally substituted by 1–4 F, Cl, Br, $C_1$–$C_6$ alkyl, $C_1$–$C_6$ alkoxy, $C_1$–$C_6$ alkyl substituted by 1–13 F, Cl, or $C_1$–$C_6$ alkyloxy substituted by 1–13 F, Cl, or Br; $(C(R^4)_2)_{1-20}$; or $(CF_2)_{1-20}$; with the proviso that when Z is a bond one of its adjacent Y's is also a bond; and aryl is a mono- or bi-cyclic aromatic ring containing up to 10 carbon atoms and up to 2 heteroatoms selected from O, S, and N.

In the definitions of $F^2$ in Formula Ia, the left-hand bond as depicted attaches to $F^1$.

Also useful as identifiers are compounds of the Formula Ia':

$$F^1—(\underline{C}(E—\underline{C}')_a)_b \qquad \text{Ia'}$$

wherein:

$F^1$ is OH or COOH; and the remaining definitions are as in Formula Ia.

Preferred compounds of Formula Ia are those wherein;

$F^1$ is $CO_2H$, OH, $CHN_2$, C(O)$CHN_2$, C(O)X, NCS, or $CH_2X$:

$\underline{C}$ and $\underline{C}'$ is each independently $C_1$–$C_{20}$ alkylene unsubstituted or substituted by 1–40 F or Cl, or [O—$(CH_2)_{2-3}$]$_p$;

E is $C_1$–$C_{10}$ alkyl substituted by 1–20 F or Cl; Q-aryl where aryl is a bi-cyclic aromatic ring substituted by 1-7 F or Cl; or Q-phenyl substituted by 1-5 F, Cl, NO$_2$, or SO$_2$R$^5$; and Q is a bond, O, —NR$^5$C(O)—, or —OC(O)—.

Preferred compounds of Formula Ia are those wherein

—C(E—C'), is represented by —(CH$_2$)$_{3-15}$—(CF$_2$)$_{1-15}$F, —(CH$_2$)$_{3-15}$—(CCl$_2$)$_{1-15}$Cl, —(CH$_2$CH$_2$—O)$_{1-5}$—Ar, —(CH$_2$CH$_2$CH$_2$O)$_{1-5}$—Ar, or —(CH$_2$)$_{1-12}$—O—Ar;

wherein Ar is pentafluoro- pentachloro-, or pentabromophenyl, 2,3,5,6-tetrafluoro-4(2,3,4,5,6-pentafluorophenyl)phenyl, 2,4,6-trichlorophenyl, 2,4,5-trichlorophenyl, 2,6-dichloro-4-fluorophenyl, or 2,3,5,6-tetrafluorophenyl.

Other preferred compounds of Formula Ia are represented by the formulae:

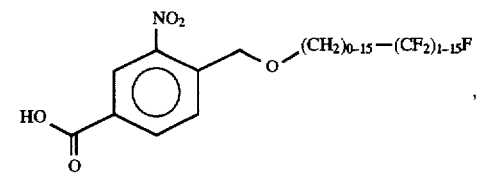

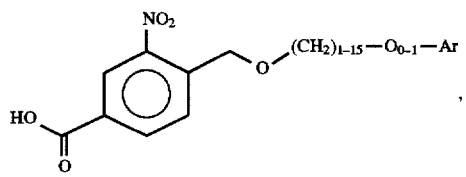

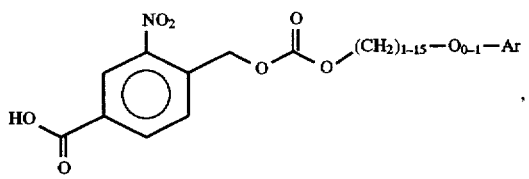

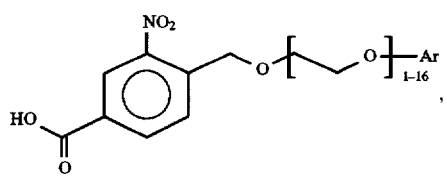

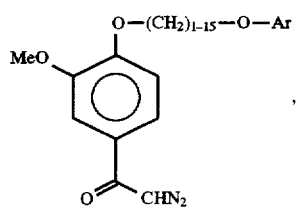

, OR

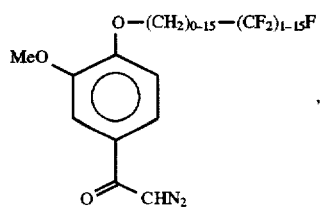

-continued

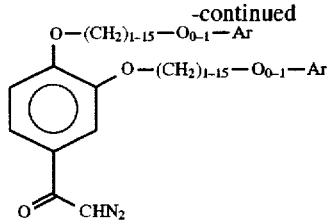

wherein Ar is pentafluoro- pentachloro-, or pentabromophenyl, 2,3,5,6-tetrafluoro-4(2,3,4,5,6-pentafluorophenyl)phenyl, 2,4,6-trichlorophenyl, 2,4,5-trichlorophenyl, 2,6-dichloro-4-fluorophenyl, or 2,3,5,6-tetrafluorophenyl.

Other preferred compounds of Formula Ia are those wherein E—C' is H, OH, or NH$_2$. Such compounds are particularly useful for reaction with an E at the end of the combinatorial synthesis, especially with an E detectable by fluorescence or electron capture, such as dansyl chloride or polyhalobenzoylhalide.

The compounds of Formula I can be prepared according to the following exemplary schemes or other means known to those skilled in the art.

SCHEME 1
Identifier Tag Preparation

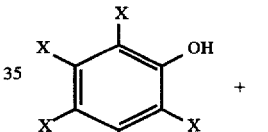

ELECTROPHORIC PHENOL,
ArOH
X = Cl OR F.

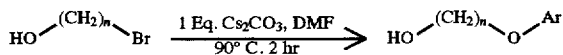

SCHEME 2
Identifiers With Photolytic Cleavage Linkers

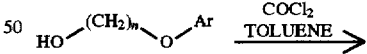

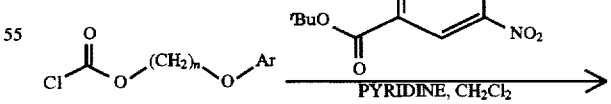

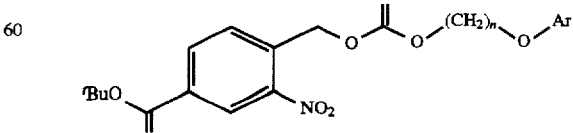

SCHEME 2
Identifiers With Photolytic Cleavage Linkers
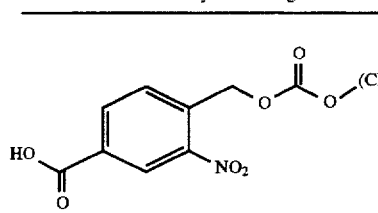
SCHEME 3
Identifiers With Oxidative Cleavage Linkers
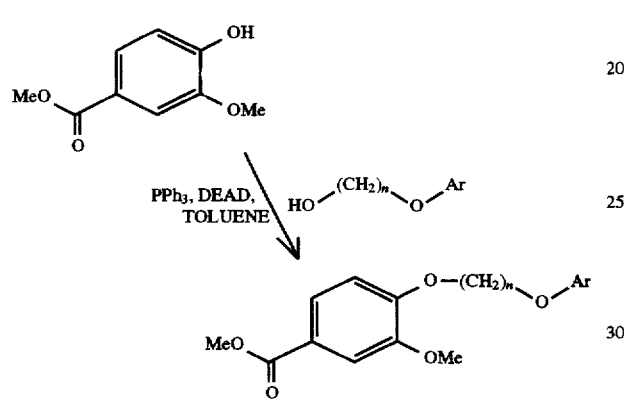
SCHEME 4
Identifiers With Alternative Oxidative Release Linkers
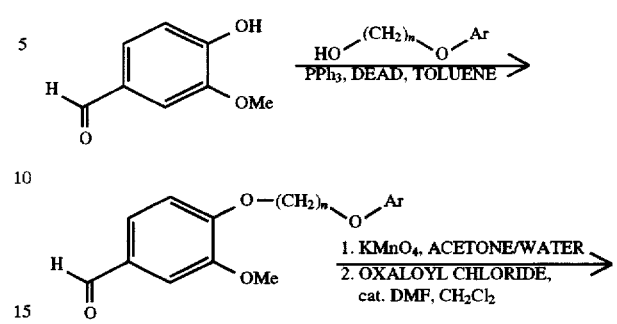
SCHEME 5
E—C' Tags
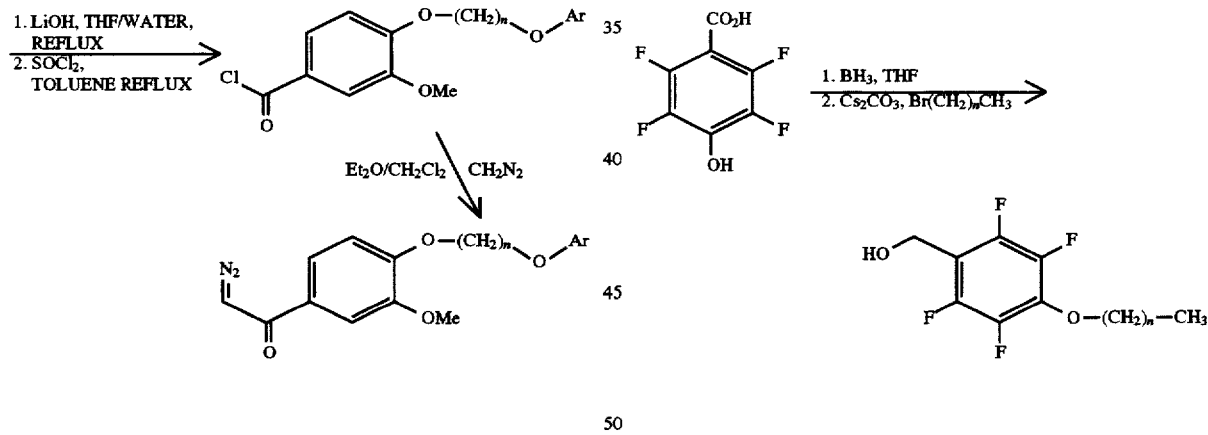
SCHEME 6
Identifiers With Photolytic Cleavage Linkers
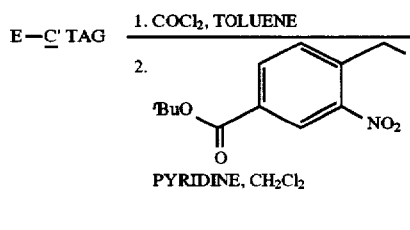

SCHEME 6
Identifiers With Photolytic Cleavage Linkers

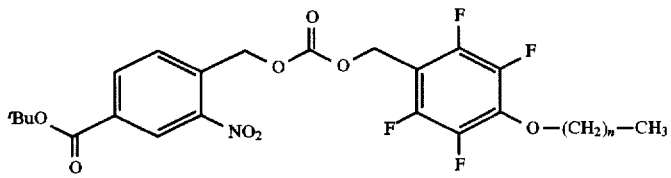

SCHEME 7
Identifiers With Oxidative Cleavage Linkers

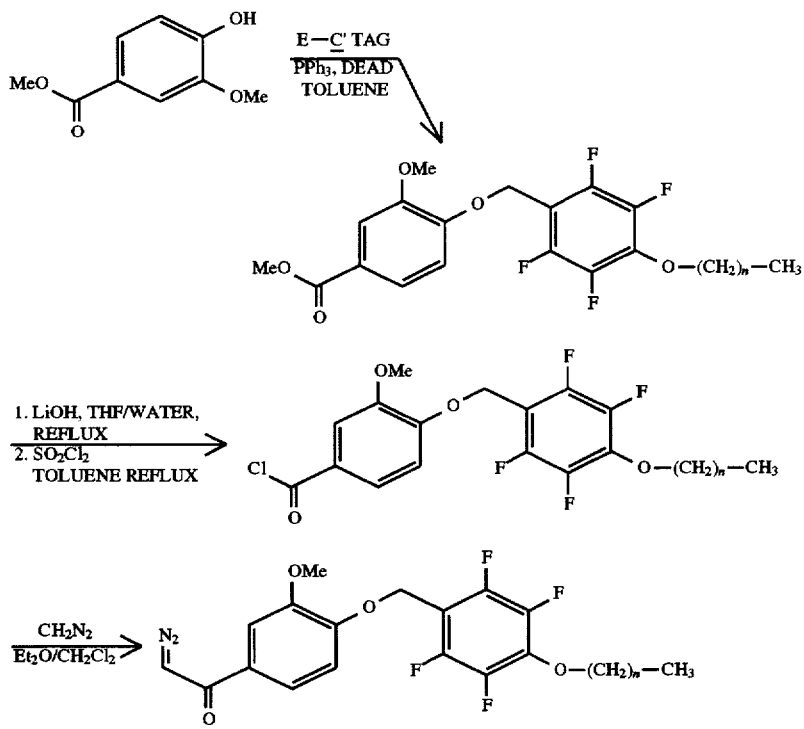

The identifier may comprise one or a plurality of identical tags. The identifiers will be individual chemical compound(s) which may be distinguished one from the other and will uniquely identify different choices and stages. In this manner, very large combinatorial libraries may be prepared with a relatively small number of identifiers, usually fewer than 50 tags.

During each stage, a combination of identifiers will be added, which defines the stage and choice. Each identifier will be bound, either covalently or non-covalently to the bead or to the product, usually the bead. Combinations of identifiers are used to provide a binary or other code at each stage, whereby the choice and stage may be defined. The combination of identifiers may include zero or only one identifier.

Tags

So far as the tags (C—E—C') are concerned, the tags which are employed will be characterized as follows: by being removable from the bead by means depending on $F^2$, preferably by photolysis or oxidation; by being individually differentiable, usually separable; by being stable under the synthetic conditions; by encoding both stage and choice so as to uniquely define the choice of agent used at each stage in the synthesis; desirably, there should be an easy way to identify the various tags with readily-available equipment which does not require sophisticated technical capabilities to operate; they should be relatively economical and provide a strong signal based on a relatively few molecules; and the tags should provide sufficient sensitivity to permit distinguishing the tags from the other components which may be present during the tag determinations.

The tags may be structurally related or unrelated, as in a homologous series, repetitive functional groups, related members of the Periodic Chart, different isotopes, combinations thereof, or the like. The tags may be used as elements of a binary code, so that one tag can define two choices, two tags can define four choices, three tags can define eight choices, five tags can define thirty-two choices, etc. Thus, at each stage of the synthesis, a relatively small number of tags can designate a much larger number of choices. The tags comprising the identifiers for each stage may or may not be related to other stages. Each tag for any combinatorial synthesis must allow for being distinguished from all other tags. In this manner, very large combinatorial libraries may be prepared with a relatively small number of tags, usually fewer than 60 tags, more usually fewer than about 50 tags.

For each bead, there will usually be at least 0.01 femtomol, more usually 0.001–50 pmol, of each tag, although lesser or greater amounts may be used in special circumstances. The amount of product may also be at least in the same range and up to at least $10^4$ or more greater, usually being at least 0.01 pmol, more usually at least 1.0 pmol and generally not more than about 10 nmol. Depending upon the number of beads, the number of stages and the number of choices per stage, the number of products produced will usually exceed $10^2$, more usually $10^3$, and may exceed $10^{10}$, usually not exceeding about $10^8$, preferably being in the range of about $10^4$ to $10^8$, more usually $10^5$ to $10^8$.

The tags will, for the most part, be organic molecules. Each tag will usually have fewer than about 100 atoms, more usually fewer than about 80 atoms, generally fewer than about 60 atoms, other than hydrogen, excluding a linking moiety which would not be retained on release of the tag from the bead. The linking moiety may be of any size, usually being fewer than about 30 atoms, more usually fewer than 20 atoms, other than hydrogen. The size of the linking moiety is not critical, but one of convenience. The tags may form families of compounds, where all of the compounds are of a similar nature or may be combinations of different families, where the compounds may be aliphatic, alicyclic, aromatic, heterocyclic, or combinations thereof. Distinguishing features may be the number of repetitive units, such as methylene groups in an alkyl moiety, alkyleneoxy groups in a polyalkyleneoxy moiety, halo groups in a polyhalocompound, α- and/or β-substituted ethylenes, where the substituents may involve alkyl groups, oxy, carboxy, amino, halo, or the like; isotopes; etc.

Tag Analysis

Tags may be removed from the bead using reductive, oxidative, thermolytic, hydrolytic, or photolytic conditions depending on the nature of the group $F^2$; for example, by oxidation of a catechol ether with ceric ammonium nitrate or by photolysis of a nitrobenzyl ether or ester or amide, or by other methods, e.g. as shown in Table 1.

Differentiation of tags can be achieved with physical differences, e.g. molecular weight of the tags or the chromatographic retention time using gas or liquid chromatography. Positional isomers may have different retention times. If positional isomers or steroisomers are inadequate for physical separation, then one could use varying numbers of substituents, e.g. halogens, such as fluorines, methyl groups, oxy groups, or other side chains in conjunction with differing numbers of units, e.g. methylene groups or ethyleneoxy groups, to provide the desired separation. Ratios of radioisotopes could be used, where the radioisotopes provide for differential emission, for example $^{14}C$ and $^3H$. The physical differences, particularly mass number, can provide information about choice and stage.

Instead of $^{14}C/^3H$ ratios, one could use combinations of non-radioactive isotopes, e.g. —$CH_mD_n$, where m is 0 and up to 3 and n is 3 minus m. For example, by detecting the varying amounts of up to four different methyl groups using mass spectroscopy, one could define a large number of choices.

When E is a bond and $\underline{C}$ is H, the tags obtained upon release from the support have an active functionality for reaction with a labeling reagent which introduces a detectable tag component E. Conveniently, the functionality could be a double bond, particularly an activated double bond, hydroxy, thio, amino, carboxy, etc. The tag would then be reacted with an excess of the labeling reagent to provide the product (E—$\underline{C}$) for analysis. In this way a wide variety of labeling reagents could be used as part of the identifying system, which may not be compatible with the synthetic strategy for the product of interest. Labeling reagents which may be used for detection include haloaromatics (e.g., perfluorobenzyl bromide), fluorescers (e.g., dansyl chloride), radioisotopes, chemiluminescers, etc.

While exemplary tags and reactions have been given, it should be understood that many other combinations could be employed.

Depending on the chemical and physical nature of the tags, an appropriate method for separation is chosen, desirably one of various chromatographic procedures including gas chromatography (GC), liquid chromatography (LC) particularly high-performance liquid chromatography (HPLC), thin layer chromatography (TLC), electrophoresis, etc. Instead of chromatographic procedure, mass spectrometry may be employed for separation by mass number. Tags include:

- for GC: chemically inert organic molecules having different molecular weights including alkanes, alkenes, arenes, halocarbons, ethers, alcohols, silanes, thioethers, etc., particularly halogenated compounds, with or without other functionalities, for electron capture detection or mass spectroscopy detection (MS) with capillary GC separation, and for compound with elements not normally found in organic chemistry (e.g., Sn, Ge) for atom emission detection with GC capillary seperation;

- for LC, HPLC or TLC: see above for GC, conveniently linear ethers or hydrocarbons with substitution by radioisotopes or combinations of radioisotopes for radioassay detection or suitable groups for fluorescence detection after separation;

- for electrophoresis: see above, particularly functionalized charged molecules, e.g. cationic or anionic, particularly organic or inorganic acid groups, where the molecule may be further modified by having a detectable radioisotope or fluorescer for detection in the electrophoresis;

- for mass spectroscopy: see above, particularly different mass numbers due to different isotopes, different numbers of the same functionality or different functionalities, different members of a homologous series or combinations thereof.

The separation of tags from one another may involve individual techniques or combinations of techniques, e.g. chromatography and electrophoresis; gas chromatography and mass spectroscopy; etc.

The tags of the present invention will have a property which allows detection at very low levels, usually not greater than nanomol, preferably picomol or less, more preferably femtomol or less, in the presence of other compounds which may be present at significantly higher levels. For this reason, specific atomic substitutions may be used to render the labels easily detectable. Such substitutions include:

(a) substitution by electronegative elements, e.g. fluorine or chlorine, for electron capture detection in conjunction with capillary GC or negative ion mass spectroscopy detection;

(b) substitution by an uncommon element (excluding C, H, and O) for atomic emission detection in conjunction with capillary GC;

(c) substitution by several uncommon elements for atomic emission detection to determine the ratio between the elements;

(d) substitution by a radioactive element, e.g. $^3H$, for detection by autoradiography or scintillation counting in conjunction with LC, TLC or electrophoresis;

(e) substitution by a multiplicity of radioactive elements having differing emissions, e.g. $^3H$ and $^{14}C$, for detection by autoradiography or scintillation counting to determine the ratio of the different radioactive elements.

For single-element substitution (a., b., d. above) a separable mixture of A tags whose simple presence or absence can be detected would encode up to $2^A$ different syntheses. For multiple-element substitution (see, c. and e. above) a separable mixture of A tags each having B distinguishable states (e.g., different $^3H/^{14}C$ ratios, different Si/Sn ratios) would be able to encode for up to $B^A$ different syntheses.

A wide variety of isotopes exist, where the presence or ratio of isotopes may provide information as to stage and choice. The isotopes may be radioactive or non-radioactive. Isotopes of particular interest include deuterium, tritium, $^{14}C$, $^{32}P$, $^{131}I$, etc.

By employing mixtures of isotopically-modified compounds, one can greatly expand the information obtained from a single tag compound which is only distinguished by the presence of isotopes. For example, one could prepare a mixture of ratios of hydrogen to deuterium, where the various ratios could differ by as little as 10% each. By replacing hydrogens with another atom, such as fluorine, one would then have a varying mixture of hydrogens, deuteriums and fluorines, providing for a large number of different differentiable tags.

Other groups that may be involved could be aromatic rings, which are differentially substituted, as to position and functionality. Thus, by having substituted benzene rings, where the position of the substitution and the nature of the substitution can be determined, one can provide for a plurality of molecules which can be distinguished and can provide for both stage and choice information. For example, if $\underline{C}$ were constant one could detect and discriminate through the substitution pattern on E when E is a polyhalogenated aromatic ring.

There is also the possibility to use fluorescent tags. While fluorescent tags alone may not be sufficient to define a significant number of stages with a significant number of choices, as referred to above, by providing for means for separating the fluorescent tagging molecules based on variations in $\underline{C}$ or $\underline{C}'$, one can individually detect the tags by their fluorescence.

The mixture of tags associated with a particular bead may be detached and subject to an initial separation, where it is desirable to detect each of the tags separately. Once the group of tags has been separated, each of the tags may then be analyzed based on its particular functionalities and distinctive properties. Various techniques which may be used to detect the particular tags include autoradiography or scintillation counting, electron capture detection, negative or positive ion mass spectroscopy, infrared spectroscopy, ultraviolet spectroscopy, electron spin resonance spectroscopy, fluorescence, and the like.

Another composition may have at least 6 different markers being associated in a kit or in a common medium, each marker having a distinguishable moiety which is substantially chemically inert, differing from each other in molecular weight, said markers of the formula:

$$\Lambda-\{\Delta-(T)_\alpha \text{ or } (T)_\alpha-\Delta \text{ or } \Delta_1-(T)_\alpha-\Delta^2\} \tag{1}$$

where $\Lambda$ is a linking group which has a functionality for bonding to a solid support and a functionality for detachment from the solid support, which may be included in the functionality for bonding to the solid support;

$\Delta$ is a distinguishing group, which allows for the distinguishing by a physical characteristic of each of the markers from each of the other markers by other than fluorescence, so as to provide a set of markers which allows for coding a multistep synthetic procedure, and includes any remaining functional group after detachment, which was previously associated with the linked group;

$\Delta^1$ and $\Delta^2$ are portions of the distinguishing group, which together define a distinguishing group and when joined together come within the definition of $\Delta$;

T is a detectable group, which when attached to the distinguishing group allows for the low level detection of the marker, where the detectable group may be present on the marker in the kit or may be added later to the distinguishing group and if attached to the linking group, includes any remaining functional group after detachment, which was previously associated with the linking group; and $\alpha$ is 0 or 1, indicating that the detectable group may or may not be present;

$$ss-(\Lambda'-\{\Delta-(T)_\alpha \text{ or } (T)_\alpha-\Delta \text{ or } \Delta_1-(T)_\alpha-\Delta^2\})_\beta \tag{2}$$

where all of the symbols have been defined previously, except as follows: ss is a solid support; $\Lambda'$ is a linking group covalently bonded to ss; and $\beta$ is an integer as to each solid support and is at least six and usually not more than about 30;

$$\Lambda''-\{\Delta''-(T)_\alpha \text{ or } (T'')_\alpha-\Delta \text{ or } \Delta'^1-(T)_\alpha-\Delta^2\} \tag{3}$$

where all of the symbols have been defined previously, except as follows: $\Delta''$ is hydrogen or the residue of the linking group after photolytic cleavage, elimination or other chemical reaction which results in detachment from the solid support; $\Delta''$ or $\Delta'^1$ is $\Delta$ or $\Delta^1$ or a modified $\Delta$ or $\Delta^1$, respectively, as a result of the detachment of the marker from the solid support; T'' is T or a modified T as a result of the detachment of the marker from the solid support;

$$T_\alpha-\Lambda'''-\{\Delta''-(T)_\alpha \text{ or } (T'')_\alpha-\Delta \text{ or } \Delta'^1-(T)_\alpha-\Delta^2\} \tag{4}$$

where all of the symbols have been defined previously and $\Lambda'''$ is a bond or the remaining portion of the linker group after attachment to T; with the additional limitation that only one $\alpha$ is 1.

Assays

To determine the characteristic of interest of the product, a wide variety of assays and techniques may be employed.

Frequently, in screening the beads, one will use either single beads or mixtures of beads and determine whether the bead or mixtures show activity. Thus, the mixtures may involve 10, 100, 1000 or more beads. In this way, large groups of compounds may be rapidly screened and segregated into smaller groups of compounds.

One technique is where one is interested in binding to a particular biomolecule such as a receptor. The receptor may be a single molecule, a molecule associated with a microsome or cell, or the like. Where agonist activity is of interest, one may wish to use an intact organism or cell, where the response to the binding of the subject product may be measured. In some instances, it may be desirable to detach the product from the bead, particularly where physiological activity by transduction of a signal is of interest.

Various devices are available for detecting cellular response, such as a microphysiometer, available from Molecular Devices, Redwood City, Calif. Where binding is of interest, one may use a labeled receptor, where the label is a fluorescer, enzyme, radioisotope, or the like, where one can detect the binding of the receptor to the bead. Alternatively, one may provide for an antibody to the receptor, where the antibody is labeled, which may allow for amplification of the signal and avoid changing the receptor of interest, which might affect its binding to the product of interest. Binding may also be determined by displacement of a ligand bound to the receptor, where the ligand is labeled with a detectable label.

In some instances, one may be able to carry out a two-stage screen, whereby one first uses binding as an initial screen, followed by biological activity with a viable cell in a second screen. By employing recombinant techniques, one can greatly vary the genetic capability of cells. One can then produce exogenous genes or exogenous transcriptional regulatory sequences, so that binding to a surface membrane protein will result in an observable signal, e.g. an intracellular signal. For example, one may introduce a leuco dye into the cell, where an enzyme which transforms the leuco dye to a colored product, particularly a fluorescent product, becomes expressed upon appropriate binding to a surface membrane, e.g. β-galactosidase and digalactosidylfluorescein. In this manner, by associating a particular cell or cells with a particular particle, the fluorescent nature of the cell may be determined using a FACS, so that particles carrying active compounds may be identified. Various techniques may be employed to ensure that the particle remains bound to the cell, even where the product is released from the particle. For example, one may use antibodies on the particle to a surface membrane protein, one may link avidin to the surface of the cell and have biotin present on the particle, etc.

Assays may be performed stagewise using individual particles or groups of particles or combinations thereof. For example, after carrying out the combinatorial syntheses, groups of about 50 to 10,000 particles may be segregated in separate vessels. In each vessel, as to each particle a portion of the product bound to the particle is released. The fractional release may be as a result of differential linking of the product to the particle or using a limited amount of a reagent, condition or the like, so that the average number of product molecules released per particle is less than the total number of product molecules per particle. One would then have a mixture of products in a small volume. The mixture could then be used in an assay for binding, where the binding event could be inhibition of a known binding ligand binding to a receptor, activation or inhibition of a metabolic process of a cell, or the like. Various assay conditions may be used for the detection of binding activity as will be described subsequently. Once a group is shown to be active, the individual particles may then be screened, by the same or a different assay. One could of course, have a three- or four-stage procedure, where large groups are divided up into smaller groups, etc. and finally single particles are screened. In each case, portions of the products on the particles would be released and the resulting mixture used in an appropriate assay. The assays could be the same or different, the more sophisticated and time consuming assays being used in the later or last stage.

One may also provide for spatial arrays, where the particles may be distributed over a honeycomb plate, with each well in the honeycomb having 0 or 1 particle.

The subject methodology may be used to find chemicals with catalytic properties, such as hydrolytic activity, e.g. esterase activity. For this purpose one might embed beads in a semisolid matrix surrounded by diffusible test substrates. If the catalytic activity can be detected locally by processes that do not disturb the matrix, for example, by changes in the absorption of light or by detection of fluorescence due to a cleaved substrate, the beads in the zone of catalytic activity can be isolated and their labels decoded.

Instead of catalytic activity, compounds with inhibitory or activating activity can be developed. Compounds may be sought that inhibit or activate an enzyme or block a binding reaction. To detect beads that inhibit an enzyme, which beads have an attached product with this desirable property, it is advantageous to be able to release the products from the beads, enabling them to diffuse into a semisolid matrix or onto a filter where this inhibition, activation or blocking can be observed. The beads that form a visualized or otherwise detectable zone of inhibition, activation or blocking can then be picked and the tags decoded. In this case it is necessary that a portion of the synthesized products be attached to the beads by cleavable linkages, preferably a photolabile linkage, while a portion of the tags remain attached to the bead, releasable after picking by a different means than before.

A dialysis membrane may be employed where a layer of beads is separated from a layer of radiolabeled ligand/receptor pair. The bead layer could be irradiated with ultraviolet light and the product released from the bead would diffuse to the pair layer, where the radiolabeled ligand would be released in proportion to the affinity of the compound for the receptor. The radiolabeled ligand would diffuse back to the layer of beads. Since the radiolabel would be proximal to the bead, beads associated with radioemission would be analyzed.

Of particular interest is finding products that have biological activity. In some applications it is desirable to find a product that has an effect on living cells, such as inhibition of microbial growth, inhibition of viral growth, inhibition of gene expression or activation of gene expression. Screening of the compounds on the beads can be readily achieved, for example, by embedding the beads in a semisolid medium and the library of product molecules released from the beads (while the beads are retained) enabling the compounds to diffuse into the surrounding medium. The effects, such as plaques with a bacterial lawn, can be observed. Zones of growth inhibition or growth activation or effects on gene expression can then be visualized and the beads at the center of the zone picked and analyzed.

One assay scheme will involve gels where the molecule or system, e.g. cell, to be acted upon may be embedded substantially homogeneously in the gel. Various gelling agents may be used such as polyacrylamide, agarose, gelatin, etc. The particles may then be spread over the gel so as to have sufficient separation between the particles to allow for individual detection. If the desired product is to have hydrolytic activity, a substrate is present in the gel which would provide a fluorescent product. One would then screen the gel for fluorescence and mechanically select the particles associated with the fluorescent signal.

One could have cells embedded in the gel, in effect creating a cellular lawn. The particles would be spread out as indicated above. Of course, one could place a grid over the gel defining areas of one or no particle. If cytotoxicity were the criterion, one could release the product, incubate for a sufficient time, followed by spreading a vital dye over the gel. Those cells which absorbed the dye or did not absorb the dye could then be distinguished.

As indicated above, cells can be genetically engineered so as to indicate when a signal has been transduced. There are many receptors for which the genes are known whose expression is activated. By inserting an exogenous gene into a site where the gene is under the transcriptional control of the promoter responsive to such receptor, an enzyme can be produced which provides a detectable signal, e.g. a fluorescent signal. The particle associated with the fluorescent cell(s) may then be analyzed for its reaction history.

Libraries and Kits

For convenience, libraries and/or kits may be provided. The libraries would comprise the particles to which a library of products and tags have been added so as to allow for screening of the products bound to the bead or the libraries would comprise the products removed from the bead and grouped singly or in a set of 10 to 100 to 1000 members for screening. The kits would provide various reagents for use as tags in carrying out the library syntheses. The kits will usually have at least 4, usually 5, different compounds in separate containers, more usually at least 10, and may comprise at least $10^2$ different separated organic compounds, usually not more than about $10^2$, more usually not more than about 36 different compounds. For binary determinations, the mode of detection will usually be common to the compounds associated with the analysis, so that there may be a common chromophore, a common atom for detection, etc. Where each of the identifiers is pre-prepared, each will be characterized by having a distinguishable composition encoding choice and stage which can be determined by a physical measurement and including groups or all of the compounds sharing at least one common functionality.

Alternatively, the kit can provide reactants which can be combined to provide the various identifiers. In this situation, the kit will comprise a plurality of separated first functional, frequently bifunctional, organic compounds, usually four or more, generally one for each stage of the synthesis, where the functional organic compounds share the same functionality and are distinguishable as to at least one determinable characteristic. In addition, one would have at least one, usually at least two, second organic compounds capable of reacting with a functionality of the functional organic compounds and capable of forming mixtures which are distinguishable as to the amount of each of said second organic compounds. For example, one could have a glycol, amino acid, or a glycolic acid, where the various bifunctional compounds are distinguished by the number of fluorine or chlorine atoms present, to define stage, and have an iodomethane, where one iodomethane has no radioisotope, another has $^{14}C$ and another has one or more $^3H$. By using two or more of the iodomethanes, one could provide a variety of mixtures which could be determined by their radioemissions. Alternatively, one could have a plurality of second organic compounds, which could be used in a binary code.

As indicated previously one could react the tags after release with a molecule which allows for detection. In this way the tags could be quite simple, having the same functionality for linking to the particle as to the detectable moiety. For example, by being linked to a hydroxycarboxyl group, an hydroxyl group would be released, which could then be esterified or etherified with the molecule which allows for detection. For example, by using combinations of fluoro- and chloroalkyl groups, in the binary mode, the number of fluoro and/or chloro groups could determine choice, while the number of carbon atoms would indicate stage.

Groups of compounds of particular interest include linkers joined to a substituted ortho-nitrobenzyloxy group, indanyloxy or fluorenyloxy group, or other group which allows for photolytic or other selective cleavage. The linking group may be an alkylene group of from 2 to 20 carbon atoms, polyalkyleneoxy, particularly alkyleneoxy of from 2 to 3 carbon atoms, cycloalkyl group of from 4 to 8 carbon atoms, haloalkyl group, particularly fluoroalkyl of from 2 to 20 carbon atoms, one or more aromatic rings and the like, where the linker provides for the discrimination between the various groups, by having different numbers of units and/or substituents.

Individual particles or a plurality of particles could be provided as articles of commerce, particularly where the particle(s) have shown a characteristic of interest. Based on the associated tags, the reaction history may be decoded. The product may then be produced in a large synthesis. Where the reaction history unequivocally defines the structure, the same or analogous reaction series may be used to produce the product in a large batch. Where the reaction history does not unambiguously define the structure, one would repeat the reaction history in a large batch and use the resulting product for structural analysis. In some instances it may be found that the reaction series of the combinatorial chemistry may not be the preferred way to produce the product in large amounts.

Thus, an embodiment of this invention is a kit comprising a plurality of separated organic compounds, each of the compounds characterized by having a distinguishable composition, encoding at least one bit of different information which can be determined by a physical measurement, and sharing at least one common functionality. A preferred embodiment is a kit comprising at least 4 different functional organic compounds.

More preferred is a kit wherein said functional organic compounds are of the formula:

     I where $F^1\text{---}F^2$ is a linker which allows for attachment to and detachment from a solid particle; and C—E—C' is a tag member which can be determined by a physical measurement, especially wherein said functional organic compounds differ by the number of methylene groups and/or halogens, nitrogens or sulfurs present.

Also preferred is a kit wherein the C—E—C" portion is removed photochemically or a kit wherein the C—E—C' portion is removed oxidatively, hydrolytically, thermolytically, or reductively.

Compounds of this invention may be useful as analgesics and/or for the treatment of inflammatory disease, especially in the case of the azotricyclics acting as antagonists of the meurokin 1/brandykin receptor. Members of the benzodiazopine library may be useful as a muscle relaxant and/or tranquilizer and/or as a sedative. Members of the 23 million Mixed Amide Library may be of use in the treatment of hypertension on endothelin antagonists or Raynaud's syndrome.

The following examples are offered by way of illustration and not by way limitation.

In one embodiment the invention is a composition comprising at least 6 different components, each component having a distinguishable moiety. The components may be characterized by each moiety being substantially chemically stable or inert and having an identifiable characteristic different from each of the other moieties. Each moiety is joined to a linking group having an active functionality capable of forming a covalent bond through a linking group to individually separable solid surfaces, or joined to a group which is detectable at less than 1 nanomole, with a proviso that when the moieties are joined to the linking group, the components are physically segregated. Preferably, the solid supports are beads. In one embodiment each component comprises molecules of different compounds bound to individual separable solid surfaces, wherein the molecules on the solid surfaces. Preferably, the moieties of the invention define an homologous series and/or a series of substitutions on a core molecule.

The invention herein is also directed to a compound library comprising at least one hundred unique solid supports. In this compound library each solid support has (1) an individual compound bound to the solid support as a major compound bound to the support; and (2) a plurality of tags e.g. tags incapable of being sequenced, where the tags are individual tag molecules which are physically distinguishable in being physically separable and are substituted so as to be detectable at less than about a nanomole or have a functional group for bonding to a substituent which is detectable at less than about at nanomole. Preferably, in the compound library each solid support has at least about 6 tags. In another embodiment, in the compound library the tags define a binary code encoding the synthetic protocol used for the synthesizing of the compound on the solid support.

This invention also provides a method for determining a synthetic protocol encoded by separable physically different tags in a series and defining a binary code. In this method at least two tags are employed to define each stage of the synthetic protocol, there being at least six tags. The step of the method comprises separating tags by means of their physical differences and detecting the tags. The synthetic protocol is defined a binary code of different tags.

Compounds of this invention may be useful as analgesics and/or for the treatment of inflammatory disease, especially in the case of the azatricyclics acting as antagonists of the neurokinin 1/bradykinin receptor. Members of the benzediazepine library may be useful as a muscle relaxant and/or tranquilizer and/or as a sedative. Members of the 23.5 Million Mixed Amide Library (Example 6) may be of use in the treatment of hypertension or Raynaud's syndrome by acting as endothelin antagonists.

EXAMPLE 1

PEPTIDE LIBRARY

In order to encode up to $10^9$ different syntheses, one could prepare 30 different identifiers which carry individual tags capable of being separated one from another by capillary GC. For encoding a smaller number of syntheses, fewer identifiers would be used. The tags would normally be prepared from commercially-available chemicals as evidenced by the following illustration. ω-Hydroxyalkenes-1, where the number of methylene groups would vary from 1 to 5, would be reacted with an iodoperfluoroalkane, where the number of $CF_2$ groups would be 3, 4, 6, 8, 10, and 12. By employing a free-radical catalyst, the iodoperfluorocarbon would add to the double bond, where the iodo group could then be reduced with hydrogen and a catalyst or a tin hydride. In this manner, 30 different tags could be prepared. The chemical procedure is described by Haszeldine and Steele. *J. Chem. Soc.* (London), 1199 (1953); Brace, *J. Fluor. Chem.*, 20, 313 (1982). The highly fluorinated tags can be easily detected by electron capture, have different GC retention times, so that they are readily separated by capillary GC, are chemically inert due to their fluorinated, hydrocarbon structure and each bears a single hydroxyl functional group for direct or indirect attachment to particles.

Before attachment to compound precursors, the tags (referred to as T1–T30) would be activated in a way which is appropriate for the chemical intermediates to be used in the combinatorial synthesis. By appropriate it is intended that a functionality would be added which allows for ready attachment by a chemical bond to a compound precursor or to the bead matrix itself. The activation process would be applied to each of the 30 different tags and allow these tags to be chemically bound, either directly or indirectly, to intermediates in the combinatorial compound synthesis. For example, a carboxy derivative could be used for coupling and upon activation the resulting carboxy group would bond to the particle.

In the case of a combinatorial synthesis of a peptidic compound or other structure made of amide-linked organic fragments, the encoding process could consist of addition of a carboxylic acid-equipped linker. For example, the tag would be coupled to the tert.-butyl ester of o-nitro-p-carboxybenzyl bromide in the presence of sodium hydride. The ester would then be hydrolyzed in dilute trifluoroacetic acid.

Activated identifiers would be coupled to intermediates at each stage in the combinatorial compound synthesis. The ortho-nitrobenzyl ether part of the activated identifiers is used to allow photochemical detachment of the tags after completing the combinatorial synthesis and selecting the most desirable compounds. The detached tags would then be decoded using capillary GC with electron capture detection to yield a history of the synthetic stages used to prepare the compound selected.

While there is an almost unlimited set of chemical stages and methods which could be used to prepare combinatorial libraries of compounds, we will use coupling of α-amino acids to make a combinatorial library of peptides as an example of an application of the encoding methodology. In this example, we will describe preparation of a library of pentapeptides having all combinations of 16 different amino acids at each of the five residue positions. Such a library would contain $16^5$ members. To uniquely encode all members of this library, 20 detachable tags (T1–T20) as described above would be required.

To prepare the encoded library, we would begin with a large number (>$10^6$) of polymer beads of the type used for Merrifield solid phase synthesis and functionalized by free amino groups. We would divide the beads into 16 equal portions and place a portion in each of 16 different reaction vessels (one vessel for each different α-amino acid to be added). We would then add a small portion (e.g., 1 mol %) of identifiers to each of the amino acid derivatives (e.g., Fmoc amino acids) to be coupled in the first stage of the combinatorial synthesis. The specific combination of the tags incorporated into the identifiers added would represent a simple binary code which identifies the amino acid used in the first stage of synthesis. The 16 amino acids added would be indicated by numbers 1–16 and any such number could be represented chemically by combinations of the first four tags (T1–T4). In tables 2 and 3, a typical encoding scheme is shown in which the presence or absence of a tag is indicated by a 1 or a 0, respectively. The letter T may represent either the tag or the identifier incorporating that tag.

TABLE 2

| A typical encoding scheme. | | | | |
|---|---|---|---|---|
| Amino Acid added in first stage | T4 | T3 | T2 | T1 |
| Number 1 (e.g., glycine) | 0 | 0 | 0 | 0 |
| Number 2 (e.g., alanine) | 0 | 0 | 0 | 1 |
| Number 3 (e.g., valine) | 0 | 0 | 1 | 0 |
| Number 4 (e.g., serine) | 0 | 0 | 1 | 1 |
| Number 5 (e.g., threonine) | 0 | 1 | 0 | 0 |
| . | | | | |
| Number 16 (e.g., tryptophan) | 1 | 1 | 1 | 1 |

We would then carry out a standard dicyclohexylcarbodiimide (DCC) peptide coupling in each of the 16 vessels using the Fmoc amino acids admixed with small amounts of the encoding activated identifiers as indicated above. During the couplings, the amino acids as well as small amounts (e.g., 1%) of the identifiers would become chemically bound to intermediates attached to the beads. Next the beads would be thoroughly mixed and again separated into 16 portions. Each portion would again be placed in a different reaction vessel. A second amino acid admixed with appropriate new activated identifiers (T5-T8) would be added to each vessel and DCC coupling would be carried out as before. The particular mixture of the incorporated tags (T5-T8) would again represent a simple binary code for the amino acid added in this, the second stage of the combinatorial synthesis.

TABLE 3

| A typical encoding scheme. | | | | |
|---|---|---|---|---|
| Amino Acid added in second stage | T8 | T7 | T6 | T5 |
| Number 1 (e.g., glycine) | 0 | 0 | 0 | 0 |
| Number 2 (e.g., alanine) | 0 | 0 | 0 | 1 |
| Number 3 (e.g., valine) | 0 | 0 | 1 | 0 |
| Number 4 (e.g., serine) | 0 | 0 | 1 | 1 |
| Number 5 (e.g., threonine) | 0 | 1 | 0 | 0 |
| . | | | | |
| Number 16 (e.g., tryptophan) | 1 | 1 | 1 | 1 |

After the 16 couplings of stage 2 are complete, the beads would be again mixed and then divided into 16 new portions for the third stage of the synthesis. For the third stage, T9-T12 would be used to encode the third amino acid bound to the beads using the same scheme used for stages 1 and 2. After the third couplings, the procedure would be repeated two more times using the fourth amino acids with T13-T16 and the fifth amino acids with T17-T20 to give the entire library of 1,048,576 different peptides bound to beads.

Although the above beads would be visually indistinguishable, any bead may be chosen (e.g., by selecting based on the interesting chemical or biological properties of its bound peptide or other target molecule) and its synthetic history may be learned by detaching and decoding the associated tags.

The precise method used to detach tags will depend upon the particular linker used to chemically bind it to intermediates in the combinatorial synthesis of the target compound. In the example above, the ortho-nitrobenzyl carbonate linkages, which are known to be unstable to ~300 nm light (Ohtsuka, et al., *J. Am. Chem. Soc.*, 100, 8210 [1978]), would be cleaved by photochemical irradiation of the beads. The tags would then diffuse from the beads into free solution which would be injected into a capillary gas chromatograph (GC) equipped with a sensitive electron capture detector. Since the order in which the tags (T1-T20) emerged from the GC and their retention times under standard conditions were previously determined, the presence or absence of any of T1-T20 would be directly determined by the presence or absence of their peaks in the GC chromatogram. If 1 and 0 represent the presence and absence respectively of peaks corresponding to T1-T20, then the chromatogram can be taken as a 20-digit binary number which can uniquely represent each possible synthesis leading to each member of the peptide library. The use of halocarbon tags which are safe, economical and detectable at subpicomole levels by electron capture detection makes this capillary GC method a particularly convenient encoding scheme for the purpose.

As an example of using the encoding scheme for the pentapeptide library above, a particular bead is irradiated with light to detach the tags, the solubilized labels injected into a capillary GC and the following chromatogram obtained ("Peak" line):

| Label | 20 | 19 | 18 | 17 | 16 | 15 | 14 | 13 | 12 | 11 | 10 | 9 | 8 | 7 | 6 | 5 | 4 | 3 | 2 | 1 | GC Inject |
|---|---|---|---|---|---|---|---|---|---|---|---|---|---|---|---|---|---|---|---|---|---|
| Peek | l | l | l | l | | l | | | | | l | l | | | | l | | l | | | l |
| Binary | 1 | 1 | 1 | 1 | 0 | 1 | 0 | 0 | 0 | 0 | 1 | 1 | 0 | 0 | 0 | 1 | 0 | 0 | 1 | 0 | |
| Stage | ----5---- | | | | ----4---- | | | | ----3---- | | | | ----2---- | | | | ----1---- | | | | |
| AA | Tryptophan | | | | Threonine | | | | Serine | | | | Alanine | | | | Valine | | | | |

The "Label" line diagrams the GC chromatogram where T20-T1 peaks (l) are to be found (note the injection is given on the right and the chromatogram reads from right to left). The "Peak" line represents the presence of labels (T20-T1) as peaks in the chromatogram. The "Binary" line gives presence (1) or absence (0) of peaks as a binary number. The "Stage" line breaks up the binary number into the five different parts encoding the five different stages in the synthesis. Finally, the "AA" line gives the identity of the amino acid which was added in each stage and was given by the binary code in the "Binary" line above.

EXAMPLE 2

RADIO-LABELED TAGS

In the next illustration, the tags employed are monomethylethers of linear alkyl-α,ω-diols. The diol would have N+2 carbon atoms, where N designates the stage. The methyl group would be a radiolabeled reagent which would have any of a variety of $^3H/^{14}C$ ratios from 1/1 to m/1, where m is the number of choices. The double radiolabel allows for accurate quantitation of the tritium present in the tag. By having 10 different alkylene groups and 10 different radioactive label ratios, $10^{10}$ unique ten-member sets of tags are generated. Tags would be attached by first reacting them with activating agents, e.g. phosgene to form a chloroformate, followed by reaction with the $F^1$—$F^2$ component. In this case, $F^1$—$F^2$ is the o-nitro-p-carboxy-benzyl alcohol protected as the t-butyl ester. Each time a synthetic stage is carried out, the de-esterified identifier is added directly to the bead, which has covalently bonded amine or hydroxyl groups, to form amides or esters with the acid activated using standard chemistry, e.g., carbodiimide coupling methodology. At the end of the sequential synthesis, the beads are then screened with a variety of receptors or enzymes to determine a particular characteristic. The beads demonstrating the characteristic may then be isolated, the tags detached and separated by HPLC to give a series of glycol monomethyl ethers which may then be analyzed for radioactivity by standard radioisotope identification methods. For example, if the first and second tags to elute from the HPLC column had $^3H/^{14}C$ ratios of 5:1 and 7:1 respectively, then the product which showed activity had been synthesized by reagent number 5 in stage 1 and reagent number 7 in stage 2.

EXAMPLE 3

2401 Peptide Library

The identifiers employed were 2-nitro-4-carboxybenzyl, O-aryl substituted ω-hydroxyalkyl carbonate, where alkyl was of from three to 12 carbon atoms and aryl was (A) pentachlorophenyl, (B) 2,4,6-trichlorophenyl, or (C) 2,6-dichloro-4-fluorophenyl. The tags are designated as NAr, wherein N is the number of methylene groups minus two and Ar is the aryl group. Thus, tag 2A has a butylene group bonded to the pentachlorophenyl through oxygen. The subject tags can be easily detected using electron capture gas chromatography at about 100 fmol.

In the subject analysis, the tagging molecules are arranged in their GC elution order. Thus the tag which is retained the longest on the GC column is designated T1 and is associated with the least significant bit in the binary synthesis code number, the next longest retained tag is called T2 representing the next least significant binary bit, and so on. Using an 0.2 mM×20M methylsilicone capillary GC column, eighteen well-resolved tags were obtained where T1 through T18 corresponded to 10A, 9A, 8A, 7A, 6A, 5A, 4A, 3A, 6B, 2A, 5B, 1A, 4B, 3B, 2B, 1B, 2C, and 1C, respectively.

An encoded combinatorial library of 2401 peptides was prepared. This library had the amino acid sequence N-XXXXEEDLGGGG-bead, where the variable X residues were D, E, I, K, L, Q, or S (single letter code). The 4 glycines served as a spacer between the encoded amino acid sequence and the bead. The combinatorial library included the sequence $H_2N$-KLISEEDL, part of the 10 amino acid epitope which is known to be bound by 9E10, a monoclonal antibody directed against the human C-myc gene product. For encoding this library, three binary bits were sufficient to represent the seven alternative reagents for each stage. The code was as follows: 001=S; 010=I; 011=K; 100=L; 101=Q; 110=E; 111=D.

The library was synthesized by first preparing the constant segment of the library $H_2$NEEDLGGGG-bead on 1.5 g of 50–90μ polystyrene synthesis beads functionalized with 1.1 meq/g of aminomethyl groups using standard solid phase methods based on t.-butyl side-chain protection and Fmoc main chain protection (Stewart and Young, "Solid Phase Peptide Synthesis", 2nd edition, Pierce Chemical Co., 1984). After deprotecting the Fmoc groups with diethylamine, the beads were divided into seven 200 mg fractions and each fraction placed in a different Merrifield synthesis vessel mounted on a single wrist-action shaker. The beads in the seven vessels were processed independently as follows (see Table 3-1). The letter T in this example refers to the tag or to the identifier incorporating that tag.

TABLE 3-1

| Vessel No. | Step 1 | Step 2 | Step 3 | Step 4 |
|---|---|---|---|---|
| 1 | 1% T1 | DIC, wash | Fmoc(tBu)S, Anh. | Wash |
| 2 | 1% T2 | " | FmocI, Anh. | " |
| 3 | 1% T1,T2 | " | Fmoc(Boc)K, Anh. | " |
| 4 | 1% T3 | " | FmocL, Anh. | " |
| 5 | 1% T1,T3 | " | Fmoc(trityl)Q, Anh. | " |
| 6 | 1% T2,T3 | " | Fmoc(t-butyl)E, Anh. | " |
| 7 | 1% T1,T2,T3 | " | Fmoc(tBu)D, Anh. | " |

In accordance with the above procedure a sufficient amount of the identifiers listed in step 1 were attached via their carboxylic acids using diisopropylcarbodiimide to tag about 1% of the free amino groups on each bead in the corresponding vessel. The remaining free amino groups on each bead were then coupled in step 3 to N-protected amino acid anhydrides. After washing with methylene chloride, isopropanol, and N,N-dimethylformamide, the beads from the seven vessels were combined and thoroughly mixed. At this point the library had seven members.

After Fmoc deprotection (diethylamine), the beads were again divided into seven vessels and processed as before except that in place of the identifiers used previously, identifiers representing the second stage (T4–6) were used. By repeating the procedure two more times, using identifiers T7–9 and then T10–12 analogously, the entire uniquely encoded library of $7^4$=2401 different peptides was prepared using only 12 identifiers.

To read the synthesis code from a single selected bead, the bead was first washed four times in a small centrifuge tube with 100 μL portions of DMF, and then resuspended in 1 μL of DMF in a Pyrex capillary tube. After 2 hrs of photolysis with a Rayonet 350 nm light source, the tags released from the bound identifiers were silylated using about 0.1 μL bis-trimethylsilylacetamide and the solution injected into a Hewlett Packard capillary gas chromatograph equipped with an 0.2 mM×20M methylsilicone fused silica capillary column and an electron capture detector. The binary synthesis code of the selected bead was directly determined from the chromatogram of the tags which resulted.

EXAMPLE 4

Benzodiazepine Library

A combinatorial benzodiazepine library comprising 30 compounds of the formula VIII

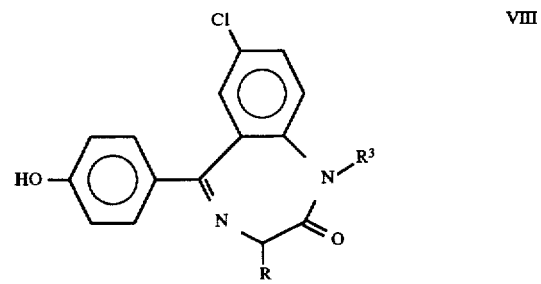

wherein:

R is $CH_3$, $CH(CH_3)_2$, $CH_2CO_2H$, $(CH_2)_4NH_2$, $CH_2C_6H_4OH$, or $CH_2C_6H_5$ and $R^1$ is H, $CH_3$, $C_2H_5$, $CH_2CH=CH_2$, or $CH_2C_6H_5$ is constructed per the following scheme.

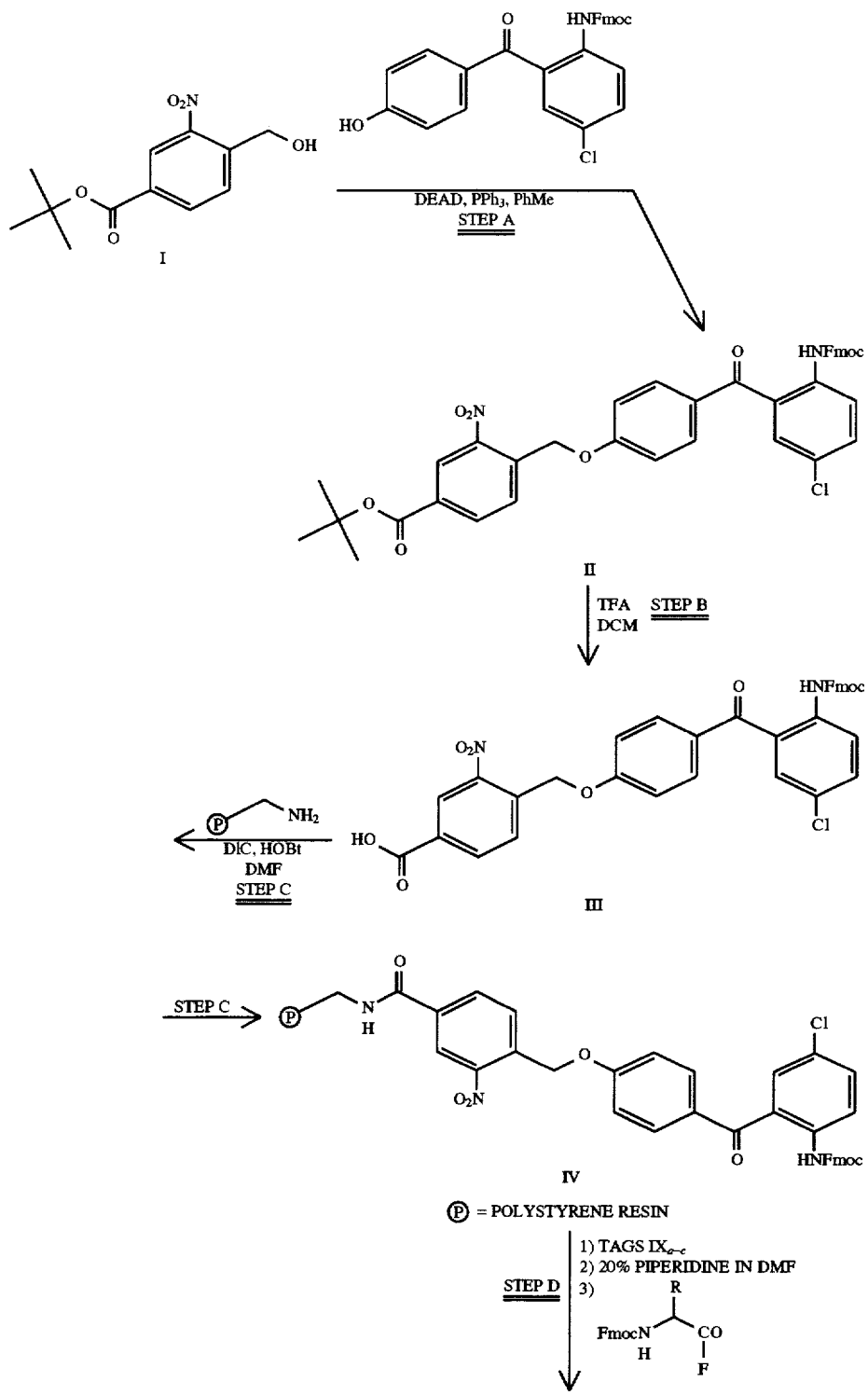

-continued
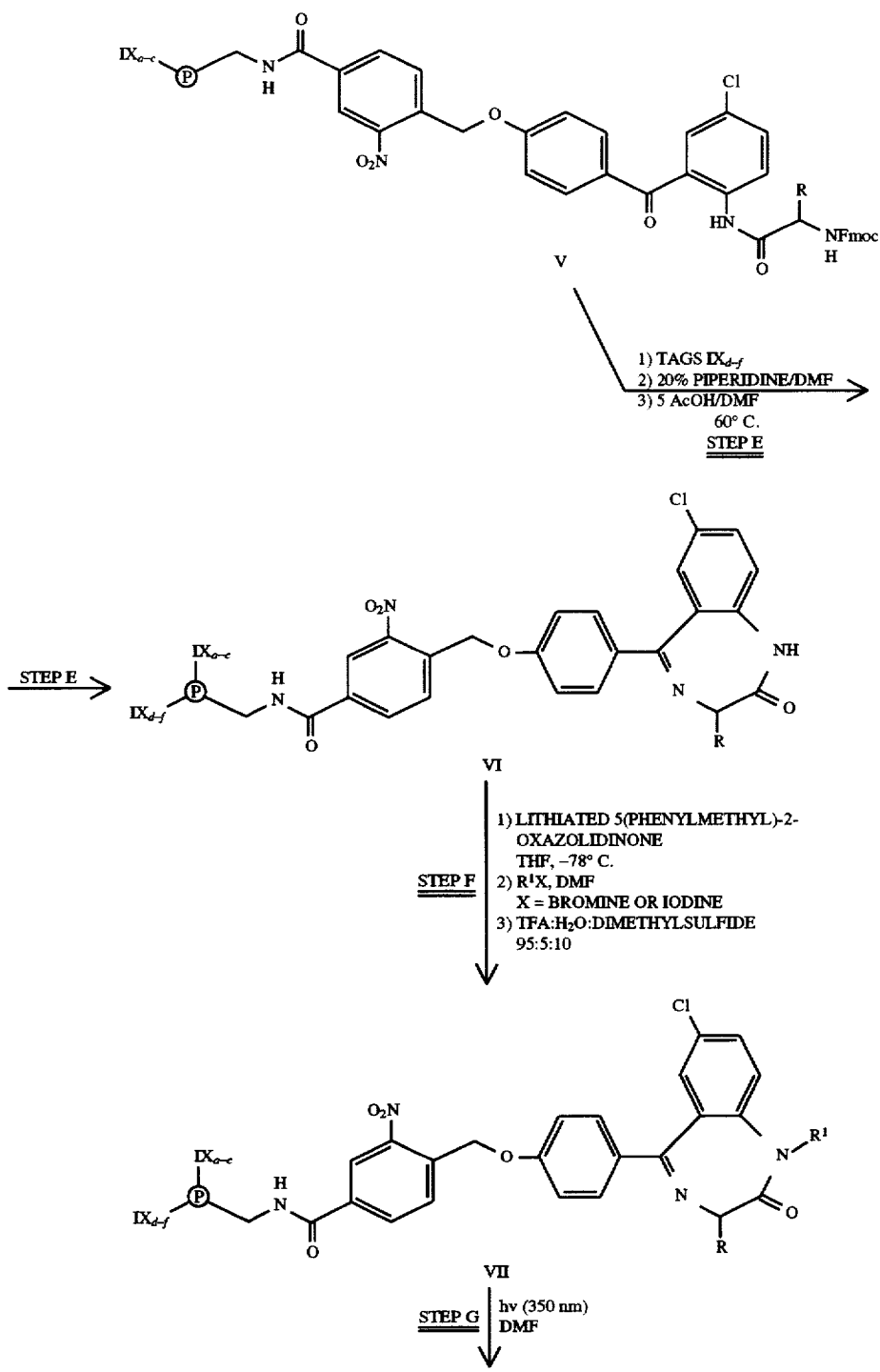

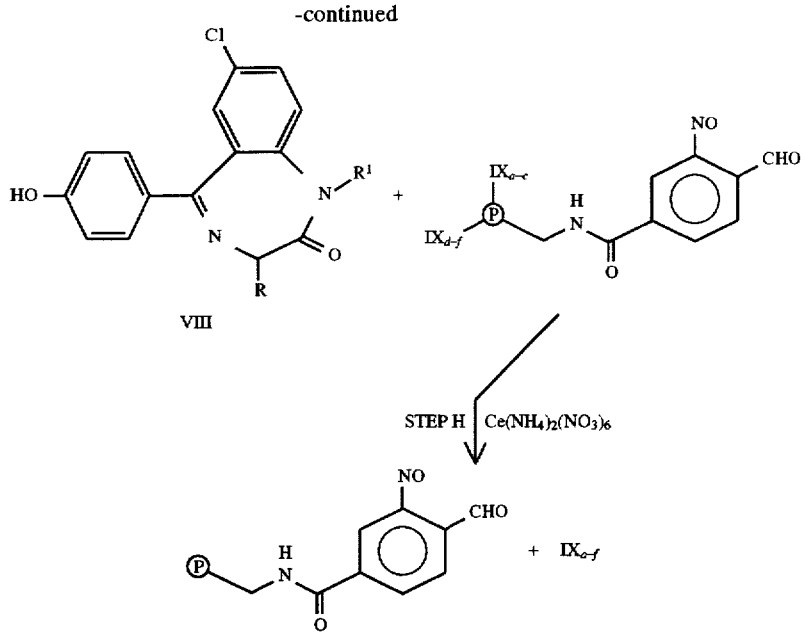

The benzodiazepines VIII are constructed on polystyrene beads similarly to the method of Bunin and Ellman (JACS, 114, 10997–10998 [1992]) except that a photolabile linker is incorporated between the bead and the benzodiazepine (see steps A, B, and C), thus allowing the benzodiazepine to be removed in step G non-hydrolytically by exposure to U.V. light (350 nm in DMF for 10 minutes to 12 hr). Additionally, binary codes are introduced in steps D and E which allow for a precise determination of the reaction sequence used to introduce each of the 6 R's and 5 $R^1$'s. After removal of the tags according to step H and analysis by electron capture detection following GC separation, the nature of the individual R and $R^1$ groups is determined.

Steps D, E, and F essentially follow the procedure of Bunin and Ellman, but also include the incorporation of identifiers IXa–c in step D and IXd–f in Step E. The identifiers are all represented by Formula IX,

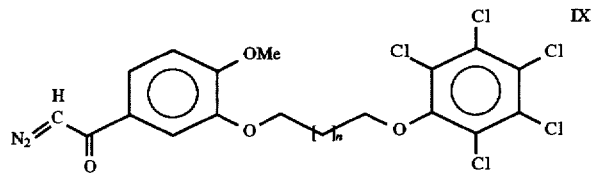

wherein:

$IX_a$ indicates n=6;

$IX_b$ indicates n=5;

$IX_c$ indicates n=4;

$IX_d$ indicates n=3;

$IX_e$ indicates n=2; and $IX_f$ indicates n=1.

The codes for each of R and $R^1$ are as follows:

TABLE 4-1

| IX | R |
|---|---|
| a | $CH_3$ |
| b | $CH(CH_3)_2$ |
| a,b | $CH_2CO_2H$ |
| c | $(CH_2)_4NH_2$ |
| a,c | $CH_2-C_6H_4$-4-OH |
| b,c | $CH_2C_6H_5$ |
| IX | $R^1$ |
| d | H |
| e | $CH_3$ |
| d,e | $C_2H_5$ |
| f | $CH_2CH=CH_2$ |
| d,f | $CH_2C_6H_5$ |

Step A

To a solution of I (1 equiv) in toluene (conc.=0.5M) is added the Fmoc protected 2-amino-5-chloro-4'-hydroxybenzophenone (1.3 eq) and diethylazaodicarboxylate (1.3 eq) and triphenylphosphine (1.3 eq). The mixture is stirred at room temperature for 24 hr. The solvent is removed in vacuo and the residue triturated with ether and filtered and the solvent again removed in vacuo. The resultant product II is purified by chromatography on silica gel.

Step B

To a solution of II in DCM (0.2M) stirring at r.t. is added TFA (3 equiv.) and the solution is allowed to stir for 12 hr. The solution is evaporated to dryness in vacuo and the residue dissolved in DCM, washed once with brine and dried ($Na_2SO_4$). Filtration and evaporation of the solvent affords III.

Step C

1% DVB (divinylbenzene) cross-linked polystyrene beads (50μ) functionalized with aminomethyl groups (1.1 mEq/g) are suspended in DMF in a peptide reaction vessel (Merrifield vessel). III (2 equiv) and HOBt (3 equiv) in DMF are added and the vessel shaken for 10 min. DIC (3 eq) is added and the vessel is shaken until a negative Ninhydrin test indicates completion of the reaction after 12 hr.

The DMF is removed and the resin washed with additional DMF (x5) and DCM (x5) before drying in vacuo.

Step D

The dry resin is divided into 6 reaction vessels and is suspended in DCM. The appropriate combinations of identifiers $IX_{a-c}$ (see Table 4-1) are added to the flasks and shaken for 1 hr. The Rh(TFA)$_2$ catalyst (1 mol %) is added to each flask and shaken for an additional 2 hr. The flasks are drained and the resin washed with DCM (x5). The resin is then treated with a solution of TFA in DCM (0.01M) and shaken for 30 min. and then washed again with DCM (x3) followed by DMF (x2). The resin is treated with a 20% solution of piperidine in DMF and shaken for 30 min. and is then washed with DMF (x3) and DCM (x3).

To each flask is added the appropriate Fmoc protected amino acylfluoride (3 equiv) (when required side-chain functional groups are protected as tert-butyl ester (Asp), tert-butyl ether (Tyr) or tert-butyloxycarbonyl (Lys)) with 2,6-di-tert-butyl-4-methylpyridine (10 equiv) and the flasks shaken overnight or until a negative Ninhydrin test is achieved. The resin is washed once (DCM) and then the six batches are combined and washed again (DCM, x5) before drying in vacuo.

Step E

The dry resin is divided into five reaction vessels and is suspended in DCM. The appropriate combinations of identifiers $IX_{d-f}$ (see Table 4-1) are added to the flasks, and shaken for 1 hr. The Rh(TFA)$_2$ catalyst (1 mol %) is added to each flask and shaken for an additional 2 hr. The flasks are drained and the resin washed with DCM (x5). The resin in then treated with a solution of TFA in DCM (0.01M) and shaken for 30 min. and is then washed with DMF (x3) and DCM (x3).

To each flask is added a solution of 5% acetic acid in DMF and the mixtures are heated to 60° C. and shaken overnight. The solvent is drained and then the resin washed with DMF (x5).

Step F

Each batch of resin is suspended in THF and the flasks are cooled to −78° C. To each flask is added a solution of lithiated 5-(phenylmethyl)-2-oxazolidinone (2 equiv) in THF and the mixtures are shaken at −78° C. for 1 hr. The appropriate alkylating agent (Table 4-2) (4 equiv) is then added to each reaction flask followed by a catalytic amount of DMF. The vessels are allowed to warm to ambient temperature and shaken at this temperature for 5 hrs. The solvent is removed by filtration and the resin washed with THF (x1) and then dried in vacuo. The batches of resin are then combined and washed with THF (x2) and DCM (x2) and the combined resin is then treated with a 95:5:10 mixture of TFA:water:dimethylsulphide for 2 hrs to remove the side chain protecting groups.

TABLE 4-2

| IDENTIFIER | ALKYLATING AGENT |
|---|---|
| e | H$_3$CI |
| d,e | C$_2$H$_5$Br |
| f | BrCH$_2$—CH=CH$_2$ |
| d,f | BrCH$_2$C$_6$H$_5$ |

Step G

The resultant benzodiazepine can be cleaved from a bead of polystyrene by suspending the bead in DMF and irradiating with U.V. (350 nm) for 12 hrs.

Step H

A bead of interest is placed into a glass capillary tube. Into the tube is syringed 1 µL of 1M aqueous cerium (IV) ammonium nitrate (CAN) solution, 1 µL of acetonitrile and 2 µL of hexane. The tube is flame sealed and then centrifuged to ensure that the bead is immersed in the reagents. The tube is placed in an ultrasonic bath and sonicated from 1 to 10 hrs preferably from 2 to 6 hrs. The tube is cracked open and ≅1 µL of the upper hexane layer is mixed with ≅0.2 µL of bis(trimethylsilyl)acetamide (BSA) prior to injection into the GC and each tag member determined using electron capture detection, as exemplified in the following scheme.

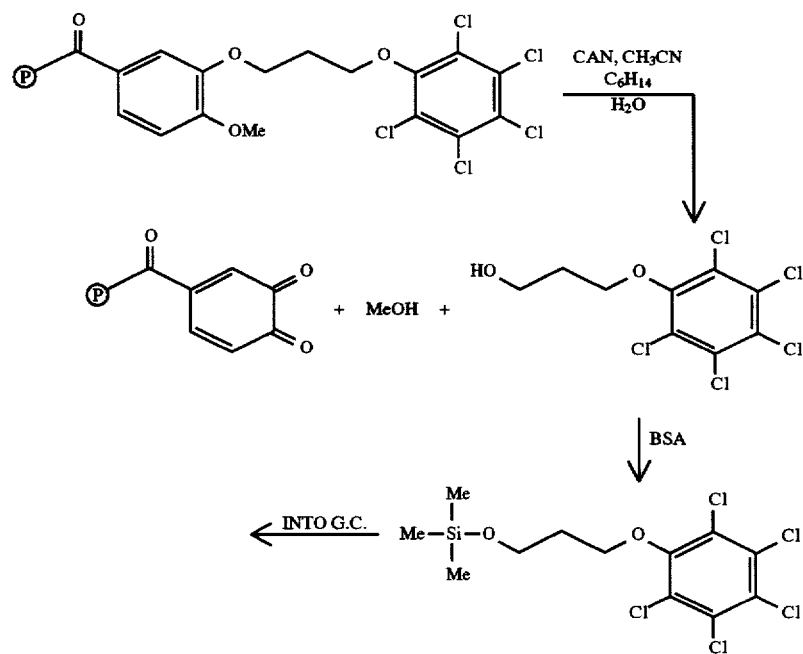

EXAMPLE 5

117,649 Peptide Library

An encoded library of 117,649 peptides was prepared. This library had the sequence H$_2$N-XXXXXXXEEDLGGGG-bead, where the variable residue X was D,E,I,K,L,Q or S. This library was encoded using the 18 tags as defined in Example 3; three binary bits being sufficient to represent the seven amino acids used in each step. The code was: 001=S; 010=I; 011=K; 100=L; 101=Q; 110=E; and 111=D, where 1 indicates the presence and 0 indicates the absence of a tag.

The constant segment of the library (H$_2$NEEDLGGGG-bead) was synthesized on 1.5 g of 50–80μ Merrifield polystyrene synthesis beads functionalized with 1.1 mEq/g of aminomethyl groups using standard solid phase methods based on t-Bu sidechain protection and Fmoc mainchain protection. After deprotecting the N-terminal Fmoc protecting group with diethylamine, the beads were divided into seven 200 mg portions, each portion being placed into a different Merrifield synthesis vessel mounted on a single wrist-action shaker.

The beads in the seven vessels were processed as in Table 3-1 to attach the sets of identifiers (T1–T3) and the corresponding amino acid to each portion except that instead of DIC, i-butylchloroformate was used for activation.

This procedure first chemically attached small amounts of appropriate identifiers via their carboxylic acids to the synthesis beads. This attachment was achieved by activating the linker carboxyl groups as mixed carbonic anhydrides using isobutylchloroformate, and then adding an amount of activated identifier corresponding to 1% of the free amino groups attached to the beads. Thus, about 1% of the free amino groups were terminated for each identifier added. The remaining free amino groups were then coupled in the usual way with the corresponding protected amino acids activated as their symmetrical anhydrides.

After washing, the seven portions were combined and the Fmoc protected amino groups were deprotected by treatment with diethylamine. The beads were again divided into seven portions and processed as before, except that the appropriate identifiers carrying tags T4, T5, and T6 were added to the reaction vessels.

The procedure of dividing, labelling, coupling the amino acid combining and main-chain deprotection was carried out a total of six times using identifiers bearing tags T1–T18, affording an encoded peptide library of 117,649 different members.

Typical Identifier Preparation

To a solution of 8-bromo-1-octanol (0.91 g, 4.35 mmol) and 2,4,6-trichlorophenol (1.03 g, 5.22 mmol) in DMF (5 mL) was added cesium carbonate (1.70 g, 5.22 mmol) resulting, in the evolution of gas and the precipitation of a white solid. The reaction was stirred at 80° C. for 2 hrs. The mixture was diluted with toluene (50 mL) and poured into a separatory funnel, washed with 0.5N NaOH (2×50 mL), 1N HCl (2×50 mL) and water (50 mL) and the organic phase was dried (MgSO$_4$). Removal of the solvent by evaporation gave 1.24 g (87% yield) of tag as a clear oil.

The above tag (0.81 g, 2.5 mmol) was added to a 2M solution of phosgene in toluene (15 mL) and stirred at room temperature for 1 hr. The excess phosgene and the toluene were removed by evaporation and the resulting crude chloroformate was dissolved in DCM (5 mL) and pyridine (0.61 mL, 7.5 mmol). tert-Butyl 4-hydroxymethyl-3-nitrobenzoate (Barany and Albericio, *J. Am. Chem. Soc.*, (1985), 107, 4936–4942) (0.5 g, 1.98 mmol) was added and the reaction mixture stirred at room temperature for 3 hrs. The solution was diluted with ethyl acetate (75 mL) and poured into a separatory funnel. After washing with 1N HCl (3×35 mL), saturated NaHCO$_3$ (2×35 mL) and brine (35 mL), the organic phase was dried (MgSO$_4$). The solvent was removed by evaporation and the residue purified by chromatography on silica gel (5% to 7.5% ethyl acetate in petroleum ether) affording 0.95 g (79% yield) of the identifier tert-butyl ester as a clear oil.

Trifluoroacetic acid (3 mL) was added to a solution of the identifier tert-butyl ester (0.95 g, 1.57 mmol) in DCM (30 mL) to deprotect the linker acid (i.e., F$^1$—F$^2$ of Formula I) and the solution was stirred at room temperature for 7 hrs. The mixture was then evaporated to dryness and the residue redissolved in DCM (30 mL). The solution was washed with brine (20 mL) and the organic phase dried (MgSO$_4$). Removal of the solvent by evaporation gave 0.75 g (87% yield) of the identifier (6B) as a pale yellow solid. (Tag nomenclature is the same as in Example 3).

Typical Encoded Library Synthesis Step

Nα-Fmoc-E(tBu)-E(tBu)-D(tBu)-L-G4-NH-resin was suspended in DMF (20 mL) and shaken for 2 min. After filtering, 1:1 diethylamine:DMF (40 mL) was added to remove the Fmoc protecting groups and the resin was shaken for 1 hr. The resin was separated by filtration and washed with DMF (2×20 mL, 2 min each); 2:1 dioxane: water (2×20 mL, 5 min each), DMF (3×20 mL, 2 min each), DCM (3×20 mL, 2 min each) then dried in vacuo at 25° C. (The resin was found to have 0.4 mmol/g amino groups by picric acid titration at this stage.)

150 mg Portions of the resin were placed into seven Merrifield vessels and suspended in DCM (5 mL). The appropriate identifiers were activated as their acyl carbonates as follows (for the first coupling): T1 (6.6 mg, 0.0098 mmol) was dissolved in anhydrous ether (2 mL) and pyridine (10 μL) was added. Isobutyl chloroformate (1.3 μL, 0.0096 mmol) was added as a solution in anhydrous ether (0.1 mL). The resulting mixture was stirred at 25° C. for 1 hr. during which time a fine white precipitate formed. The stirring was stopped and the precipitate was allowed to settle for 30 min. Solutions of the acylcarbonates of T2 and T3 were prepared in the same way. Aliquots (0.25 mL) of the supernatant solution of activated identifiers were mixed to give the appropriate 3-bit binary tag codes and the appropriate coding mixtures of identifiers were added to each of the seven synthesis vessels. The vessels were shaken in the dark for 12 hrs, and then each was washed with DCM (4×10 mL, 2 min each). A solution of the symmetrical anhydride of an Nα-Fmoc amino acid in DCM (3 equivalents in 10 mL) was then added to the corresponding coded batch of resin and shaken for 20 min. 5% N,N-diisopropylethylamine in DCM (1 mL) was added and the mixture shaken until the resin gave a negative Kaiser test.

The resin batches were filtered and combined, and then washed with DCM (4×20 mL, 2 min each), isopropanol (2×20 mL, 2 min each), DCM (4×20 mL, 2 min each). The next cycle of labelling/coupling was initiated by Fmoc deprotection as described above.

After Fmoc deprotection of the residues in the last position of the peptide, the side chain functionality was deprotected by suspending the resin in DCM (10 mL), adding thioanisole (2 mL), ethanedithiol (0.5 mL) and trifluoroacetic acid (10 mL) then shaking for 1 hr at 25° C. The resin was then washed with DCM (6×20 mL, 2 min each) and dried.

Electron Capture Gas Chromatography Reading of Code

A single, selected bead was placed in a Pyrex capillary tube and washed with DMF (5×10 μL). The bead was then suspended in DMF (1 µL) and the capillary was sealed. The suspended bead was irradiated at 366 nm for 3 hrs to release the tag alcohols, and the capillary tube subsequently placed in a sand bath at 90° C. for 2 hrs. The tube was opened and bis-trimethylsilyl acetamide (0.1 mL) was added to trimethylsilylate the tag alcohols. After centrifuging for 2 min., the tag solution above the bead (1 µL) was injected directly into an electron capture detection, capillary gas chromatograph for analysis. Gas chromatography was performed using a Hewlett Packard Series II Model 5890 gas chromatograph equipped with a 0.2 mm×20 m methylsilicone fused silica capillary column and an electron capture detector. Photolysis reactions were performed using a UVP "Black Ray" model UVL 56 hand-held 366 nm lamp.

Antibody Affinity Methods

The anti-C-myc peptide monoclonal antibody 9E10 was prepared from ascites fluid as described in Evans et al., Mol. Cell Biol., 5, 3610–3616 (1985) and Munro and Pelham, Cell, 48, 899–907 (1987). To test beads for binding to 9E10, beads were incubated in TBST (20 mM Tris-HCl (pH 7.5), 500 mM NaCl and 0.05% Tween-20) containing 1% bovine serum albumin (BSA) to block non-specific protein binding sites. The beads were then centrifuged, resuspended in a 1:200 dilution of 9E10 ascites fluid in TBST+1% BSA and incubated overnight at 4° C. Beads were subsequently washed three times in TBST and incubated for 90 min. at room temperature in alkaline phosphatase-coupled goat anti-mouse IgG antibodies (Bio-Rad Laboratories), diluted 1:3000 in TBST+1% BSA. After washing the beads twice in TBST and once in phosphatase buffer (100 mM Tris-HCl, pH 9.5, 100 mM NaCl and 5 mM $MgCl_2$), the beads were incubated 1 hr at room temperature in phosphatase buffer containing one one-hundreth part each of AP Color Reagents A & B (Bio-Rad Laboratories). To stop the reaction, the beads were washed twice in 20 mM sodium EDTA, pH 7.4. Solution phase affinities between 9E10 and various peptides were determined by a modification of the competitive ELISA assay described by Harlow et al., Antibodies: a Laboratory Manual, 570–573, Cold Spring Harbor Press, Cold Spring Harbor, N.Y.

From a 30 mg sample of the combinatorial library of peptides, 40 individual beads were identified which stained on exposure to the anti-C-myc monoclonal antibody. Decoding of these positive-reacting beads established the ligand's reaction sequence as the myc epitope (EQKLISEEDL) or sequences that differed by one or two substituents among the three N-terminal residues.

EXAMPLE 6

23,540,625 Mixed Amide Library

The encoding technique was tested further by the preparation of a combinatorial library of 23,540,625 members consisting of peptides and other amide compounds.

The synthesis was carried out using 15 different reagents in 5 steps and 31 different reagents in the sixth step. Four identifiers were used to encode each of the 5 steps with 15 reagents and five identifiers were used in the final step with 31 reagents. A label set of 25 identifiers was therefore prepared. 2-Nitro-4-carboxybenzyl, O-aryl substituted ω-hydroxyalkyl carbonate identifiers were employed, where the tag components were comprised of an alkyl moiety of from 3 to 12 carbon atoms and the aryl moieties were (A) pentachlorophenyl, (B) 2,4,5-trichlorophenyl, (C) 2,4,6-trichlorophenyl, or (D) 2,6-dichloro-4-fluorophenyl. A set of 25 tags was prepared using appropriate alkyl chains lengths with A, B, C or D, separable using a 0.2 mM×25M methylsilicone GC column. The chemical compositions of tags T1–T25 (where T1 represents the tag with the longest retention time, and T25 the tag with the shortest retention time) are summarized below:

| T1 | 10A | T6  | 10C | T11 | 7B | T16 | 5C | T21 | 2B |
| T2 | 9A  | T7  | 9B  | T12 | 7C | T17 | 4B | T22 | 2C |
| T3 | 8A  | T8  | 9C  | T13 | 6B | T18 | 4C | T23 | 1B |
| T4 | 7A  | T9  | 8B  | T14 | 6C | T19 | 3B | T24 | 1C |
| T5 | 10B | T10 | 8C  | T15 | 5B | T20 | 3C | T25 | 2D |

The designations 10A, 9A, etc. are as described in Example 3.

The fifteen reagents used in the first five stages and the code identifying them are represented below where 1 represents the presence of tag and 0 the absence thereof.

| REAGENT | CODE |
| --- | --- |
| L-serine | (0001) |
| D-serine | (0010) |
| L-glutamic acid | (0011) |
| D-glutamic acid | (0100) |
| L-glutamine | (0101) |
| D-glutamine | (0110) |
| L-lysine | (0111) |
| D-lysine | (1000) |
| L-Proline | (1001) |
| D-Proline | (1010) |
| L-phenylalanine | (1011) |
| D-phenylalanine | (1100) |
| 3-amino-benzoic acid | (1101) |
| 4-aminophenyl acetic acid | (1110) |
| 3,5-diamino-benzoic acid | (1111) |

The 31 reagents and the code representing them in the sixth stage are represented below:

| REAGENT | CODE |
| --- | --- |
| L-serine | (00001) |
| D-serine | (00010) |
| L-glutamic acid | (00011) |
| D-glutamic acid | (00100) |
| L-glutamine | (00101) |
| D-glutamine | (00110) |
| L-lysine | (00111) |
| D-lysine | (01000) |
| L-proline | (01001) |
| D-proline | (01010) |
| L-phenylalanine | (01011) |
| D-phenylalanine | (01100) |
| 3-amino-benzoic acid | (01101) |
| 4-aminophenyl acetic acid | (01110) |
| 3,5-diamino-benzoic acid | (01111) |
| Succinic Anhydride | (10000) |
| Tiglic acid | (10001) |
| 2-pyrazine carboxylic acid | (10010) |
| (±)thioctic acid | (10011) |
| 1-piperidinepropionic acid | (10100) |
| piperonylic acid | (10101) |
| 6-methylnicotinic acid | (10110) |
| 3-(2-thienyl)acrylic acid | (10111) |
| methyl iodide | (11000) |
| tosyl chloride | (11001) |
| p-toluenesulfonyl isocyanate | (11010) |
| 3-cyanobenzoic acid | (11011) |
| phthallic anhydride | (11100) |

| REAGENT | CODE |
|---|---|
| acetic anhydride | (11101) |
| ethyl chloroformate | (11110) |
| mesylchloride | (11111) |

A spacer of six glycine units was prepared on the beads using standard methods. The variable region was constructed using butyl sidechain protection, and amino groups were protected as Fmoc derivatives. Amide bonds were formed by activation of the carboxylic acid with DIC and HOBt.

EXAMPLE 7

Hetero-Diels-Alder Library

A combinatorial hetero Diels-Alder library comprising 42 compounds of the formula:

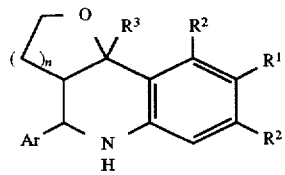

wherein;
$R^1$ is H, $CH_3O$, $F_3C$, $F_3CO$, $H_5C_6O$, or $C_6H_{11}$;
$R^2$ is H, $CH_3$, or $CH_3O$;
$R^3$ is H (when n=2), or $CH_3$ (when n=1); and

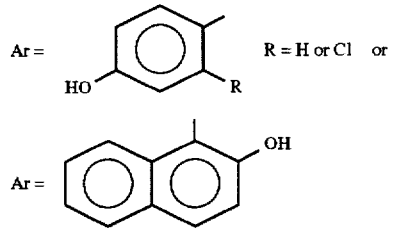

was constructed per the following scheme:

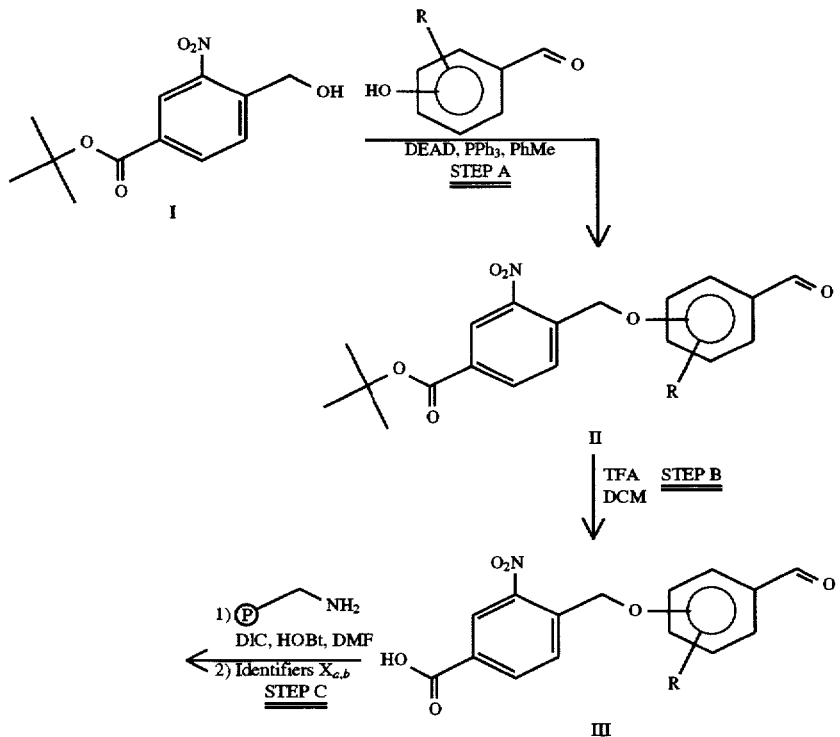

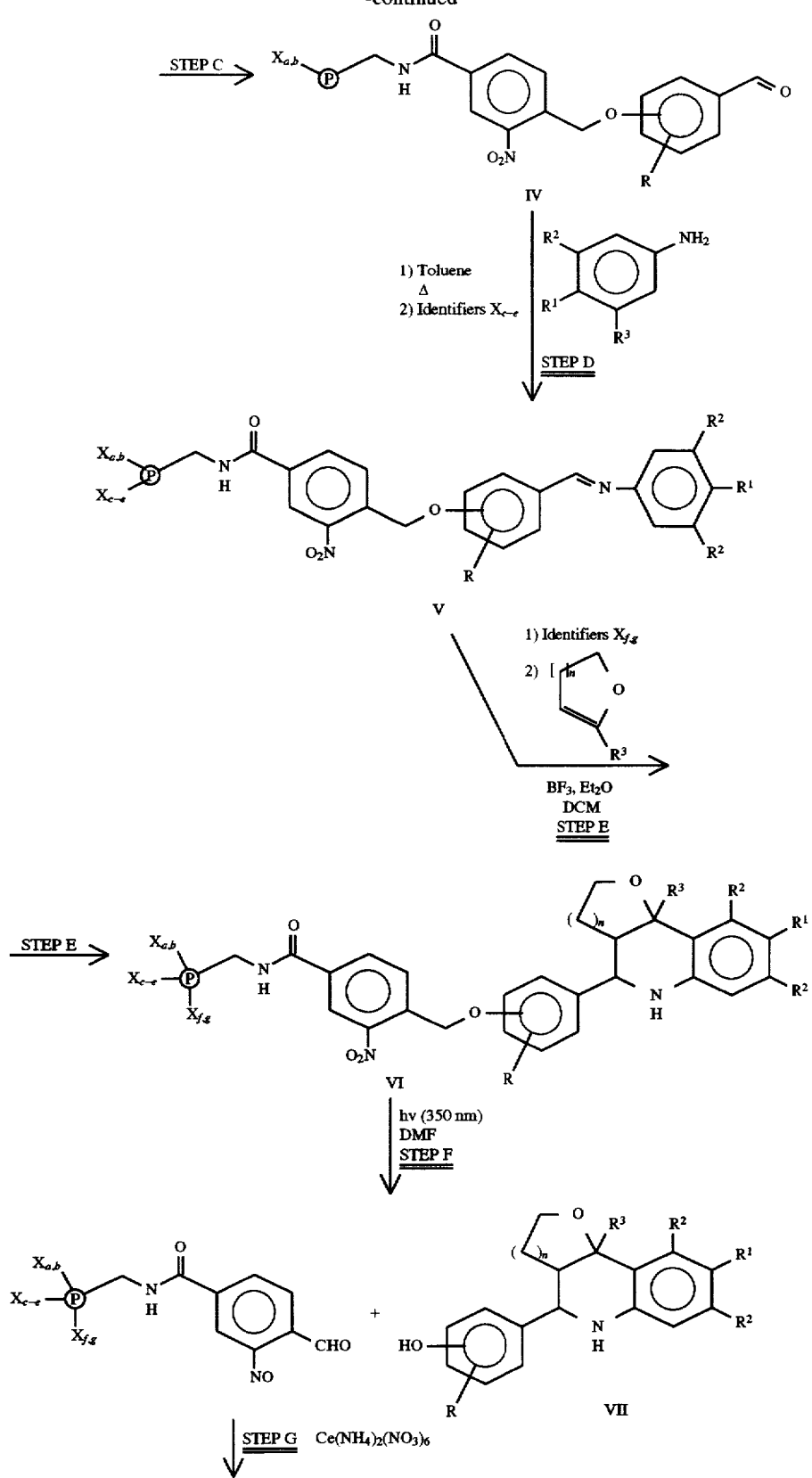

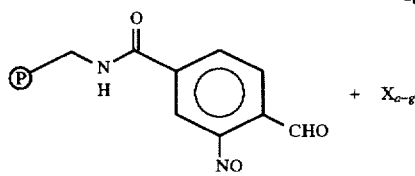 + X<sub>c-g</sub>

The azatricyclic products (VI) were constructed on polystyrene beads and were linked to the beads by a photocleavable linker allowing the azatricycle (VII) to be removed from the bead by exposure to U.V. light (350 nm in DMF). The binary codes introduced in steps C,D and E allow a unique determination of the reaction sequence used to introduce ArR, $R^1$, $R^2$ and $R^3$. The encoding tags were removed according to step G and analyzed by electron capture detection following GC separation.

The identifiers used in this scheme are represented by the formula X:

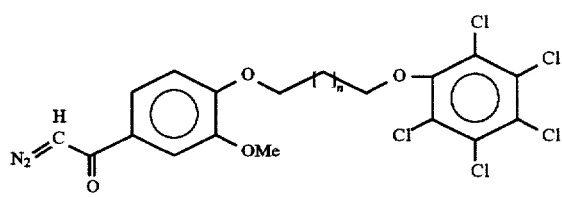

Wherein;

$X_a$ indicates n=10
$X_b$ indicates n=9
$X_c$ indicates n=8
$X_d$ indicates n=7
$X_e$ indicates n=6
$X_f$ indicates n=5
$X_g$ indicates n=4

The codes for each of R, $R^1$, $R^2$, $R^3$ are as follows:

TABLE 7-1

| X | | | |
|---|---|---|---|
| a | Ar = (HO-phenyl-R) | | R = E |
| b | Ar = (HO-phenyl-R) | | R = Cl |
| a, b | Ar = naphthyl-OH | | |
| c | $R^1 = H$ | | $R^2 = H$ |
| d | $R^1 = H$ | | $R^2 = CH_3$ |
| d, c | $R^1 = OCH_3$ | | $R^2 = OCH_3$ |
| e | $R^1 = CF_3$ | | $R^2 = H$ |
| e, c | $R^1 = C_6H_5O$ | | $R^2 = H$ |
| e, d | $R^1 = F_3CO$ | | $R^2 = H$ |

TABLE 7-1-continued

| X | | | |
|---|---|---|---|
| e, d, c | $R^1 = C_6H_{11}$ | | $R^2 = H$ |
| f | $R^3 = CH_3$ | | n = 1 |
| g | $R^3 = H$ | | n = 2 |

Step A

To a solution of I (2.03 g, 8 mmol), 4-hydroxybenzaldehyde (1.17 g, 9.6 mmol) and triphenylphosphine (2.73 g, 10.4 mmol) in toluene (20 mL) stirring at 0° C. was added over a period of 30 minutes diethylazodicarboxylate. The solution was allowed to warm and stirred for 1 hour once ambient temperature had been reached. The solution was concentrated by removal of approximately half of the solvent in vacuo and was then triturated with ether. The mixture was then filtered and the residue was washed thoroughly with ether. The solvent was removed in vacuo and the residue was purified by chromatography on silica gel (15% ethyl acetate in hexane) affording 1.3 g of the ether IIa (47% yield).

2-chloro-4-hydroxybenzaldehyde and 2-hydroxy-1-naphthaldehyde were coupled to I in analogous fashion affording ethers IIb and c in yields of 91% and 67%, respectively.

Step B

To a solution of ether IIa (0.407 g, 1.14 mmol) in DCM (20 mL) stirring at room temperature was added TFA (8 mL). The solution was allowed to stir for 6 hrs. The solution was evaporated to dryness in vacuo affording 0.343 g of acid IIIa (100% yield). Ethers IIb and IIc were deprotected analogously affording acids IIIb and c in yields of 92% and 100% respectively.

Step C

Into a peptide reaction vessel (Merrifield vessel) were measured 1% DVB (divinylbenzene) cross-linked polystyrene beads (50–80μ) functionalized with aminomethyl groups (1.1 meq/g) (200 mg of resin). The resin was suspended in DMF (2 mL) and shaken for 20 min. The acid IIIa (38 mg, 2 equiv.), 1-hydroxybenzotriazole (40 mg, 2 equiv) and diisopropylcarbodiimide (38 mg, 2 equiv) were added and the mixture shaken until a negative Ninhydrin test was achieved (22 hr). The solution was removed by filtration and the resin was washed with DCM (8×10 mL).

The resin was resuspended in DCM (5 mL), identifier Xa (15 mg) was added and the flask was shaken for 1 hr. Rh(TFA)₂ catalyst (1 mol %) was added and the flasks shaken for 2 hrs. The solvent was removed by filtration and the resin resuspended in DCM (5 mL). Trifluoroacetic acid (1 drop) was added and the vessel shaken for 20 min. The solvent was removed by filtration, and the resin was washed with DCM (8×10 mL).

In an analogous fashion, acids IIIb and IIIc were attached to the resin and were encoded with the appropriate identifiers, i.e., Xb for acid IIIb and Xa and Xb for acid IIIc. The three batches of resin were combined, mixed, washed, and dried.

Step D

The dry resin was divided into 7 equal portions (87 mg) which were put into seven peptide reaction vessels (Merrifield vessels) which were wrapped with heat tape. The resin in each vessel was suspended in toluene (10 mL) and shaken for 20 min. An appropriate amount of one aniline was then added to each flask (see Table 7-2).

TABLE 7-2

| FLASK | ANILINE | AMOUNT ADDED |
|---|---|---|
| 1 | Aniline | 3 mL |
| 2 | 3,5-dimethylaniline | 3 mL |
| 3 | 3,4,5-trimethoxyaniline | 2 g |
| 4 | 4-trifluoromethylaniline | 3 mL |
| 5 | 4-phenoxyaniline | 2 g |
| 6 | 4-trifluoromethoxyaniline | 3 mL |
| 7 | 4-cyclohexylaniline | 2 g |

The heating tape was connected and the reaction mixtures shaken at 70° C. for 18 hrs. The heat tape was disconnected and the solvent was removed by filtration and each batch of resin was washed with dry DCM (4×10 mL), ether (10 mL), toluene (10 mL) and DCM (2×10 mL). Each of the portions was then suspended in DCM (5 mL) and to each flask was added the appropriate identifier or combination of identifiers (Xc–e) (15 mg) (see Table 7-1). The flasks were shaken for 1 hr. and then Rh(TFA)$_2$ (1 mol %) was added to each flask and shaking continued for 2 hrs.

The solvent was then removed and each batch of resin was re-suspended in DCM (5 mL) to which was added TFA (1 drop). This mixture was shaken for 20 min., then the solvent was removed by filtration. The batches of resin were then washed (DCM, 1×10 mL) and combined, washed again with DCM (3×10 mL) and then dried thoroughly in vacuo.

Step E

The dried resin was divided into two equal portions (0.3 g) and each was placed in a peptide reaction vessel. The resin batches were washed with DCM (2×10 mL) and then resuspended in DCM (5 mL). To one flask was added the identifier Xf (15 mg) and to the other was added Xg (15 mg). The flasks were shaken for 1 hr. prior to the addition of Rh(TFA)$_2$ catalyst (1 mol %). The flasks were shaken for 2 hrs. and then the solvent was removed by filtration. Each batch of resin was washed with DCM (3×10 mL), and each was then resuspended in DCM (5 mL).

The appropriate enol ether (1 mL) (see Table 7-1) was added to the flasks and the vessels shaken for 30 min. To each flask was added a solution of BF$_3$.OEt$_2$ (0.5 mL of a 5% solution in DCM) and the flasks were shaken for 24 hrs. Removal of the solvent by filtration was followed by washing of the resin with DCM (10 mL) and the resin was then combined. The beads were then washed further with DCM (5×10 mL), DMF (2×10 mL) methanol (2×10 mL) and DCM (2×10 mL). The resin was then dried thoroughly in vacuo.

Step F

To confirm the identity of the products produced in the Hetero-Diels-Alder library one example was completed on a large scale to allow confirmation of the structure by spectroscopic means. The procedure followed was essentially the same method as described for the combinatorial library. In step A 4-hydroxybenzaldehyde was coupled to the photolabile group. In step D, aniline was condensed with the aldehyde. In step E, the enol ether was formed with 4,5-dihydro-2-methylfuran.

The photolysis of the compound (step F) was performed by suspending 100 mg of the beads in DMF (0.3 mL) and irradiating the beads with UVP "Black Ray" model UVL 56 hand-held 366 nm lamp for 16 hrs. The DMF was removed to one side by pipette and the beads rinsed with additional DMF (2×3 mL). The original solution and the washings were combined and the solvent removed in vacuo. NMR analysis of the reaction mixture showed it to contain the desired azatricycle by comparison to the authentic sample.

Step G

A bead of interest was placed into a pyrex glass capillary tube sealed at one end. A solution (1 µL) of 1M aqueous cerium (IV) ammonium nitrate and acetonitrile (1:1) was syringed into the tube, and the tube was then centrifuged so that the bead lay on the bottom of the capillary and was completely immersed by the reagent solution. Hexane (2 µL) was added by syringe and the tube was again centrifuged. The open end of the capillary was flame-sealed and placed in an ultrasonic bath for 4 hrs. The capillary was then placed inverted into a centrifuge and spun such that the aqueous layer was forced through the hexane layer to the bottom of the tube. This extraction process was repeated 3 or 4 times and the tube was then opened. The hexane layer (1.5 µL) was removed by syringe and placed into a different capillary containing BSA (0.2 µL). This tube was sealed and centrifuged until the reagents were thoroughly mixed. A portion of the solution (ca. 1 µL) was removed and injected into a gas chromatography machine with a 25M×0.2 mM methylsilicone fused silica column with electron capture detection for separation and interpretation of the tag molecules.

The sample was injected onto the GC column at 200° C. and 25 psi of carrier gas (He$_2$). After 1 minute the temperature was increased at a rate of 20° C. per minute to 320° C., and the pressure was increased at a rate of 2 psi per minute to 40 psi. These conditions are shown in the following diagram:

GC CONDITIONS

TEMPERATURE

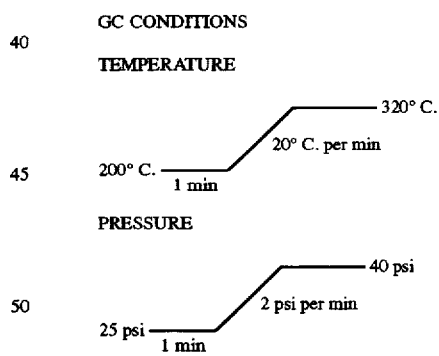

PRESSURE

The following results were obtained with four randomly selected beads:

| Bead 1 | | | |
|---|---|---|---|
| TAG DETECTED | | | |
| Xf | Xe Xd Xc | | Xb Xa |
| Ar | | | 2-Hydroxy naphthyl |
| R$^1$ | | C$_6$H$_{11}$ | |
| R$^2$ | | H | |
| R$^3$ | CH$_3$ (n = 1) | | |

-continued

Bead 2

| | TAG DETECTED | | |
|---|---|---|---|
| Xg | Xe Xd Xc | | Xb |

| Ar | | | 2-chloro-4-hydroxyphenyl |
| $R^1$ | $C_6H_{11}$ | | |
| $R^2$ | H | | |
| $R^3$ | H (n = 2) | | |

Bead 3

| | TAG DETECTED | | |
|---|---|---|---|
| Xg | Xe Xd | | Xb Xa |

| Ar | | | 2-Hydroxy naphthyl |
| $R^1$ | $F_3CO$ | | |
| $R^2$ | H | | |
| $R^3$ | H (n = 2) | | |

Bead 4

| | TAG DETECTED | | |
|---|---|---|---|
| Xf | Xe Xd | | Xb |

| Ar | | | 2-chloro-4-hydroxyphenyl |
| $R^1$ | $F_3CO$ | | |
| $R^2$ | H | | |
| $R^3$ | $CH_3$ (n = 1) | | |

EXAMPLE 8

Benzodiazepine Library

Following the procedure of Example 4, a combinatorial library is constructed of the Formula X

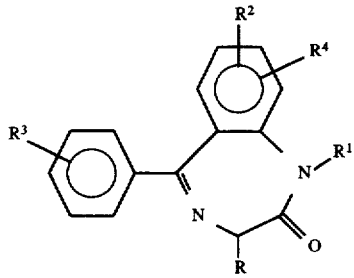

X wherein

R is a radical of a naturally occurring D or L amino acid;

$R^1$ is H, $C_1$–$C_6$ alkyl, lower alkenyl, $C_1$–$C_6$ alkylamine, carboxy $C_1$–$C_6$ alkyl, or phenyl $C_1$–$C_6$ alkyl wherein the phenyl is optionally substituted by lower alkyl, F, Cl, Br, OH, $NH_2$, $CO_2H$, or O-lower alkyl;

$R^2$ is H or $CO_2H$;

$R^3$ is H or OH;

$R^4$ is H or Cl;

with the provisos that when $R^3$ is OH, $R^2$ is H and when $R^2$ is carboxy, $R^3$ is H.

This library is released from a plurality of encoded beads of the general formula

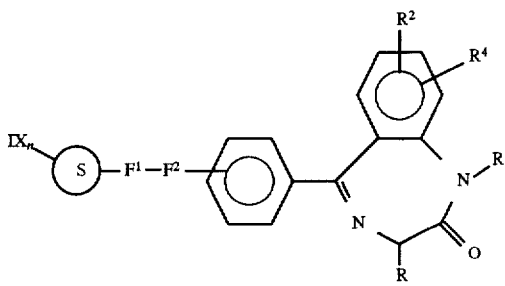

wherein $IX_n$ is a plurality of identifiers of the Formula Ia wherein said plurality represents an encoded scheme;

S is a substrate;

$F^{1'}$—$F^2$ is the residue of the linker member of Formula Ia; and

R, $R^1$, $R^2$, and $R_4$ are as defined for Formula X.

EXAMPLE 9

Typical Identifier Preparations

The diazo compound identifiers which are attached to the resin via carbene formation are prepared as exemplified.

Compounds of the general formula

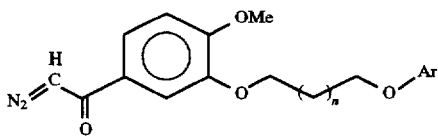

wherein n is 0–10 and

Ar is pentachlorophenol, 2,4,6-trichlorophenol, 2,4,5-trichlorophenol, or 2,6-dichloro-4-fluorophenol are prepared as follows.

To a solution of 1-hydroxy-4-(2,6-dichloro-4-fluorophenoxy)butane (0.38 g, 1.5 mmol), isovanillin (0.228 g, 1.5 mmol) and triphenylphosphine (0.393 g, 1.5 mmol) in THF (8 mL) was added diethylazodicarboxylate (0.287 g, 1.7 mmol). The solution stirred at r.t. for 36 hrs. The solvent was removed in vacuo and the residue purified by chromatography on silica gel (with a mixture of 20% ethyl acetate and 80% petroleum ether) affording 0.45 g of the aldehyde (77% yield).

The aldehyde (100 mg, 0.26 mmol) was dissolved in acetone (8 mL) and was treated with a solution of $KMnO_4$ (61 mg, 0.39 mmol) in acetone (4 mL) and water (4 mL). The reaction stirred at room temperature for 13 hrs. The mixture was diluted with ethyl acetate (100 mL) and water (50 mL) and the layers were separated. The aqueous layer was extracted with additional ethyl acetate (2×100 mL). The combined organic layers were washed with water (50 mL) and dried ($MgSO_4$). Removal of the solvent afforded 109 mg of the benzoic acid (93% yield).

A solution of the acid (76 mg, 0.188 mmol) in methylene chloride (2 mL) was treated with oxalylchloride (36 mg, 0.28 mmol) and catalytic DMF. After stirring for 10 min at room temperature slow but steady evolution of gas was observed. Stirring continued for 2 hrs. when the solution was diluted with DCM (15 mL) and washed with saturated aqueous sodium hydrogencarbonate solution (5 mL). The layers were separated. The organic layer was dried (Na$_2$SO$_4$) and the solvent evaporated affording the benzoyl chloride as pale yellow crystals.

The benzoyl chloride was dissolved in methylene chloride (5 mL) and was added to a stirring solution of diazomethane in ether at −78° C. The cold bath was allowed to warm up and the mixture allowed to stir for 5 hrs at room temperature. The solvents and excess diazomethane were removed in vacuo and the residue purified by chromatography on silica gel using gradient elution method where the concentration of ethyl acetate ranged from 10% to 40% in hexanes affording 48 mg of the diazo compound (60% yield).

Compounds of the general formula:

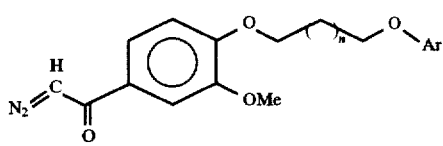

wherein;

n is 0–10 and

Ar is pentachlorophenol, 2,4,6-trichlorophenol, 2,4,5-trichlorophenol, or 2,6-dichloro-4-fluorophenol are prepared as follows.

Methyl vanillate (0.729 g, 4.0 mmole), 1-hydroxy-9-(2,3,4,5,6-pentachlorophenoxy)nonane (1.634 g, 4.0 mmole) and triphenylphosphine (1.259 g, 4.8 mmole) were dissolved in 20 mL dry toluene under argon. DEAD (0.76 mL, 0.836 g, 4.8 mmole) was added dropwise, and the mixture was stirred at 25° C. for one hour. The solution was concentrated to half volume and purified by flash chromatography eluting with DCM to give 1.0 g (1.7 mmole, 43%) of the product as a white crystalline solid.

The methyl ester above (1.0 g, 1.7 mmole) was dissolved in 50 mL THF, 2 mL water was added followed by lithium hydroxide (1.2 g, 50 mmole). The mixture was stirred at 25° C. for one hour then refluxed for five hours. After cooling to 25° C. the mixture was poured onto ethyl acetate (200 mL) and the solution was washed with 1M HCl (50 mL×3) then sat. aq. NaCl (1×50 mL) and dried over sodium sulfate. The solvent was removed and the crude acid azeotroped once with toluene.

The crude material above was dissolved in 100 mL toluene, 10 mL (1.63 g, 14 mmole) thionyl chloride was added, and the mixture was refluxed for 90 min. The volume of the solution was reduced to approximately 30 mL by distillation, then the remaining toluene removed by evaporation. The crude acid chloride was dissolved in 20 mL dry DCM and cooled to −78° C. under argon and a solution of approximately 10 mmole diazomethane in 50 mL anhydrous ether was added. The mixture was warmed to room temperature and stirred for 90 min. Argon was bubbled through the solution for 10 min. then the solvents were removed by evaporation and the crude material was purified by flash chromatography eluting with 10–20% ethyl acetate in hexane. The diazoketone (0.85 g, 1.4 mmole, 82% over three steps) was obtained as a pale yellow solid.

The following identifiers have been prepared as described above:

Photolabile Cleavage

50 Identifiers were prepared of the formula:

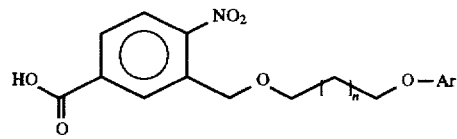

wherein:

Ar is

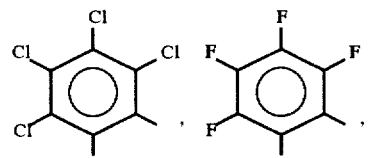

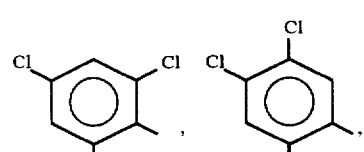

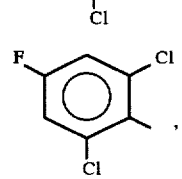

and n is 1,2,3,4,5,6,7,8,9, and 10.

Oxidative Cleavage Type I

7 Identifiers were prepared of the formula

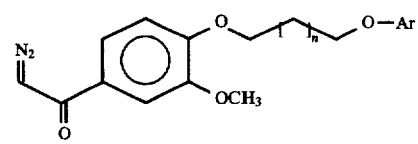

wherein:

Ar is

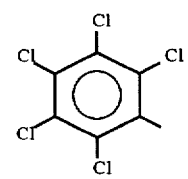

and n is 4,5,6,7,8,9, and 10.

Oxidative Cleavage Type II

13 Identifiers were prepared of the formula

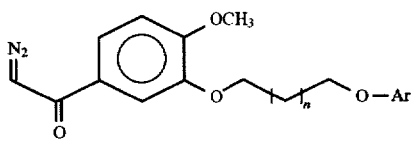

wherein:

Ar is

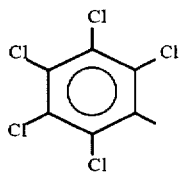

and n is 1,2,3,4,5,6,7,8,9,10;
and wherein:

Ar is

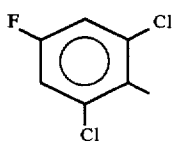

and n is 0,3, and 9.

EXAMPLE 10

Encoding Combinatorial Libraries with Tags Readable by Mass Spectroscopy

Figure 2:
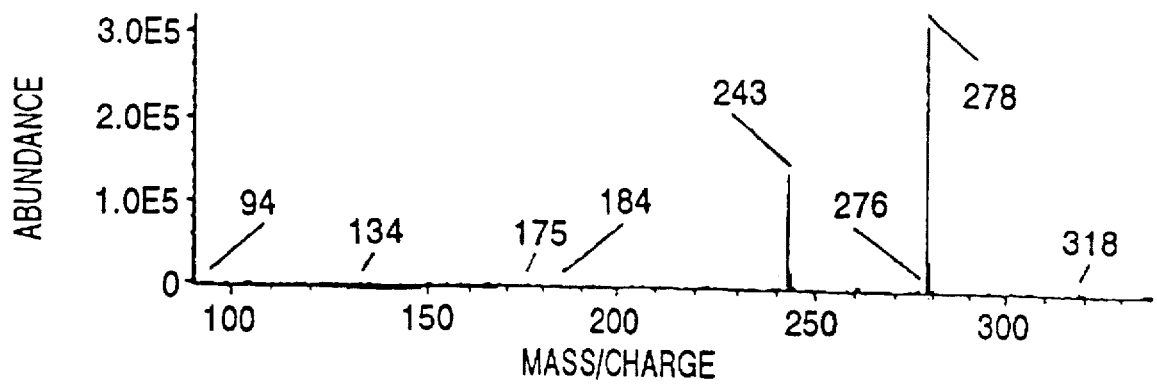
FIG. 2 illustrates the analysis of tag 11 by mass spectroscopy. Two signals corresponding to tag 11 were observed.
Figure 2:
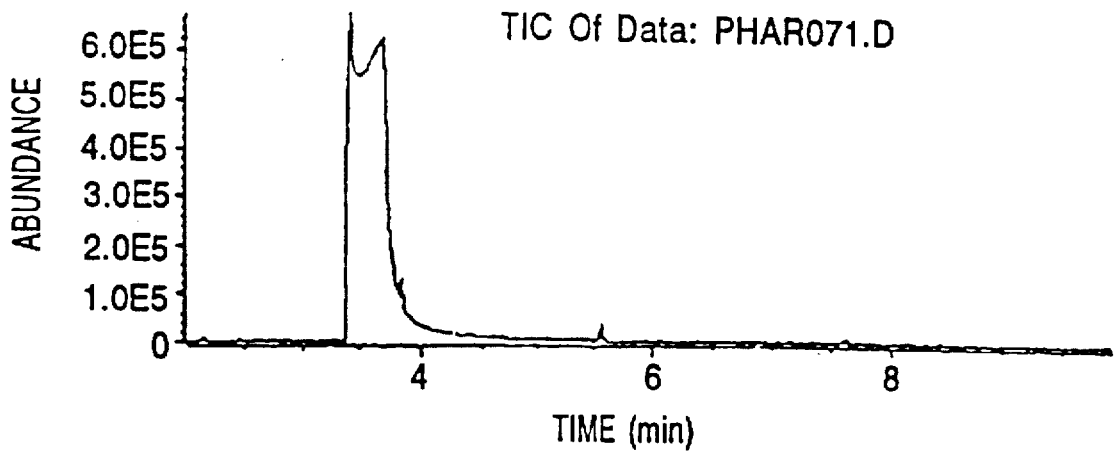
Figure 3:
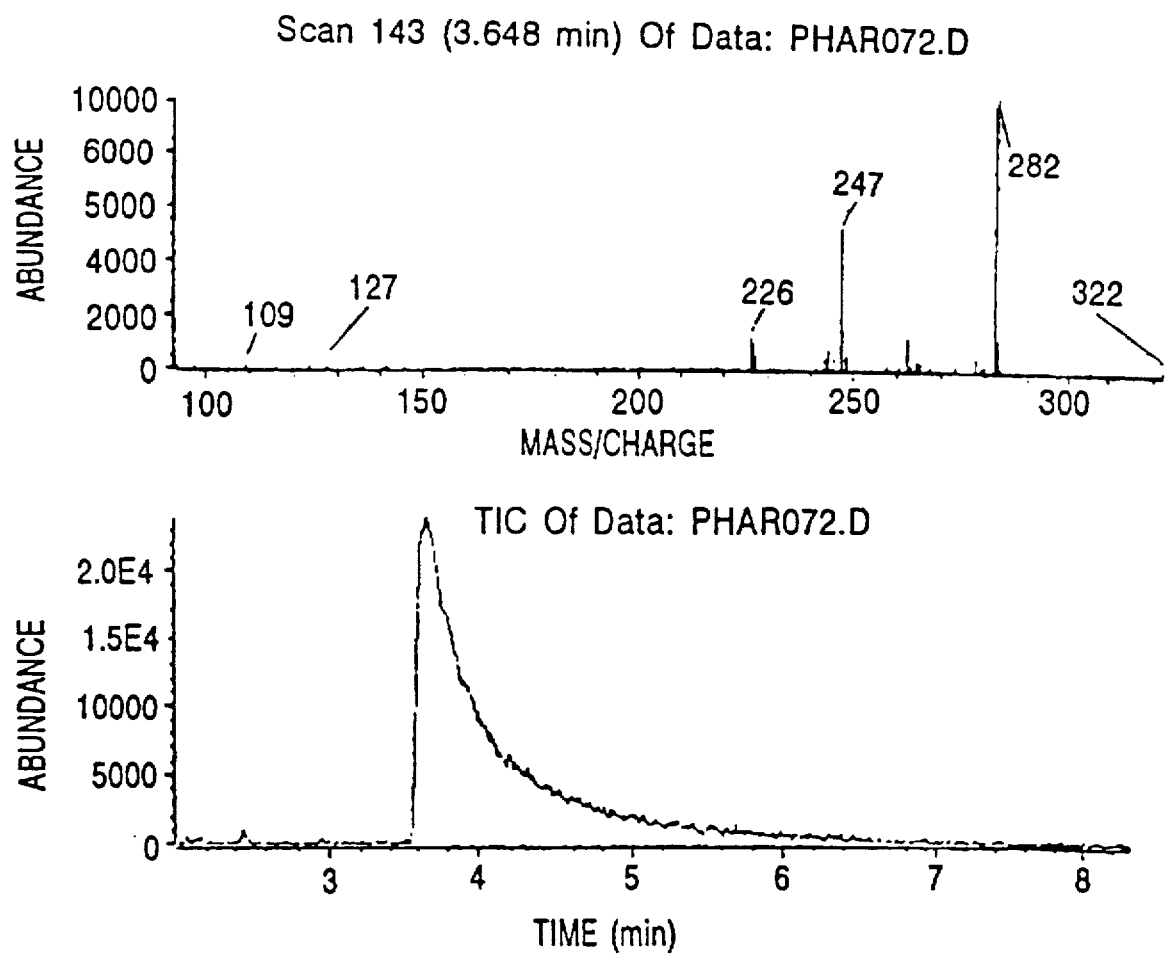
FIG. 3 illustrates the analysis of tag 13 by mass spectroscopy. Two signals corresponding to tag 13 were observed.
Figure 4:
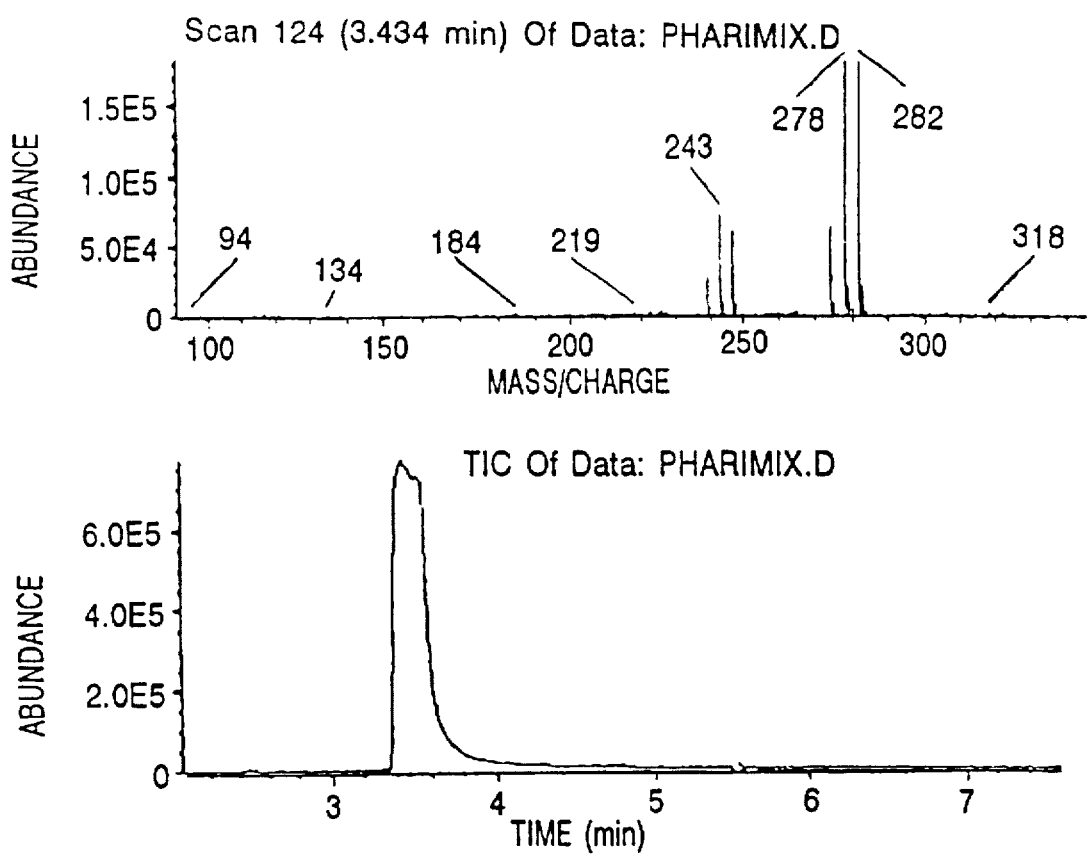
FIG. 4 illustrates the analysis of tags 4, 11 and 13 by positive chemical ionization mass spectroscopy (PCIMS) when approximately equal amounts of each tag were mixed together. Two signals corresponding to each separate tag could easily be distinguished.

The tags 4, 11 and 13 (Scheme 8) of the same structure, but different molecular weights due to varying deuterium substitution, were each synthesized (Schemes 9 and 10) and separately analyzed by mass spectroscopy (MS). Among MS techniques, positive chemical ionization mass spectroscopy (PCIMS) gave minimal fragmentation of the tag, such that only the molecular ion ([M+NH$_4$]$^+$) and one other fragment ([MH–H$_2$O]$^+$) were evident (FIGS. 1, 2 and 3). This actually allowed the presence or absence of a tag to be determined by the observation of two signals, which removes any possible ambiguity when analyzing a more complex mixture. Approximately equal amounts of the three tags were then mixed and analyzed by PCIMS (FIG. 5). Again, the two signals corresponding to each separate tag could easily be distinguished.

Tag 4 was now transformed into the diazoketone precursor 8 (Scheme 9), then attached to Tentagel resin as 9 (Scheme 12). One bead of the 9 was subsequently removed and 4 oxidatively released using ceric ammonium nitrate. PCIMS analysis again clearly showed the presence of tag 4.

In summary, the set of tags 4, 11 and 13 of the same structure, but different molecular weights were synthesized. All were easily detected simultaneously in a mixture by PCIMS. The small amount of 4 released from a single bead of Tentagel resin used in combinatorial library synthesis is detectable by PCIMS. MS is a viable and sensitive detection method for tags, and can be used as the basis for an encoding scheme of a combinatorial library.

Analysis of 4, 11 and 13 by PCIMS was obtained using a reagent gas mixture of 1% NH$_3$ in CH$_4$.

(2). To a solution of 11.1 mL (125 mmole, 5.00 eq.) of 1,4-butanediol (1), 6.97 mL (50.0 mmole, 2.00 eq.) of Et$_3$N and 0.153 g (1.25 mmole, 0.05 eq.) of 4-dimethylaminopyridine in dry CH$_2$Cl$_2$ (100 mL) at 0° C. under Ar, was added 3.88 g (25.0 mmole, 1.00 eq.) of 97% tert-butyldimethylsilyl chloride. The resulting solution was stirred at 0° C. for 15 min, then 25° C. for 16 hours. The reaction was then diluted with CH$_2$Cl$_2$ (250 mL) and washed with 1M HCl (100 mL), saturated aq. NaHCO$_3$ (100 mL) and H$_2$O (100 mL), then dried (MgSO$_4$). Removal of the volatiles in vacuo gave the crude product 2 as an oil.

(3). To a solution of ~10.0 mmole of crude alcohol 2, 1.93 g (10.5 mmole, 1.05 eq.) of pentafluorophenol and 2.89 g (11.0 mmole, 1.10 eq.) of triphenylphosphine in dry CH$_2$Cl$_2$ (40 mL) at 0° C. under Ar, was added 1.73 mL (11.0 mmole, 1.10 eq.) of diethyl azodicarboxylate. The resulting orange solution was stirred at 0° C. for 5 min, then 25° C. for 15 hours. The reaction was then diluted with CH$_2$Cl$_2$ (250 mL) and washed with saturated aq. Na$_2$CO$_3$ (100 mL), saturated aq. NH$_4$Cl (100 mL) and H$_2$O (100 mL), then dried (MgSO$_4$). Removal of the volatiles in vacuo and purification by flash chromatography (0–20% EtOAc in hexanes) gave the product 3 as an oil.

(4). To a solution of 1.85 g (5.00 mmole, 1.00 eq.) of silyl-protected alcohol 3 in THF (20 mL) at 25° C., was added 10.0 ML (10.0 mmole, 2.00 eq.) of a 1.0M solution of tetrabutylammonium fluoride in THF. The resulting orange solution was stirred at 25° C. for 4 hours. Removal of the volatiles in vacuo and purification by flash chromatography (20–40% EtOAc in hexanes) gave 1.10 g (86%) of the product 4 as an oil.

(5). To a solution of 0.800 g (3.125 mmole, 1.00 eq.) of alcohol 4, 0.569 g (3.125 mmole, 1.00 eq.) of methyl vanillate and 0.984 g (3.75 mmole, 1.20 eq.) of triphenylphosphine in dry CH$_2$Cl$_2$ (20 mL) at 0° C. under Ar, was added 0.591 mL (3.75 mmole, 1.20 eq.) of diethyl azodicarboxylate. The resulting pale yellow solution was stirred at 0° C. for 5 min, then 25° C. for 19 hours. The reaction was then diluted with CH$_2$Cl$_2$ (100 mL) and washed with 1M NaOH (50 mL), saturated aq. NH$_4$Cl (50 mL) and H$_2$O (50 mL), then dried (MgSO$_4$). Removal of the volatiles in vacuo and purification by flash chromatography (20% EtOAc in hexanes) gave the product 5 as an oil.

(6). To a solution of 3.125 mmole of ester 5 in THF (12 mL) was added 1.31 g (31.3 mmole, 10.0 eq.) of lithium hydroxide monohydrate. MeOH (24 mL) was added to the resulting suspension to form a solution, which was stirred at 25° C. for 1 hours, then refluxed for 1 day. Volatiles were removed in vacuo, and 1M HCl then added until solution was ~pH 1. The white precipitate of product which formed was collected and dried to give 0.968 g (76% ~2 steps) of 6.

(7). To 0.968 g (2.38 mmole, 1.00 eq.) of carboxylic acid 6 under Ar, was added 2.43 mL of thionyl chloride. The resulting suspension was refluxed for 1.5 hours, after which time a yellow solution had formed. Volatiles were removed in vacuo, and the resulting residue azeotroped three times with toluene to give the product 7 as colorless crystals.

(8). To a solution of 2.38 mmole of acid chloride 7 in 1:1 THF:MeCN (20 mL) at 0° C. under Ar, was added 1.16 mL (8.33 mmole, 3.50 eq.) of Et$_3$N followed by 3.57 mL (7.14 mmole, 3.00 eq.) of a 2.0M solution of (trimethylsilyl) diazomethane in hexanes. The resulting yellow solution was stirred at 0° C. for 1 h, then 25° C. for 1 day. The reaction was diluted with EtOAc (150 mL) and washed with saturated aq. NaHCO$_3$ (2×75 mL) and saturated aq. NaCl (2×75 mL), then dried (MgSO$_4$). Removal of the volatiles in vacuo gave the crude product 8 as an oil.

(11). Using commercially available 1,4-butanediol-2,2,3,3-$d_4$ (10) in place of 1, and an analogous procedure to that described for the transformation 1 into 4, 11 was obtained in 41% yield over three steps.

Using commercially available 1,4-butanediol-2,2,3,3,4,4-$d_8$ (10) in place of 1, and an analogous procedure to that described for the transformation 1 into 4, 13 was obtained in 42% yield over three steps.

Tag 4 was introduced onto the solid support using 5 to 50% (w/w vs. resin) precursor diazoketone 8 to give 9 by essentially the same procedure given in Example 4; the Hetero Diels-Alder library. Tag 4 was also subsequently removed from 9 by essentially the same procedure as Step G in Example 4.

The diazoketones corresponding to tags 11 and 13 are used to introduce these tags onto the solid support, so that along with 8, they yield members of a binary encoding set.

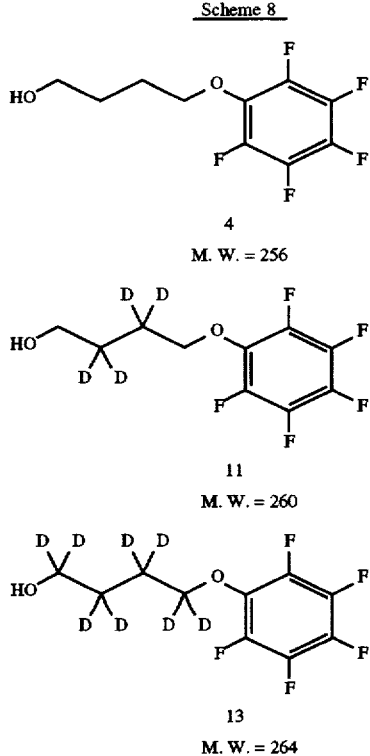

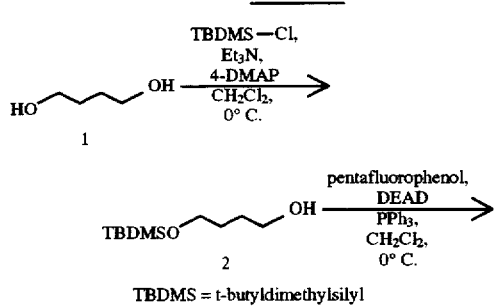

TBDMS = t-butyldimethylsilyl

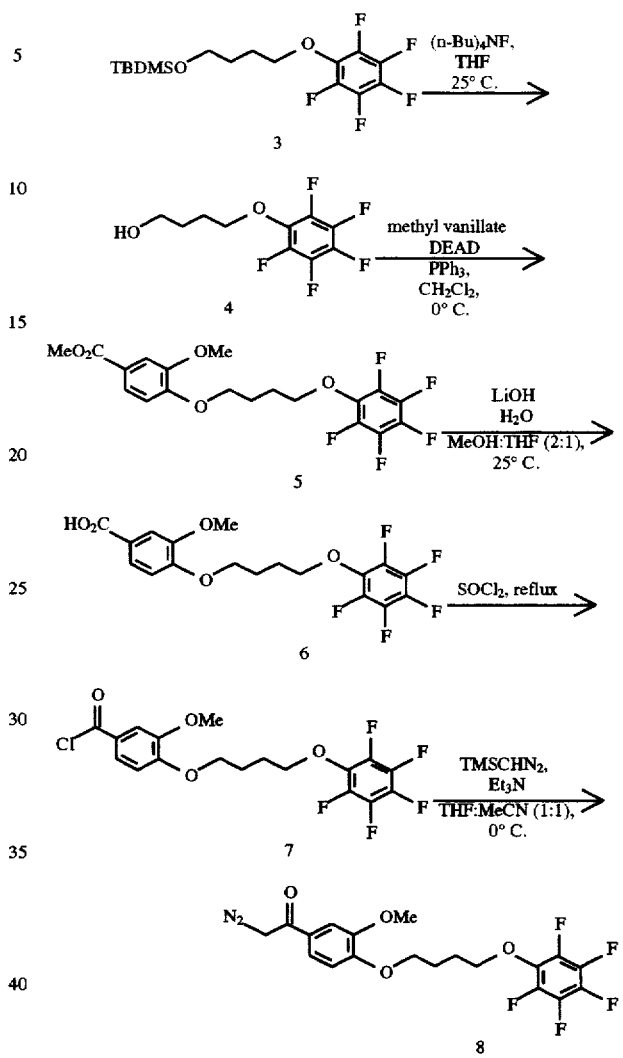

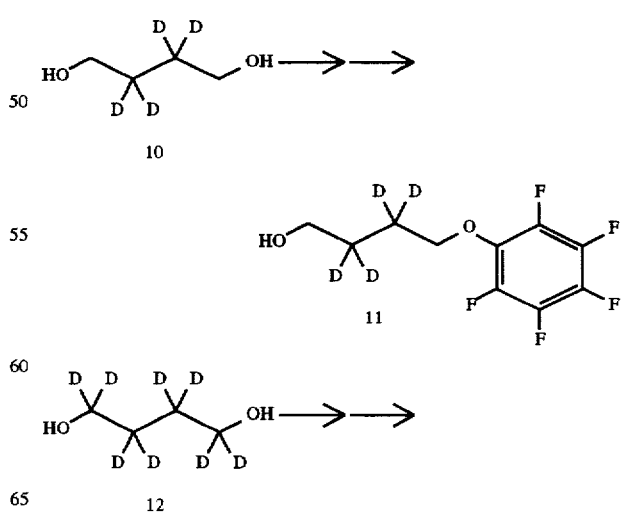

-continued

Scheme 10

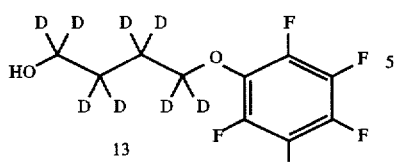

13

Scheme 11

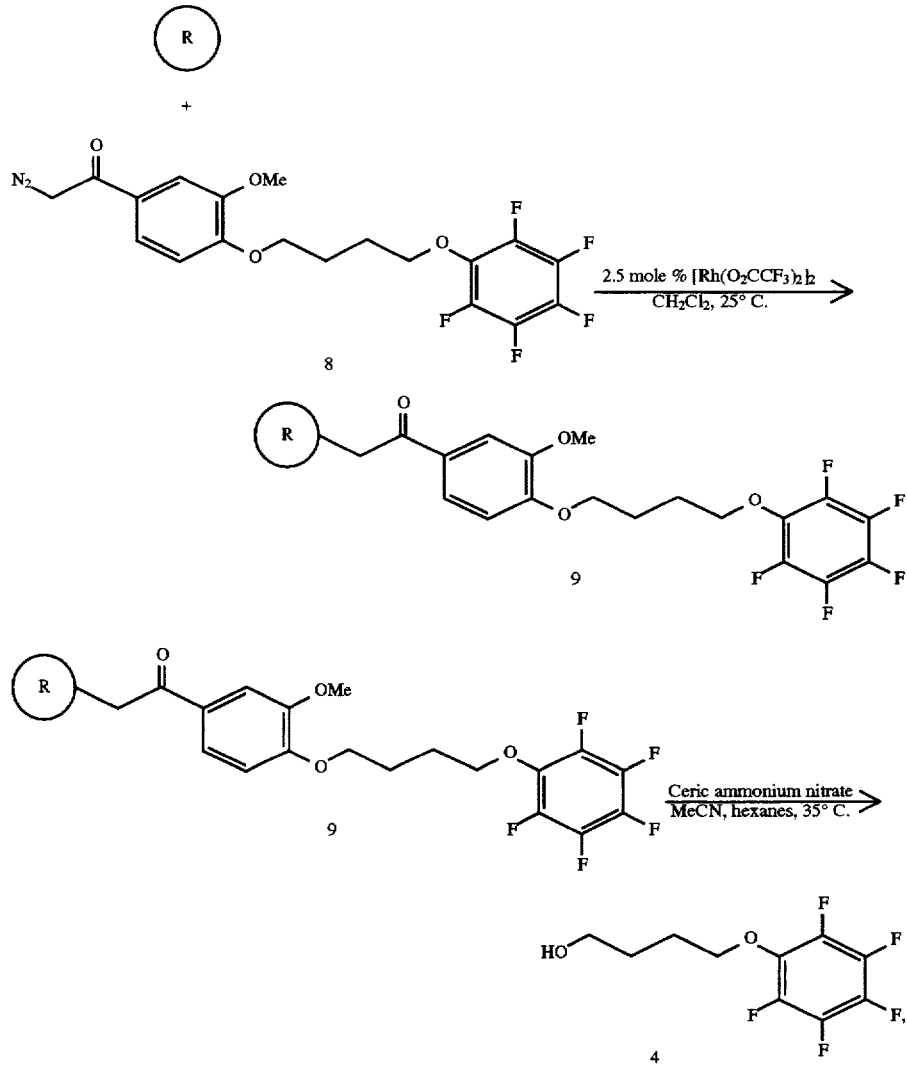

producing the products of interest. The tags can be readily synthesized and permit accurate analysis, so as to accurately define the nature of the composition.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of It is evident from the above description that the subject invention provides a versatile, simple method for identifying compounds, where the amount of compound present precludes any assurance of the ability to obtain an accurate determination of its reaction history. The method allows for the production of extraordinarily large numbers of different products, which can be used in various screening techniques to determine biological or other activity of interest. The use of tags which are chemically inert under the process conditions allows for great versatility in a variety of environments produced by the various synthetic techniques employed for this invention that certain changes and modifications may be made thereto without departing from the spirit or scope of the appended claims.

What is claimed is:

1. A method of determining the structure of a compound, which comprises:

a) providing a solid support on which a compound was synthesized by a reaction series comprising at least a first stage reagent and first stage reaction condition and a second stage reagent and second stage reaction condition, wherein the first stage precedes the second stage in the reaction series, which solid support has attached thereto:
  i. a first identifier having a first non-sequencable tag, which tag comprises a code that records the first stage reagent or the first stage reaction condition; and
  ii. a second identifier having a second non-sequencable tag, which tag comprises a code that records the second stage reagent or the second stage reaction condition;
b) detaching the tags from the solid support such that a mixture of soluble tags is formed;
c) separating the mixed first and second tags, each from the other; and
d) determining the identity of each of the separated tags, whereby the identities of the reagents and reaction conditions of the first and the second stage of the reaction series are determined.

2. The method of claim 1, wherein the first tag and second tag are attached to the solid support through a detachable linker.

3. The method of claim 2, wherein the detachable linker comprises an alkyl ortho-methoxyphenyl ether.

4. The method of claim 1, wherein, after detachment, each tag comprises not more 100 atoms, other than hydrogen atoms.

5. The method of claim 1, wherein, after detachment, each tag comprises not more 60 atoms, other than hydrogen atoms.

6. The method of claim 1, wherein each tag comprises a haloalkyl or haloarylalkyl moiety.

7. The method of claim 1, wherein the reagent of each stage of the reaction series is recorded by a code consisting of a tag attached to the support or a combination of tags attached to the support.

8. The method of claim 7, wherein the first tag and the second tag are attached to the solid support through a detachable linker.

9. The method of claim 8, wherein the detachable linker comprises an alkyl ortho-methoxyphenyl ether.

10. The method of claim 7, wherein, after detachment, each tag comprises not more 100 atoms, other than hydrogen atoms.

11. The method of claim 7, wherein, after detachment, each tag comprises of not more 60 atoms, other than hydrogen atoms.

12. The method of claim 7, wherein each tag comprises a haloalkyl or haloarylalkyl moiety.

13. A method of determining the structure of a compound, which comprises:
  a) providing a solid support on which a compound was synthesized by a reaction series comprising at least a first stage reagent and reaction condition and a second stage reagent and reaction condition, wherein the first stage precedes the second stage in the reaction series, which solid support has attached thereto:
    i. a first plurality of identifiers each having one of a first plurality of non-sequencable tags, the combination of which tags records the first stage reagent or the first stage reaction condition; and
    ii. a second plurality of identifiers each having one of a second plurality of non-sequencable tags, the combination of which tags records the second reagent or second reaction condition;
  b) detaching the tags of the first and second pluralities from the solid support such that a mixture of soluble tags is formed;
  c) separating the mixed tags of the first and second pluralities, each tag from the others; and
  d) determining the identity of each of the separated tags, whereby the identities of the reagents and reaction conditions of the first and the second stage of the reaction series of interest are determined.

14. The method of claim 13, wherein each tag of the first and second pluralities is attached to the solid support through a detachable linker.

15. The method of claim 14, wherein the detachable linker comprises an alkyl ortho-methoxyphenyl ether.

16. The method of claim 13, wherein, each detached tag comprises not more 100 atoms, other than hydrogen atoms.

17. The method of claim 13, wherein each detached tag comprises not more 60 atoms, other than hydrogen atoms.

18. The method of claim 13, wherein each tag comprises a haloalkyl or haloarylalkyl moiety.

19. The method of claim 13, wherein the reagent of each stage of the reaction series is recorded by a code consisting of a tag attached to the support or a combination of tags attached to the support.

20. The method of claim 19, wherein each tag of the first and second pluralities is attached to the solid support through a detachable linker.

21. The method of claim 20, wherein the detachable linker comprises an alkyl ortho-methoxyphenyl ether.

22. The method of claim 19, wherein each detached tag comprises not more 100 atoms, other than hydrogen atoms.

23. The method of claim 19, wherein each detached tag comprises not more 60 atoms, other than hydrogen atoms.

24. The method of claim 19, wherein each tag comprises a haloalkyl or haloarylalkyl moiety.

* * * * *